United States Patent
Yu et al.

(10) Patent No.: US 9,333,223 B2
(45) Date of Patent: *May 10, 2016

(54) COMPOSITIONS AND METHODS FOR TREATING CONDITIONS OF COMPROMISED SKIN BARRIER FUNCTION

(71) Applicant: Olivo Laboratories, LLC, Cambridge, MA (US)

(72) Inventors: Betty Yu, Cambridge, MA (US); Joseph Lomakin, Cambridge, MA (US); Soo-Young Kang, Newton, MA (US); Benjamin W. Adams, Somerville, MA (US)

(73) Assignee: OLIVO LABORATORIES, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/624,483

(22) Filed: Sep. 21, 2012

(65) Prior Publication Data
US 2013/0078209 A1  Mar. 28, 2013

Related U.S. Application Data

(60) Provisional application No. 61/537,307, filed on Sep. 21, 2011, provisional application No. 61/607,905, filed on Mar. 7, 2012, provisional application No. 61/607,908, filed on Mar. 7, 2012.

(51) Int. Cl.
*A61K 31/80* (2006.01)
*A61K 9/70* (2006.01)
*A61K 9/00* (2006.01)

(52) U.S. Cl.
CPC ............... *A61K 31/80* (2013.01); *A61K 9/0014* (2013.01); *A61K 9/7015* (2013.01)

(58) Field of Classification Search
CPC ........................... A61K 9/7015; A61K 9/0014
See application file for complete search history.

(56) References Cited

U.S. PATENT DOCUMENTS

| | | |
|---|---|---|
| 3,884,866 A | 5/1975 | Jeram et al. |
| 5,219,560 A | 6/1993 | Suzuki et al. |
| 5,525,344 A | 6/1996 | Wivell |

(Continued)

FOREIGN PATENT DOCUMENTS

| | | |
|---|---|---|
| EP | 0865787 A1 | 9/1998 |
| EP | 2090294 A1 | 8/2009 |

(Continued)

OTHER PUBLICATIONS

Correct Combo, [retrieved on Dec. 10, 2014 from on-line website http://www.drugs.com/otc/122754/correct-combo.html].*

(Continued)

*Primary Examiner* — Ernst V Arnold
*Assistant Examiner* — Kyung Sook Chang
(74) *Attorney, Agent, or Firm* — Kramer Levin Naftalis & Frankel LLP

(57) ABSTRACT

This invention relates to compositions and methods useful in treating dermatological disorders. In particular, the methods include applying a composition that includes a reactive reinforcing component; and a cross-linking component; in which the cross-linking component facilitates in situ cross-linking of the reactive reinforcing component, such that a film is formed on skin, thereby treating the dermatological disorder.

26 Claims, 7 Drawing Sheets

Day 4: 80 hours following film use, pigmented lesion sloughed off with film.

(56) References Cited

U.S. PATENT DOCUMENTS

| | | |
|---|---|---|
| 5,919,437 A | 7/1999 | Lee et al. |
| 5,919,468 A | 7/1999 | Bara |
| 5,922,470 A | 7/1999 | Bracken et al. |
| 6,066,326 A * | 5/2000 | Afriat et al. ............... 424/401 |
| 6,342,237 B1 | 1/2002 | Bara |
| 6,471,985 B2 | 10/2002 | Guyuron et al. |
| 6,512,072 B1 | 1/2003 | Gantner et al. |
| 6,544,532 B1 * | 4/2003 | Jager-Lezer et al. ......... 424/401 |
| 6,573,299 B1 * | 6/2003 | Petrus ........................ 514/558 |
| 6,613,185 B1 | 9/2003 | Valade et al. |
| 6,682,749 B1 | 1/2004 | Potechin et al. |
| 7,078,026 B2 | 7/2006 | Ferrari et al. |
| 7,083,800 B1 * | 8/2006 | Terren et al. ............... 424/401 |
| 7,270,828 B2 | 9/2007 | Masuda et al. |
| 7,482,419 B2 | 1/2009 | Caprasse et al. |
| 7,750,106 B2 | 7/2010 | Zheng et al. |
| 8,133,478 B2 | 3/2012 | Maitra et al. |
| 8,263,055 B2 | 9/2012 | Do |
| 8,691,202 B2 | 4/2014 | Yu et al. |
| 2002/0022040 A1 | 2/2002 | Robinson et al. |
| 2002/0122771 A1 * | 9/2002 | Holland et al. ............. 424/43 |
| 2004/0258628 A1 | 12/2004 | Riedel et al. |
| 2005/0148727 A1 | 7/2005 | Ajbani et al. |
| 2005/0158260 A1 | 7/2005 | Ferrari et al. |
| 2005/0175562 A1 | 8/2005 | Hadasch et al. |
| 2006/0029623 A1 * | 2/2006 | Astruc et al. ............... 424/400 |
| 2007/0142575 A1 * | 6/2007 | Zheng et al. ............... 525/478 |
| 2007/0142599 A1 | 6/2007 | Zheng et al. |
| 2007/0212314 A1 | 9/2007 | Murphy et al. |
| 2007/0244230 A1 | 10/2007 | Sixt et al. |
| 2008/0102050 A1 | 5/2008 | Li et al. |
| 2008/0159970 A1 | 7/2008 | Willemin |
| 2009/0214455 A1 | 8/2009 | Blin et al. |
| 2010/0152135 A1 | 6/2010 | Blin |
| 2010/0179105 A1 | 7/2010 | Blin et al. |
| 2011/0040242 A1 | 2/2011 | Fallon et al. |
| 2012/0237461 A1 | 9/2012 | Yu et al. |
| 2012/0251600 A1 | 10/2012 | Yu et al. |
| 2013/0078209 A1 | 3/2013 | Yu et al. |

FOREIGN PATENT DOCUMENTS

| | | |
|---|---|---|
| FR | 2894817 A1 | 6/2007 |
| FR | 2910291 A1 | 6/2008 |
| WO | 2007071886 A2 | 6/2007 |
| WO | 2008075282 A2 | 6/2008 |
| WO | 2009090242 A1 | 7/2009 |
| WO | 2011001217 A1 | 1/2011 |
| WO | 2013044098 A1 | 3/2013 |
| WO | 2013076450 A1 | 5/2013 |

OTHER PUBLICATIONS

Silicones Plus product list, [retrieved on Dec. 10, 2014 from on-line website http://siliconesplus.com/storage/Silicones%20Plus%20Brochure_1.pdf].*

Klykken, Paal, et al., "Silicone Film-Forming Technologies for Health Care Applications", Dow Corning, 2004; 8pp.

International Search Report for related PCT Application No. PCT/US2011/050016, Apr. 30, 2012; 4 pp.

International Search Report for related PCT Application No. PCT/US2011/050003, Apr. 19, 2012; 6pp.

International Search Report for related PCT Application No. PCT/US2012/056667 Dec. 3, 2012; 4 pp.

Written Opinion for related PCT Application No. PCT/US2012/056667 Dec. 3, 2012; 8 pp.

Leow, Y-H, et al., Effect of Occlusion on Skin, Journal of Dermatological Treatment 8:139-142, 1997.

Hwang, Sang Min, et al., Basis of Occlusive Therapy in Psoriasis: Correcting Defects in Permeability Barrier and Calcium Gradient, International Jountal of Dermatology, 40:223-231, 2001.

* cited by examiner

Day 1: post-laser treatment

Day 1: 24 hours after laser treatment

Day 1: 24 hours after treatment, with film

Day 3: 72 hours after treatment, with film

Day 4: 80 hours following film use, pigmented lesion sloughed off with film.

COMPOSITIONS AND METHODS FOR TREATING CONDITIONS OF COMPROMISED SKIN BARRIER FUNCTION

RELATED APPLICATIONS

This application claims the benefit of U.S. Provisional Patent Application No. 61/537,307, filed Sep. 21, 2011; U.S. Provisional Patent Application No. 61/607,905, filed Mar. 7, 2012; and U.S. Provisional Patent Application No. 61/607,908, filed Mar. 7, 2012. The entire contents of the foregoing applications are hereby incorporated by reference.

BACKGROUND OF THE INVENTION

Many dermatological disorders are chronic disorders that may only be managed by long-term administration, and even lifetime administration, of various medications. However, many of these medications have serious side effects. For example, psoriasis and eczema may be treated with drugs such as topical corticosteroids, immunomodulators, such as tacrolimus and pimecrolimus, immune suppressants, such as cyclosporine azathioprine and methotrexate, and biological agents, such as antibodies. The side effects of the foregoing medications include severe skin irritation, sensitivity to the sun, suppression of the immune system, anemia and kidney problems. These side effects limit the utility of existing therapies due to the risks presented, and exclude patient populations who suffer from preexisting immunocomprised conditions or those whose medication regimen preclude use of other drugs from the classes listed above. Occlusive therapy has been used in psoriasis, but the effects of occlusion on psoriasis are not completely understood (see e.g., Hwang et al., *Internat. J. Dermatol.* (2001) 40, 223-231).

Laser- or light-based dermatological procedures such as removal of pigmented lesions, facial rejuvenation, and skin tightening are increasing in frequency. Possible complications resulting from these procedures include erythema, infection, and scarring. Petrolatum application to the treatment site is a standard post-treatment management practice, as petrolatum is known to facilitate healing of the treatment site. However, topical use of moisturizers often requires multiple applications per day to be effective and to prevent it from wearing off by contact, sweat and other normal activities. Therefore, it is desirable to find alternative methods of treating that are non-invasive and provide treatment without undesirable and dangerous side effects.

Therefore, it is desirable to find alternative methods of treating dermatological disorders, managing post-laser or light or chemical peel treatments in subjects in need thereof, or otherwise improving conditions of compromised skin barrier in subjects in need thereof that are non-invasive and provide treatment without undesirable and dangerous side effects.

SUMMARY OF THE INVENTION

The present invention is based, at least in part, on the discovery that durable, natural looking, non-invasive compositions that are used in cosmetic applications for masking skin and body imperfections are useful in treating conditions of compromised skin barrier function such as dermatological disorders and post-laser or light-treatment recovery management or chemical peel treatment management. The invention provides a durable, convenient, long-lasting coating with skin occlusive benefits. The formulation, composition or film of the invention provides a transparent or a tinted coating for the treatment site. The formulations, compositions or films of the invention are more comfortable because each form an aesthetically pleasing, durable, skin conforming flexible layer over the skin, thereby increasing subject compliance as compared to current coatings or dressings or patches. Moreover, the chemical and physical properties of the formulation, composition or film of the invention are tunable to form a coating that is best suited for the location on the subject and the type of dermatological disorder to be treated or the location on the subject of the laser or light or chemical treatment and the type of laser or light or chemical peel treatment used.

Accordingly, in one aspect the invention provides a method for treating a dermatological disorder in a subject in need thereof, comprising: applying to the subject's skin a composition comprising a) a reactive reinforcing component; and b) a cross-linking component; in which the cross-linking component facilitates in situ cross-linking of the reactive reinforcing component, such that a film is formed on skin, thereby treating the dermatological disorder.

In one embodiment, the invention provides a method for treating symptoms of conditions of compromised skin barrier function with the formulations and films disclosed herein. In one aspect of this embodiment, the invention provides formulations, film and methods for treating itchy skin; for treating raw skin; for treating dry skin; for treating flaking or peeling skin; for treating blisters on skin; for treating redness or swelling or inflammation of the skin; or for treating oozing, scabbing and scaling skin.

In one embodiment, the invention provides a method for occluding skin on a subject in need thereof, comprising: applying to the subject a composition comprising
  a) a reactive reinforcing component; and
  b) a cross-linking component;
wherein said cross-linking component facilitates in situ cross-linking of the reactive reinforcing component, such that a film is formed on skin, thereby occluding the skin.

In a specific embodiment, occlusion of skin is used to treat conditions of compromised skin barrier such as dermatological disorders and skin after light or laser or chemical peel treatment.

In one aspect the invention provides a method for hydrating skin in a subject in need thereof, comprising: applying to the subject's skin a composition comprising a) a reactive reinforcing component; and b) a cross-linking component; wherein said cross-linking component facilitates in situ cross-linking of the reactive reinforcing component, such that a film is formed on skin, thereby hydrating the skin.

In at least one embodiment, the subject has one or more dermatological disorders. In at least one embodiment, the subject has one dermatological disorder. In at least one embodiment, the subject has more than one dermatological disorder. In at least one embodiment, the subject has a condition that results in or is associated with a dermatological disorder.

In at least one embodiment, the dermatological disorder is lichen simplex chronicus, cutaneous lupus, psoriasis, eczema, chronic dry skin, xeroderma, rosacea, ichthyosis, or an ulcer, or any combination thereof. In a specific embodiment, the dermatological disorder is xeroderma, eczema, psoriasis, rosacea and ichthyosis or any combination thereof. In a specific embodiment, the eczema is atopic dermatitis. In a particular embodiment, the dermatological disorder is xeroderma, atopic dermatitis, psoriasis, rosacea and ichthyosis or any combination thereof. In a particular embodiment, the dermatological disorder is an ulcer.

In one embodiment, the invention provides non-invasive formulations that form a film upon application to the subject, thereby ameliorating dermatological disorders. The invention also provides methods of using such formulations. In another embodiment, the invention provides cleansers to remove the film.

In some aspects, the invention provides a composition for treating a dermatological disorder in a subject in need thereof, in which the composition comprises a) a reactive reinforcing component; and b) a cross-linking component; wherein the cross-linking component facilitates in situ cross-linking of the reactive reinforcing component, such that a film is formed on skin.

Accordingly, in one embodiment, the invention pertains, at least in part, to formulations for application to skin to treat a dermatological disorder that comprise a) a reactive reinforcing component; and b) a cross-linking component; in which the cross-linking component facilitates in situ cross-linking of the reactive reinforcing component, such that a film is formed on skin and the film has an appearance of natural skin.

In one embodiment, the invention pertains, at least in part, to two part formulation for application to skin to treat a dermatological disorder that comprise a) a reactive reinforcing component; and b) a cross-linking component; in which the reactive reinforcing component and the cross-linking component are prevented from coming into contact prior to use; and in which the cross-linking component facilitates in situ cross-linking of the reactive reinforcing component, such that a film is formed on skin.

In one embodiment, the invention provides, at least in part, to formulations for application to skin to treat a dermatological disorder that comprise a) a reactive reinforcing component; and b) a cross-linking component; in which the reactive reinforcing component has a viscosity of between about 5,000 and about 1,000,000 cSt or cP at 25° C.; and in which the cross-linking component facilitates in situ cross-linking of the reactive reinforcing component, such that a film is formed on skin.

In one embodiment, the invention provides, at least in part, to formulations for application to skin to treat a dermatological disorder that comprise a) a reactive reinforcing component; and b) a cross-linking component; in which the reactive reinforcing component has a viscosity of between about 5,000 and about 2,000,000 cSt or cP at 25° C.; and in which the cross-linking component facilitates in situ cross-linking of the reactive reinforcing component, such that a film is formed on skin.

In one embodiment, the invention pertains, at least in part, to formulations for application to skin to treat a dermatological disorder that comprise a) a reactive reinforcing component; and b) a cross-linking component in which the reactive reinforcing component has a vinyl to functional hydride ratio of between about 1:10 and about 1:100; and in which the cross-linking component facilitates in situ cross-linking of the reactive reinforcing component, such that a film is formed on skin.

In one embodiment, the invention pertains, at least in part, to formulations for application to skin to treat a dermatological disorder that comprise a) a reactive reinforcing component; and b) a cross-linking component in which the reactive reinforcing component has a vinyl to functional hydride ratio of between about 1:4 and about 1:100; and in which the cross-linking component facilitates in situ cross-linking of the reactive reinforcing component, such that a film is formed on skin.

In one embodiment, the invention pertains, at least in part, to films to treat a dermatological disorder prepared by a process comprising the steps of: a) applying a reactive reinforcing component to skin; and b) applying a cross-linking component to the reactive reinforcing component, in which the cross-linking component facilitates in situ cross-linking of the reactive reinforcing component, such that a film is formed on skin.

In one embodiment, the invention pertains, at least in part, to methods for delivering an agent to a subject to treat a dermatological disorder, comprising applying to the subject a formulation comprising a) a reactive reinforcing component optionally comprising one or more agents; and b) a cross-linking component optionally comprising one or more agents; in which the cross-linking component facilitates in situ cross-linking of the reactive reinforcing component such that a film is formed on skin, thereby delivering the agent to the subject.

In some aspects, the invention provides a kit for use in treating a subject with a dermatological disorder comprising a) a reactive reinforcing component; b) a cross-linking component; and c) instructions for use.

In one embodiment, the invention pertains, at least in part, to therapeutic formulations for application to treat a dermatological disorder in a subject in need thereof, comprising at least one preselected function modulating component, in which the composition forms a therapeutic film upon application to the subject.

In one embodiment, the invention pertains, at least in part, to therapeutic formulations for application to a subject to treat a dermatological disorder that target a treatment area on the subject, comprising at least one preselected treatment specific component, wherein the composition forms a therapeutic film upon application to the target treatment area on the subject.

In one embodiment, the invention pertains, at least in part, to a film removing cleanser for use in removing a therapeutic film to treat a dermatological disorder, wherein the film is prepared by a process comprising the steps of applying a reactive reinforcing component to skin; and applying a cross-linking component to said reactive reinforcing component, and wherein said cross-linking component facilitates in situ cross-linking of the reactive reinforcing component.

In another embodiment, the invention pertains, at least in part, to a film removing cleanser comprising a film wetting component, a penetration component, a film swelling component and a film release component.

In some embodiments, the invention pertains to a formulation for repairing a therapeutic film applied to skin to treat a dermatological disorder, wherein said formulation comprises a) a reactive reinforcing component and b) a cross-linking component, wherein the cross-linking component facilitates in situ cross-linking of the reactive reinforcing component such that a film is formed on skin.

In some embodiments, the invention pertains, at least in part, to a method for repairing a therapeutic film applied to skin to treat a dermatological disorder comprising the steps of a) identifying an area of the film in need of repair; b) optionally smoothing the edges of the film; and c) applying a formulation for repairing the film, wherein the formulation comprises a reactive reinforcing component and a cross-linking component, wherein the cross-linking component facilitates in situ cross-linking of the reactive reinforcing component such that a film is formed on skin, thereby repairing the therapeutic film.

In some embodiments, the invention pertains, at least in part, to a kit for repairing a therapeutic film to treat a dermatological disorder, the kit comprising a formulation comprising a) a reactive reinforcing component and b) a cross-linking component, wherein the cross-linking component facilitates in situ cross-linking of the reactive reinforcing component such that a film is formed on skin.

In one aspect the invention provides methods for treating a subject post-laser treatment, comprising applying to the subject a formulation comprising a) a reactive reinforcing component; and b) a cross-linking component; in which the cross-linking component facilitates in situ cross-linking of the reactive reinforcing component, such that a film is formed on skin, thereby treating a subject post-laser treatment.

In one embodiment, the invention provides non-invasive formulations that form a film upon application to a subject post laser treatment, thereby facilitating healing of the subject post-laser treatment. The invention also provides methods of using such formulations. In another embodiment, the invention provides cleansers to remove the film.

In some aspects, the invention provides a composition for treating a subject post-laser treatment, wherein the composition comprises a) a reactive reinforcing component; and b) a cross-linking component; in which the cross-linking component facilitates in situ cross-linking of the reactive reinforcing component upon application to skin, such that a film is formed on skin.

Accordingly, in one embodiment, the invention pertains, at least in part, to formulations for application to a subject post-laser treatment that comprise a) a reactive reinforcing component; and b) a cross-linking component; in which the cross-linking component facilitates in situ cross-linking of the reactive reinforcing component, such that a film is formed on skin and the film has an appearance of natural skin.

In one embodiment, the invention pertains, at least in part, to two part formulation for application to a subject post-laser treatment that comprise a) a reactive reinforcing component; and b) a cross-linking component; in which the reactive reinforcing component and the cross-linking component are prevented from coming into contact prior to use; and in which the cross-linking component facilitates in situ cross-linking of the reactive reinforcing component, such that a film is formed on skin.

In one embodiment, the invention provides, at least in part, to formulations for application to a subject post-laser treatment that comprise a) a reactive reinforcing component; and b) a cross-linking component; in which the reactive reinforcing component has a viscosity of between about 5,000 and about 1,000,000 cSt or cP at 25° C.; and in which the cross-linking component facilitates in situ cross-linking of the reactive reinforcing component, such that a film is formed on skin.

In one embodiment, the invention provides, at least in part, to formulations for application to a subject post-laser treatment that comprise a) a reactive reinforcing component; and b) a cross-linking component; in which the reactive reinforcing component has a viscosity of between about 5,000 and about 2,000,000 cSt or cP at 25° C.; and in which the cross-linking component facilitates in situ cross-linking of the reactive reinforcing component, such that a film is formed on skin.

In one embodiment, the invention pertains, at least in part, to formulations for application to a subject post-laser treatment on a subject's skin that comprise a) a reactive reinforcing component; and b) a cross-linking component in which the reactive reinforcing component has a vinyl to functional hydride ratio of between about 1:10 and about 1:100; and in which the cross-linking component facilitates in situ cross-linking of the reactive reinforcing component, such that a film is formed skin.

In one embodiment, the invention pertains, at least in part, to formulations for application to a subject post-laser treatment on a subject's skin that comprise a) a reactive reinforcing component; and b) a cross-linking component in which the reactive reinforcing component has a vinyl to functional hydride ratio of between about 1:4 and about 1:100; and in which the cross-linking component facilitates in situ cross-linking of the reactive reinforcing component, such that a film is formed skin.

In one embodiment, the invention pertains, at least in part, to films for treating a subject post-laser treatment prepared by a process comprising the steps of: a) applying a reactive reinforcing component to the subject; and b) applying a cross-linking component to the reactive reinforcing component, in which the cross-linking component facilitates in situ cross-linking of the reactive reinforcing component, such that a film is formed on skin.

In one embodiment, the invention pertains, at least in part, to methods for delivering an agent to a subject post-laser treatment, comprising applying to the subject a formulation comprising a) a reactive reinforcing component optionally comprising one or more agents; and b) a cross-linking component optionally comprising one or more agents; in which the cross-linking component facilitates in situ cross-linking of the reactive reinforcing component such that a film is formed on skin, thereby delivering the agent to the subject.

In some aspects, the invention provides a kit for use in treating a post-laser treatment on a subject in need thereof with a comprising a) a reactive reinforcing component; b) a cross-linking component; and c) instructions for use.

In one embodiment, the invention pertains, at least in part, to therapeutic formulations for application to a subject post-laser treatment, comprising at least one preselected function modulating component, in which the composition forms a therapeutic film upon application to the subject.

In one embodiment, the invention pertains, at least in part, to therapeutic formulations for application to a subject post-laser treatment on the subject that target a treatment area on a subject, wherein the targeted area area comprises an area that has been at least partially laser-treated, comprising at least one preselected treatment specific component, wherein the composition forms a therapeutic film upon application to the target treatment area on the subject.

In one embodiment, the invention pertains, at least in part, to a film removing cleanser for use in removing a therapeutic film used for post-laser treatment recovery management, wherein the film is prepared by a process comprising the steps of applying a reactive reinforcing component to skin; and applying a cross-linking component to said reactive reinforcing component, and wherein said cross-linking component facilitates in situ cross-linking of the reactive reinforcing component.

In another embodiment, the invention pertains, at least in part, to a film removing cleanser comprising a film wetting component, a penetration component, a film swelling component and a film release component.

In some embodiments, the invention pertains to a formulation for repairing a therapeutic film applied to a subject post-laser treatment, wherein said formulation comprises a) a reactive reinforcing component and b) a cross-linking component, wherein the cross-linking component facilitates in situ cross-linking of the reactive reinforcing component such that a film is formed on skin.

In some embodiments, the invention pertains, at least in part, to a method for repairing a therapeutic film applied to a subject post-laser treatment comprising the steps of a) identifying an area of the film in need of repair; b) optionally smoothing the edges of the film; and c) applying a formulation for repairing the film, wherein the formulation comprises a reactive reinforcing component and a cross-linking component, wherein the cross-linking component facilitates in situ cross-linking of the reactive reinforcing component such that a film is formed on skin, thereby repairing the therapeutic film.

In some embodiments, the invention pertains, at least in part, to a kit for repairing a therapeutic film used for post-laser treatment management, the kit comprising a formulation comprising a) a reactive reinforcing component and b) a cross-linking component, wherein the cross-linking component facilitates in situ cross-linking of the reactive reinforcing component such that a film is formed on skin.

In one aspect the invention provides methods for treating a subject post-light treatment, comprising applying to the subject a formulation comprising a) a reactive reinforcing component; and b) a cross-linking component; in which the cross-linking component facilitates in situ cross-linking of the reactive reinforcing component, such that a film is formed on skin, thereby treating a subject post-light treatment.

In one embodiment, the invention provides non-invasive formulations that form a film upon application to a subject post light treatment, thereby facilitating healing of the subject post-light treatment. The invention also provides methods of using such formulations. In another embodiment, the invention provides cleansers to remove the film.

In some aspects, the invention provides a composition for treating a subject post-light treatment, wherein the composition comprises a) a reactive reinforcing component; and b) a cross-linking component; in which the cross-linking component facilitates in situ cross-linking of the reactive reinforcing component upon application to skin, such that a film is formed on skin.

Accordingly, in one embodiment, the invention pertains, at least in part, to formulations for application to a subject post-light treatment that comprise a) a reactive reinforcing component; and b) a cross-linking component; in which the cross-linking component facilitates in situ cross-linking of the reactive reinforcing component, such that a film is formed on skin and the film has an appearance of natural skin.

In one embodiment, the invention pertains, at least in part, to two part formulation for application to a subject post-light treatment that comprise a) a reactive reinforcing component; and b) a cross-linking component; in which the reactive reinforcing component and the cross-linking component are prevented from coming into contact prior to use; and in which the cross-linking component facilitates in situ cross-linking of the reactive reinforcing component, such that a film is formed on skin.

In one embodiment, the invention provides, at least in part, to formulations for application to a subject post-light treatment that comprise a) a reactive reinforcing component; and b) a cross-linking component; in which the reactive reinforcing component has a viscosity of between about 5,000 and about 1,000,000 cSt or cP at 25° C.; and in which the cross-linking component facilitates in situ cross-linking of the reactive reinforcing component, such that a film is formed on skin.

In one embodiment, the invention provides, at least in part, to formulations for application to a subject post-light treatment that comprise a) a reactive reinforcing component; and b) a cross-linking component; in which the reactive reinforcing component has a viscosity of between about 5,000 and about 2,000,000 cSt or cP at 25° C.; and in which the cross-linking component facilitates in situ cross-linking of the reactive reinforcing component, such that a film is formed on skin.

In one embodiment, the invention pertains, at least in part, to formulations for application to a subject post-light treatment on a subject's skin that comprise a) a reactive reinforcing component; and b) a cross-linking component in which the reactive reinforcing component has a vinyl to functional hydride ratio of between about 1:10 and about 1:100; and in which the cross-linking component facilitates in situ cross-linking of the reactive reinforcing component, such that a film is formed skin.

In one embodiment, the invention pertains, at least in part, to formulations for application to a subject post-light treatment on a subject's skin that comprise a) a reactive reinforcing component; and b) a cross-linking component in which the reactive reinforcing component has a vinyl to functional hydride ratio of between about 1:4 and about 1:100; and in which the cross-linking component facilitates in situ cross-linking of the reactive reinforcing component, such that a film is formed skin.

In one embodiment, the invention pertains, at least in part, to films for treating a subject post-light treatment prepared by a process comprising the steps of: a) applying a reactive reinforcing component to the subject; and b) applying a cross-linking component to the reactive reinforcing component, in which the cross-linking component facilitates in situ cross-linking of the reactive reinforcing component, such that a film is formed on skin.

In one embodiment, the invention pertains, at least in part, to methods for delivering an agent to a subject post-light treatment, comprising applying to the subject a formulation comprising a) a reactive reinforcing component optionally comprising one or more agents; and b) a cross-linking component optionally comprising one or more agents; in which the cross-linking component facilitates in situ cross-linking of the reactive reinforcing component such that a film is formed on skin, thereby delivering the agent to the subject.

In some aspects, the invention provides a kit for use in treating a post-light treatment on a subject in need thereof with a comprising a) a reactive reinforcing component; b) a cross-linking component; and c) instructions for use.

In one embodiment, the invention pertains, at least in part, to therapeutic formulations for application to a subject post-light treatment, comprising at least one preselected function modulating component, in which the composition forms a therapeutic film upon application to the subject.

In one embodiment, the invention pertains, at least in part, to therapeutic formulations for application to a subject post-light treatment on the subject that target a treatment area on a subject, wherein the targeted area area comprises an area that has been at least partially light-treated, comprising at least one preselected treatment specific component, wherein the composition forms a therapeutic film upon application to the target treatment area on the subject.

In one embodiment, the invention pertains, at least in part, to a film removing cleanser for use in removing a therapeutic film used for post-light treatment recovery management, wherein the film is prepared by a process comprising the steps of applying a reactive reinforcing component to skin; and applying a cross-linking component to said reactive reinforcing component, and wherein said cross-linking component facilitates in situ cross-linking of the reactive reinforcing component.

In another embodiment, the invention pertains, at least in part, to a film removing cleanser comprising a film wetting component, a penetration component, a film swelling component and a film release component.

In some embodiments, the invention pertains to a formulation for repairing a therapeutic film applied to a subject post-light treatment, wherein said formulation comprises a) a reactive reinforcing component and b) a cross-linking component, wherein the cross-linking component facilitates in situ cross-linking of the reactive reinforcing component such that a film is formed on skin.

In some embodiments, the invention pertains, at least in part, to a method for repairing a therapeutic film applied to a subject post-light treatment comprising the steps of a) identifying an area of the film in need of repair; b) optionally smoothing the edges of the film; and c) applying a formulation for repairing the film, wherein the formulation comprises a reactive reinforcing component and a cross-linking component, wherein the cross-linking component facilitates in situ cross-linking of the reactive reinforcing component such that a film is formed on skin, thereby repairing the therapeutic film.

In some embodiments, the invention pertains, at least in part, to a kit for repairing a therapeutic film used for post-light treatment management, the kit comprising a formulation comprising a) a reactive reinforcing component and b) a cross-linking component, wherein the cross-linking component facilitates in situ cross-linking of the reactive reinforcing component such that a film is formed on skin.

In one aspect the invention provides methods for treating a subject after a chemical peel treatment, comprising applying to the subject a formulation comprising a) a reactive reinforcing component; and b) a cross-linking component; in which the cross-linking component facilitates in situ cross-linking of the reactive reinforcing component, such that a film is formed on skin, thereby treating a subject after a chemical peel treatment.

In one embodiment, the invention provides non-invasive formulations that form a film upon application to a subject post laser treatment, thereby facilitating healing of the subject after a chemical peel treatment. The invention also provides methods of using such formulations. In another embodiment, the invention provides cleansers to remove the film.

In some aspects, the invention provides a composition for treating a subject after a chemical peel treatment, wherein the composition comprises a) a reactive reinforcing component; and b) a cross-linking component; in which the cross-linking component facilitates in situ cross-linking of the reactive reinforcing component upon application to skin, such that a film is formed on skin.

Accordingly, in one embodiment, the invention pertains, at least in part, to formulations for application to a subject after a chemical peel treatment that comprise a) a reactive reinforcing component; and b) a cross-linking component; in which the cross-linking component facilitates in situ cross-linking of the reactive reinforcing component, such that a film is formed on skin and the film has an appearance of natural skin.

In one embodiment, the invention pertains, at least in part, to two part formulation for application to a subject after a chemical peel treatment that comprise a) a reactive reinforcing component; and b) a cross-linking component; in which the reactive reinforcing component and the cross-linking component are prevented from coming into contact prior to use; and in which the cross-linking component facilitates in situ cross-linking of the reactive reinforcing component, such that a film is formed on skin.

In one embodiment, the invention provides, at least in part, to formulations for application to a subject after a chemical peel treatment that comprise a) a reactive reinforcing component; and b) a cross-linking component; in which the reactive reinforcing component has a viscosity of between about 5,000 and about 1,000,000 cSt or cP at 25° C.; and in which the cross-linking component facilitates in situ cross-linking of the reactive reinforcing component, such that a film is formed on skin.

In one embodiment, the invention provides, at least in part, to formulations for application to a subject after a chemical peel treatment that comprise a) a reactive reinforcing component; and b) a cross-linking component; in which the reactive reinforcing component has a viscosity of between about 5,000 and about 2,000,000 cSt or cP at 25° C.; and in which the cross-linking component facilitates in situ cross-linking of the reactive reinforcing component, such that a film is formed on skin.

In one embodiment, the invention pertains, at least in part, to formulations for application to a subject after a chemical peel treatment on a subject's skin that comprise a) a reactive reinforcing component; and b) a cross-linking component in which the reactive reinforcing component has a vinyl to functional hydride ratio of between about 1:10 and about 1:100; and in which the cross-linking component facilitates in situ cross-linking of the reactive reinforcing component, such that a film is formed skin.

In one embodiment, the invention pertains, at least in part, to formulations for application to a subject after a chemical peel treatment on a subject's skin that comprise a) a reactive reinforcing component; and b) a cross-linking component in which the reactive reinforcing component has a vinyl to functional hydride ratio of between about 1:4 and about 1:100; and in which the cross-linking component facilitates in situ cross-linking of the reactive reinforcing component, such that a film is formed on skin.

In one embodiment, the invention pertains, at least in part, to films for treating a subject after a chemical peel treatment prepared by a process comprising the steps of: a) applying a reactive reinforcing component to the subject; and b) applying a cross-linking component to the reactive reinforcing component, in which the cross-linking component facilitates in situ cross-linking of the reactive reinforcing component, such that a film is formed on skin.

In one embodiment, the invention pertains, at least in part, to methods for delivering an agent to a subject after a chemical peel treatment, comprising applying to the subject a formulation comprising a) a reactive reinforcing component optionally comprising one or more agents; and b) a cross-linking component optionally comprising one or more agents; in which the cross-linking component facilitates in situ cross-linking of the reactive reinforcing component such that a film is formed on skin, thereby delivering the agent to the subject.

In some aspects, the invention provides a kit for use in treating a after a chemical peel treatment on a subject in need thereof with a comprising a) a reactive reinforcing component; b) a cross-linking component; and c) instructions for use.

In one embodiment, the invention pertains, at least in part, to therapeutic formulations for application to a subject after a chemical peel treatment, comprising at least one preselected function modulating component, in which the composition forms a therapeutic film upon application to the subject.

In one embodiment, the invention pertains, at least in part, to therapeutic formulations for application to a subject after a chemical peel treatment on the subject that target a treatment area on a subject, wherein the targeted area area comprises an area that has been at least partially laser-treated, comprising at least one preselected treatment specific component, wherein the composition forms a therapeutic film upon application to the target treatment area on the subject.

In one embodiment, the invention pertains, at least in part, to a film removing cleanser for use in removing a therapeutic film used after a chemical peel treatment, wherein the film is prepared by a process comprising the steps of applying a reactive reinforcing component to skin; and applying a cross-linking component to said reactive reinforcing component, and wherein said cross-linking component facilitates in situ cross-linking of the reactive reinforcing component.

In another embodiment, the invention pertains, at least in part, to a film removing cleanser comprising a film wetting component, a penetration component, a film swelling component and a film release component.

In some embodiments, the invention pertains to a formulation for repairing a therapeutic film applied to a subject after a chemical peel treatment, wherein said formulation comprises a) a reactive reinforcing component and b) a cross-linking component, wherein the cross-linking component facilitates in situ cross-linking of the reactive reinforcing component such that a film is formed on skin.

In some embodiments, the invention pertains, at least in part, to a method for repairing a therapeutic film applied to a subject after a chemical peel treatment comprising the steps of a) identifying an area of the film in need of repair; b) optionally smoothing the edges of the film; and c) applying a formulation for repairing the film, wherein the formulation comprises a reactive reinforcing component and a cross-linking component, wherein the cross-linking component facilitates in situ cross-linking of the reactive reinforcing component such that a film is formed on skin, thereby repairing the therapeutic film.

In some embodiments, the invention pertains, at least in part, to a kit for repairing a therapeutic film used after a chemical peel treatment, the kit comprising a formulation comprising a) a reactive reinforcing component and b) a cross-linking component, wherein the cross-linking component facilitates in situ cross-linking of the reactive reinforcing component such that a film is formed on skin.

In some embodiments, the film is used in combination with one or more additional therapeutic agents. In some embodiments, the additional therapeutic agent is a moisturizer, mineral oil, petroleum jelly, coal tar, anthralin, corticosteroids, fluocinonide, vitamin $D_3$ analogues, retinoids, phototherapy, methotrexate, cyclosporine, a monoclonal antibody, pimecrolimus, tacrolimus, azathioprine, fluoruracil, salicylic acid, benzoyl peroxide, antibiotics or alpha-hydroxy acids.

In some embodiments, the film has the appearance of natural skin.

In some embodiments, the reactive reinforcing component has a viscosity of between about 50,000 and 500,000 cSt or cP at 25° C.

In some embodiments, the reactive reinforcing component has a viscosity of between about 5,000 and 2,000,000 cSt or cP at 25° C.

In some embodiments, the reactive reinforcing component may have a viscosity between 0.1 and 1 cSt and cP.

In some embodiments, the reactive reinforcing component has a vinyl to functional hydride ratio of between about 1:10 and about 1:100.

In some embodiments, the reactive reinforcing component has a vinyl to functional hydride ratio of between about 1:4 and about 1:100.

In some embodiments, the reactive reinforcing component comprises a reactive constituent and a reinforcing constituent.

In some embodiments, the reactive constituent comprises at least one organopolysiloxane and at least one hydride functionalized polysiloxane. In some embodiments, the reactive constituent comprises at least one high viscosity organopolysiloxane, at least one low viscosity organopolysiloxane and at least one hydride functionalized polysiloxane. In some embodiments, the reactive constituent comprises at least one high viscosity organopolysiloxane or at least one low viscosity organopolysiloxane or a combination thereof.

In some embodiments, the organopolysiloxane is a high viscosity organopolysiloxane or a low viscosity organopolysiloxane or a combination thereof.

In some embodiments, high viscosity organopolysiloxane and the low-viscosity organopolysiloxane are selected from the group consisting of vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethylsiloxane terpolymer and combinations thereof.

In some embodiments, the reinforcing constituent is selected from the group consisting of optionally surface treated mica, zinc oxide, titanium dioxide, aluminum oxide, clay or silica.

In some embodiments, the reactive reinforcing component further comprises one or more of feel modifiers, spreadability enhancers, adhesion modifiers, diluents, tack modifiers, optics modifiers, particles, volatile siloxanes, emulsifiers, emollients, surfactants, thickeners, solvents, film formers, humectants, preservatives and pigments.

In some embodiments, the crosslinking component comprises a metal catalyst.

In some embodiments, the catalyst is a platinum catalyst.

In some embodiments, the catalyst is selected from the group consisting of platinum carbonyl cyclovinylmethylsiloxane complexes, platinum divinyltetramethyldisoloxane complexes, platinum cyclovinylmethylsiloxane complexes, platinum octanaldehyde/octanol complexes and combinations thereof.

In some embodiments, the cross-linking component further comprises one or more of feel modifiers, spreadability enhancers, adhesion modifiers, diluents, tack modifiers, optics modifiers, particles, volatile siloxanes, emulsifiers, emollients, surfactants, thickeners, solvents, film formers, humectants, preservatives catalyst stabilizers and pigments. In some embodiments, the addition of a catalyst stabilizer included at the molar ratio of catalyst to stabilizer of 0.1 to 10. The catalyst stabilizer may be a vinyl-substituted cyclic or linear siloxane such as tetravinyl tetramethylcyclotetrasiloxane, divinyltetramethyldisiloxane, trivinylpentamethyltrisiloxane, or divinyltetraethoxydislioxane. The stabilizers include other vinyl functionalized siloxanes with high vinyl density or alkylamines.

The crosslinking component may also take the form of a spray-on formulation. As a spray-on formulation, the crosslinking component may have a viscosity between 0.1 to 10 cPs or cSt at 25 C.

DETAILED DESCRIPTION OF THE INVENTION

Figure 1:
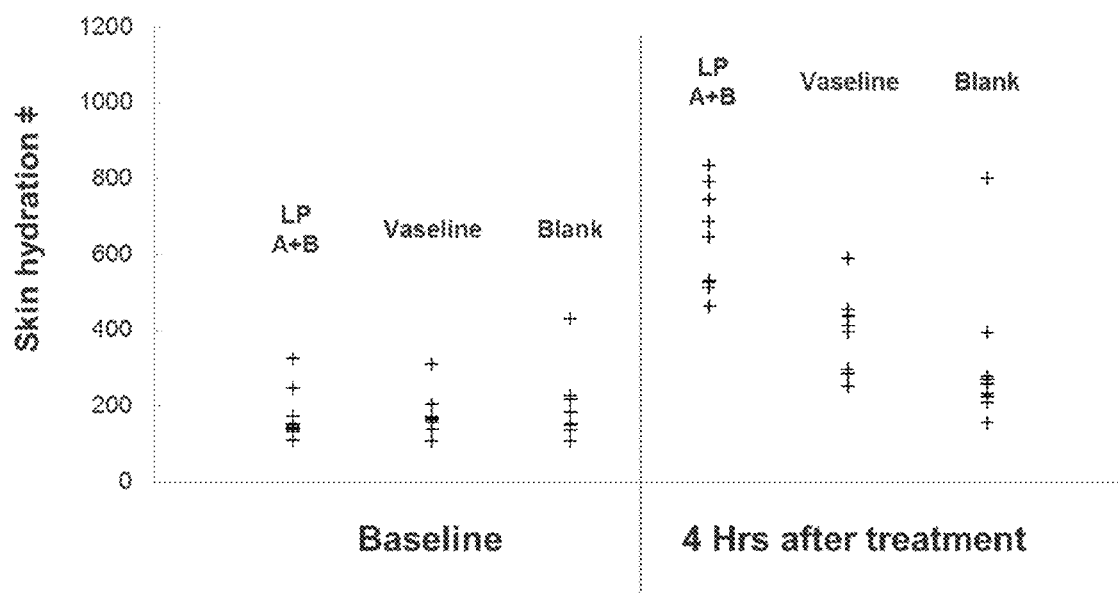
FIG. 1 is a scatter plot of the electrical conductance measurements for skin treated with LP A+B; Vaseline (Petrolatum; control) and for untreated skin (blank).
Figure 2:
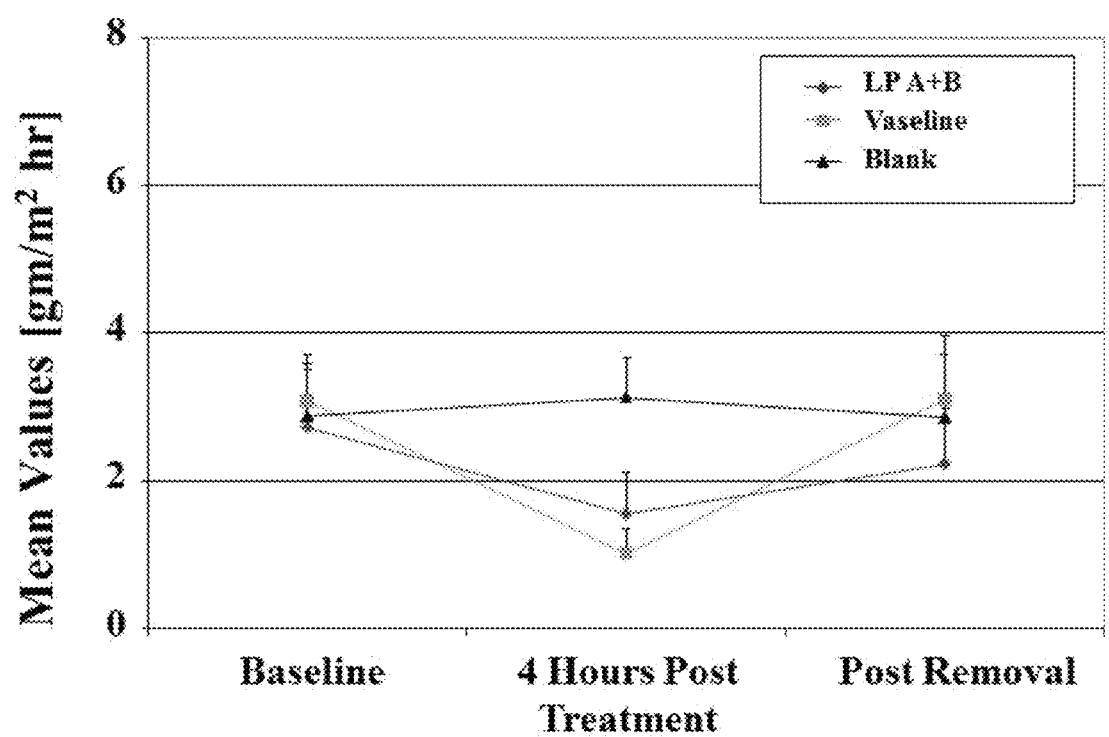
FIG. 2 is a graph of the moisture loss as measured by the DermaLab Transepidermal water loss (TEWL) evaporimeter method for skin treated with LP A+B; Vaseline (Petrolatum; control) and for untreated skin (blank).

Skin barrier function is critical to skin hydration, disease prevention, and appearance. Compromised skin barrier function has been characterized by increased transepidermal water loss (TEWL), decreased skin hydration, and loss of elasticity. Disclosed herein is a description of a safe, flowable, polymer emulsion system that can be activated to form an invisible, breathable, elastic, cosmetically elegant occlusive film that can be comfortably worn to provide remarkable skin hydration and aesthetic benefits. An additional benefit is that the film durability does not require repeated applications to sustain such benefits.

In addition to providing increased compliance with a once-daily application of aesthetically elegant formulations, patients benefit from the immediate cosmetic results, whether during the treatment of a dermatological disorder or following skin ablative and non-ablative procedures that would otherwise require additional downtime. The compositions, formulations, and methods described herein provide a more attractive alternative to current treatment options for dermatological disorders or for management of post-laser or light or chemical peel treatment recovery. First, the film formed is two times more hydrating than petrolatum (see Example 2, below). Second, the film formed is more aesthetically pleasing in that it is invisible and takes on the appearance of natural skin. Additionally the skin surface altering properties provide immediate improvements to the appearance of wrinkles, fine lines, skin roughness, redness and periorbital puffiness. Thirdly, the film formed is durable and can be worn over a period of 24 hours without the need to reapply.

In some aspects, the invention provides a composition for treating a dermatological disorder in a subject's skin, in which the composition comprises a) a reactive reinforcing component; and b) a cross-linking component; wherein the cross-linking component catalyzes an in situ cross-linking of the reactive reinforcing component, such that a film is form on the skin.

In some aspects, the invention provides a composition for treating a dermatological disorder in a subject in need thereof, in which the composition comprises a) a reactive reinforcing component; and b) a cross-linking component; wherein the cross-linking component facilitates in situ cross-linking of the reactive reinforcing component, such that a film is formed on skin.

In some aspects, the invention provides a method for treating a dermatological disorder comprising applying to the subject's skin a formulation comprising a) a reactive reinforcing component; and b) a cross-linking component; wherein said cross-linking component catalyzes an in situ cross-linking of the reactive reinforcing component, such that a film is formed on the subject's skin, thereby treating the dermatological disorder.

In some aspects, the invention provides a method for treating one or more dermatological disorder in a subject in need thereof, comprising: applying to the subject a composition comprising a) a reactive reinforcing component; and b) a cross-linking component; in which the cross-linking component facilitates in situ cross-linking of the reactive reinforcing component, such that a film is formed on skin, thereby treating the dermatological disorder.

In some aspects, the invention provides a composition for treating a subject post laser or light or chemical peel treatment, in which the composition comprises a) a reactive reinforcing component; and b) a cross-linking component; wherein the cross-linking component facilitates in situ cross-linking of the reactive reinforcing component, such that a film is formed on skin.

In some aspects, the invention provides a method for treating a subject post-laser or light or chemical peel treatment comprising applying to the subject a formulation comprising a) a reactive reinforcing component; and b) a cross-linking component; wherein said cross-linking component facilitates in situ cross-linking of the reactive reinforcing component, such that a film is formed on skin, thereby treating the subject post-laser or light or chemical peel treatment.

In one embodiment of the invention, the compositions, formulations or films of the invention treat a subject post-laser or light or chemical peel treatment, in addition to masking, concealing, or covering the laser or light treatment area.

The term "subject" includes subjects in which the compositions disclosed herein would be appropriate for use. In one embodiment, the subject is a mammal, for example, a human. In some embodiments, the subject is suffering from a dermatological disorder or has undergone at least one laser or light-treatment or chemical peel procedure.

The language "dermatological disorder" includes disorders that cause at least one symptom on the skin of a subject requiring medical treatment. In one embodiment, dermatological disorders are caused by autoimmune disorders. In another embodiment, a dermatological disorder is caused by environmental factors, such as allergens or chemicals. Examples of symptoms of dermatological disorders requiring treatment is dermatitis, itchy skin, dry skin, crusting, blistering, or cracking skin, skin edema, or skin lesion formation. Dermatological disorders include, but are not limited to, lichen simplex chronicus, cutaneous lupus (e.g., acute cutaneous lupus, subacute cutaneous lupus, chronic cutaneous lupus, chilblain lupus erythematosus, discoid lupus erythematosus, lupus erythematosus-lichen planus overlap syndrome, lupus erythematosus panniculitis, tumid lupus erythematosus and verrucous lupus erythematosus), psoriasis (e.g., psoriasis *vulgaris*, psoriatic erythroderma, pustular psoriasis, drug-induced psoriasis, inverse psoriasis, seborrheic-like psoriasis and guttate psoriasis), eczema (e.g., atopic eczema, atopic dermatitis, contact dermatitis, xerotic eczema, seborrhoeic dermatitis, dyshidrosis, discoid eczema, venous eczema, dermatitis herpetiformis, neurodermatitis and auto-eczematization), or chronic dry skin. In at least one embodiment, the dermatological disorder is lichen simplex chronicus, cutaneous lupus, psoriasis, eczema, or chronic dry skin. In a specific embodiment, the dermatological disorder is psoriasis. In addition, dermatological disorders also include ichthyosis, rosacea and xeroderma. In a specific embodiment, the dermatological disorder is xeroderma, eczema, psoriasis, rosacea and ichthyosis. In a particular embodiment, the dermatological disorder is xeroderma, atopic dermatitis, psoriasis, and ichthyosis. In a particular embodiment, the dermatological disorder is an ulcer.

In at least one embodiment, a subject is suffering from a single dermatological disorder disclosed herein. In an alternative embodiment, the subject is suffering from one or more dermatological disorders listed herein.

Eczema is inflammation of the upper layers of the skin, causing itching, blisters, redness, swelling, and sometimes oozing, scabbing and scaling. As used herein "eczema" and "dermatitis" are used interchangeably. Specifically, the particular eczema disorder is selected from the group consisting of atopic eczema, atopic dermatitis, contact dermatitis, xerotic eczema, seborrhoeic dermatitis, dyshidrosis, discoid eczema, venous eczema, dermatitis herpetiformis, neurodermatitis and autoeczematization.

Atopic dermatitis or atopic eczema is an inflammatory, chronically relapsing, non-contagious and pruritic skin disorder. The skin of a subject with atopic dermatitis reacts abnormally and easily to irritants, food, and environmental allergens and becomes red, flaky and very itchy. It also becomes vulnerable to surface infections caused by bacteria. Atopic dermatitis often occurs together with other atopic diseases like hay fever, asthma and allergic conjunctivitis. It is a familial and chronic disease and its symptoms can increase or disappear over time.

Contact dermatitis is skin inflammation caused by direct contact with a particular substance, such as an allergen (for example, poison ivy or nickel), or an irritant (for example, a detergent, such as sodium lauryl sulfate). A substance may act both as allergen and irritant. Other substances cause a problem after sunlight exposure, bringing on phototoxic dermatitis. Generally, the site of inflammation is itchy, and is confined to a specific area of the body, with the area having defined boundaries.

Xerotic eczema (also known as asteatotic eczema, eczema craquele or craquelatum, winter itch, or pruritus hiemalis) is very dry skin, usually with fine fissures and cracks traversing through the eczematous plaques.

Seborrheic dermatitis (or seborrheic eczema) is a chronic inflammation of unknown cause that causes scales on the skin (often the scalp or face), and include, for example, dandruff and cradle cap.

Dyshidrosis (also known as dyshidrotic eczema, pompholyx, vesicular palmoplantar dermatitis, or housewife's eczema) is a chronic dermatitis characterized by itchy blisters on the palms of the hand, sides of the fingers or toes, and/or soles of the feet.

Discoid eczema (also known as nummular eczema, exudative eczema, microbial eczema) is characterized by round spots with tiny blisters, scabs and scales.

Venous eczema (also known as gravitational eczema, stasis dermatitis, varicose eczema) occurs in people with impaired circulation, such as varicose veins and edema, and is characterized by redness, scaling, darkening of the skin and itching.

Dermatitis herpetiformis (also known as Duhring's Disease) is characterized by intensely itchy and typically symmetrical rash on arms, thighs, knees, and back and is related to celiac disease.

Neurodermatitis (also known as lichen simplex chronicus, localized scratch dermatitis) is an itchy area of thickened, pigmented eczema patch that results from habitual rubbing and scratching.

Autoeczematization is an eczematous reaction to an infection with parasites, fungi, bacteria or viruses.

Retinoid-induced dermatitis occurs in subjects treated with retinoids.

Psoriasis is a chronic, autoimmune disease that appears on the skin. Specific types of psoriasis include psoriasis *vulgaris*, psoriatic erythroderma, pustular psoriasis, inverse psoriasis, and guttate psoriasis. The causes of psoriasis are not known, though certain psoriasis triggers have been established, including certain medications. Such medications may trigger one or more of the specific types of psoriasis described below. Drug-induced psoriasis may be induced by beta-blockers, lithium, antimalarials, terbinafine, calcium channel blockers, Inderal, Quinidine, Indomethacin, captopril, glyburide, granulocyte colony-stimulating factor, interleukins, interferons, and lipid-lowering drugs.

Psoriasis *vulgaris* (also known as plaque psoriasis) is characterized by one or more raised, inflamed, red lesions covered by a silvery white scale.

Psoriatic erythroderma is characterized by periodic, widespread, fiery redness of the skin and the shedding of scales in sheets, rather than smaller flakes. The reddening and shedding of the skin are often accompanied by severe itching and pain, heart rate increase, and fluctuating body temperature.

Pustular psoriasis is characterized by white blisters of non-infectious pus (consisting of white blood cells) surrounded by red skin. Pustular psoriasis includes von Zumbusch, Palmoplantar and Acropustulosis psoriasis.

Inverse psoriasis appears as bright-red lesions that are smooth and shiny and is often found in the armpits, groin, under the breasts, and in other skin folds around the genitals and the buttocks.

Guttate psoriasis appears as small, red, individual spots on the skin, usually appear on the trunk and limbs. Spots associated with guttate psoriasis are not usually as thick as plaque lesions.

In at least one embodiment, a subject suffering from psoriasis may also suffer from a dermatitis listed herein. For example, seborrheic-like psoriasis is a skin condition characterized by psoriasis with an overlapping seborrheic dermatitis.

Ichthyosis is a family of genetic skin disorders characterized by dry, scaling skin that may be thickened or very thin. Specific types of of icthyosis include Ichthyosis *vulgaris*; X-linked ichthyosis; Congenital ichthyosiform erythroderma, Nonbullous (nbCIE); Epidermolytic hyperkeratosis (bullous ichthyosis, bCIE); Harlequin type ichthyosis; Ichthyosis bullosa of Siemens; Ichthyosis hystrix, Curth-Macklin type; Hystrix-like ichthyosis with deafness; Lamellar ichthyosis, type 1; Lamellar ichthyosis, type 2; Lamellar ichthyosis, type 3; Lamellar ichthyosis, type 4; Lamellar ichthyosis, type 5; CHILD Syndrome; Conradi-Hünermann syndrome; Ichthyosis follicularis with alopecia and photophobia syndrome; Keratitis-ichthyosis-deafness syndrome; Netherton syndrome; Neutral lipid storage disease with ichthyosis; Adult Refsum disease; Ichthyosis and male hypogonadism; Sjögren-Larsson syndrome; Photosensitive trichothiodystrophy (IBIDS syndrome).

Ichthyosis *vulgaris* is characterized by fine, polygonal, flat whitish scales that may be darker on distal extremities.

In addition, ichthyosis includes acquired ichthyosis, which is histologically similar to ichthyosis *vulgaris*, but is not believed to be inherited. Instead, acquired ichthyosis can be a manifestation of systemic disease, and it has been described in association with malignancies, drugs, endocrine and metabolic disease, HIV, infection, and autoimmune conditions.

Xeroderma is characterized by abnormally dry skin and may be a chronic or acute condition.

Specific types of rosacea include erythematotelangiectatic rosacea, papulopustular rosacea, phymatous rosacea, and granulomatous rosacea. Rosacea is characterized by the presence of one or more of the following primary features: flushing (transient erythema); nontransient erythema; papules and pustules; and/or telangiectasia and may include one or more of the following secondary features: burning or stinging, plaque; dry appearance; edema; ocular manifestations; peripheral location; and phymatous changes.

Erythematotelangiectatic rosacea (Subtype 1) is mainly characterized by flushing and persistent central facial erythema. The appearance of telangiectases is common but not essential for a diagnosis of this subtype. Central facial edema, stinging and burning sensations, and roughness or scaling may also be reported. A history of flushing alone is common among patients presenting with erythematotelangiectatic rosacea.

Papulopustular rosacea (subtype 2) is characterized by persistent central facial erythema with transient papules or pustules or both in a central facial distribution. However, papules and pustules also may occur periorificially (that is, they may occur in the perioral, perinasal, or periocular areas). The papulopustular subtype resembles acne *vulgaris*, except that comedones are absent. Rosacea and acne may occur concomitantly, and such patients may have comedones as well as the papules and pustules of rosacea. Burning and stinging sensations may be reported by patients with papulopustular rosacea. This subtype has often been seen after or in combination with subtype 1, including the presence of telangiectases. The telangiectases may be obscured by persistent erythema, papules, or pustules, and tend to become more visible after successful treatment of these masking components.

Phymatous rosacea (Subtype 3) includes thickening skin, irregular surface nodularities, and enlargement. Rhinophyma is the most common presentation, but phymatous rosacea may occur in other locations, including the chin, forehead, cheeks, and ears. Patients with this subtype also may have patulous, expressive follicles in the phymatous area, and telangiectases may be present. This subtype has frequently been observed after or in combination with subtypes 1 or 2, including persistent erythema, telangiectases, papules, and pustules. In the case of rhinophyma, these additional stigmata may be especially pronounced in the nasal area.

Granulomatous rosacea is characterized by hard, yellow, brown, or red cutaneous papules or nodules that may be severe and lead to scarring. These lesions tend to be less inflammatory than papules and pustules and sit upon relatively normal-appearing skin. They can vary in size among patients but are monomorphic in each individual patient, and typically appear on the cheeks and periorificial areas. Granulomatous rosacea may occur in locations other than those in which the phymas are observed. The presence of other rosacea signs is not needed for a diagnosis of the granulomatous rosacea variant.

In at least one embodiment, a dermatological disorder may also include a disease-driven secondary dermatological disorder. A "disease-driven secondary dermatological disorder" refers to a dermatological condition that requires treatment and was caused by or is associated with a non-dermatological disorder. A "non-dermatological disorder" includes disorders not primarily associated with the skin but which may result in, be associated with, or have a secondary manifestation of a skin condition. For example, a non-dermatological disorder includes, for example a disorder of the circulatory system or metabolism of the subject. For example, an ulcer is an example of a disease-driven secondary dermatological disorder. As used herein an ulcer is a sore on the skin or a mucous membrane, accompanied by the disintegration of tissue. Ulcers can result in complete loss of the epidermis and often portions of the dermis and even subcutaneous fat. In at least one embodiment, the subject with the ulcer has a circulatory or a metabolic disorder that inhibits the wound healing process, such as diabetes mellitus. In at least one embodiment, the ulcer is caused by a bacterial, viral or fungal infection; cancer; pressure (e.g. a bedsore); blood disorders; and/or a chronic wound. Examples of ulcers that may be treated with the invention disclosed herein include diabetic foot ulcer; Arterial insufficiency ulcers (also known as "ischemic ulcers"); neuropathic ulcers (also known as "mal perforans"); or vascular ulcers.

In one embodiment of the invention, the compositions, formulations or films of the invention treat the dermatological disorder of the subject, in addition to masking, concealing, or covering the dermatological disorder.

As used herein "compromised skin barrier function or "compromised skin barrier" includes conditions such dermatological disorders and skin following treatment with light or laser treatment or chemical peel treatment. In at least some embodiments, compromised skin barrier conditions do not include wounds.

In at least one embodiment, a dermatological disorder does not include wounds or skin or body imperfections.

In at least one embodiment, the dermatological disorder is not a skin or body imperfection. The language "skin or body imperfections" include those items on a subject's skin that the subject perceives as a blemish or a flaw. Examples of skin imperfections include port wine stain or nevus flammeus (e.g., nevus flammeus nuchae or midline nevus flammeus) melasma, wrinkles, blemishes, acne, moles, scars, tattoos, bruises, skin disfigurements, birth marks, sun damage, age damage, uneven skin tone, sagging skin, skin roughness, hyperpigmentation, enlarged pores, telangiectasia, redness, shine, cellulite, stretch marks or loss of skin elasticity.

In at least one embodiment, the dermatological disorder is not a wound. The language "wounds" includes injuries to the skin wherein the skin is torn, cut or punctured. A wound is a break in the skin. In one embodiment, the wound is caused by skin contact with a foreign object. The break in the skin may cause external bleeding. Wounds include open wounds, for example, abrasions, lacerations, incisions, punctures, avulsions, or amputations. Wounds also include burn wounds. A burn is a type of injury to flesh caused by heat, electricity, chemicals, light, radiation or friction. In at least some embodiments, the compromised skin barrier caused by laser or light or chemical peel treatment is not considered to be a wound.

The term "laser treatment" includes any procedure performed by exposing the subject's skin or body to a laser. The laser treatment may be ablative or non-ablative.

Representative laser treatments include laser therapies for cosmetic uses or for medical uses, and include, for example, skin rejuvenation; skin resurfacing; stretch marks; scar removal; wrinkle removal or reduction; leg vein or artery removal; tattoo removal; removal of stretch marks, removal of sunspots; removal of birthmarks; telangiectasia; rosacea; angiomas; hemangiomas; reticular veins; port wine stains; liposuction; hair removal, removal of precancerous lesions, and skin cancer surgery.

The term "light treatment" means intensive pulsed light therapy.

The term "chemical peels" include treatment of the skin with a glycolic acid, trichloracetic acid or a phenol peel where the upper layers of the viable epidermis are removed.

The term "exposed to a laser" or "exposed to a light" means a laser light or light was shone onto the subject's skin or body.

The term "post-laser treatment" means that the subject has undergone a laser treatment prior to treatment with the compositions, formulations, films and methods described herein.

The term "post-light treatment" means that the subject has undergone a light treatment prior to treatment with the compositions, formulations, films and methods described herein.

The compositions, compositions, formulations or films of the invention may be applied to the subject any point in time after undergoing the laser or light or chemical peel treatment. Any amount of time between the laser or light or chemical peel treatment and the use of the method disclosed herein is contemplated. Specifically, the subject may immediately use the compositions, formulations, films and methods described herein immediately following the laser or light or chemical peel treatment procedure, or any time thereafter. Specifically, the subject may wait 30 minutes, 1 hour; 2, 3, 4, 5, 6, 7, 8, 9, 10, 11, 12, 13, 14, 15, 16, 17, 18, 19, 20, 21, 22, 23, or 24 hours to initiate the methods described herein. In at least one embodiment, the compositions, formulations or films of the invention are applied following eschar or scab formation. One of skill in the art would be able to determine when and for how long the treatment is useful.

The terms "treat," "treatment" and "treating" includes both disorder modifying treatment and symptomatic treatment. In some embodiments, treatment ameliorates or causes a reduction in the severity and/or duration of at least one symptom of the dermatological disorder. In some embodiments, treatment causes a complete recovery from the dermatological disorder. In some embodiments, treatment ameliorates or causes a reduction in the severity and/or duration of at least one symptom of the complications arising from laser or light or chemical peel treatment. In some embodiments, treatment causes a complete recovery from the laser or light or chemical peel treatment procedure.

The terms "apply," "applied" and "application" includes methods of contacting or administering the composition or formulation disclosed herein to a subject's skin or body, such as application by fingers, brush, cotton ball, pad, spray, sponge, cotton swab, roll-on and the like. One of skill in the art can readily determine appropriate methods to apply the compositions disclosed herein. In some embodiments, the composition is applied to the subject's skin at the site of the dermatological disorder (e.g., at about the area of the skin where the dermatological disorder occurs). In some embodiments, the composition is applied to the subject's skin at or around the site of the laser or light or chemical peel treatment (e.g., at about the area of the skin that was laser or light or chemically treated).

In treating a dermatological disorder, one of skill in the art (for example, a medical practitioner such as a physician) would first identify the area on the subject's body affected by the dermatological disorder. A pre-treatment of the area (for example, washing, shaving, or otherwise preparing the area for treatment) may be completed, if necessary. After the optional pretreatment, the reactive reinforcing component and the crosslinking component are applied to the area in need of treatment either sequentially or in combination to form the film over the entire or over a portion of the area in need of treatment, thereby treating the dermatological disorder. The amount of both the reactive reinforcing component and/or the crosslinking component is determined by the size and location of the area to be treated as well as the type of disorder to be treated. The film may be left over the area until the dermatological disorder resolves, or improves, or after a period of time as determined by the skilled practitioner or by the subject suffering from the disorder. The film can be removed by use of the film removing cleanser as described herein. The treatment can be repeated as many times as needed in order to achieve a desired result.

In treating a subject post-laser or light or chemical peel treatment, one of skill in the art (for example, a medical practitioner such as a physician) would first identify the area on the subject's skin or body that was laser or light or chemically treated. A pre-treatment of the area (for example, washing, shaving, or otherwise preparing the area for treatment) may be completed, if necessary. After the optional pretreatment, the reactive reinforcing component and the crosslinking component are applied to the area in need of treatment either sequentially or in combination to form the film over the entire or over a portion of the area in need of treatment, thereby treating the subject post-laser or light or chemical peel treatment. The area treated with the the compositions, formulations, films and methods of the invention may also include area that were not exposed during the laser or light or chemical peel treatment. The amount of both the reactive reinforcing component and/or the crosslinking component is determined by the size and location of the area to be treated and/or the type laser or light or chemical peel treatment used. The film may be left over the area until the effects of the laser or light or chemical peel treatment resolves, or improves, or after a period of time as determined by the skilled practitioner or by the subject. The film can be removed by use of the film removing cleanser as described herein. The treatment can be repeated as many times as needed in order to achieve a desired result.

In certain embodiments, the reactive reinforcing component is first applied to the skin and then a cross-linking component is applied over the reactive reinforcing component. In other embodiments, the cross-linking component is first applied to the skin and then a reactive reinforcing component is applied over the cross-linking component.

The language "therapeutic formulation" or "formulation" includes a composition (or "a therapeutic composition") that, when applied to the body of a subject in need of treatment, form a film (or "therapeutic film") on the body resulting in a therapeutic benefit to the subject. Therapeutic benefits include, but are not limited to, resolution or amelioration of symptoms of a dermatological disorder or a laser or light or chemical treatment.

In one embodiment, the therapeutic formulations include a reactive reinforcing component and a cross-linking component. The language "reactive reinforcing component" includes a component that, when applied to the skin as a first component, is the basis of the film that is formed upon application of the cross-linking component to the reactive reinforcing component. In one embodiment, the reactive reinforcing component includes at least one reactive constituent and at least one reinforcing constituent.

The language "reactive constituent" includes one or more constituents of the reactive reinforcing component that provide the reactive film-forming elements of the formulation. In some embodiments, the reactive constituent includes at least one polysiloxane, polyethylene oxide, polypropylene oxide, polyurea, polyurethane, polyester (including polylactic-co-glycolic acid, polycaprolactone, polylactic acid, polyglycolic acid, and polyhydroxybutyrate, polyamide, or polysulfone. In another embodiment, the reactive constituent is or includes at least one or more compounds of formula I:

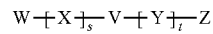

(I)

wherein
W is $R^1R^2R^3SiO-$, $-OR^4$, $-NR^5R^6$, $-CR^7R^8R^9$ or $C_{5-10}$ aryl;

X is —R$^{11}$R$^{12}$Si—O—, —OCONR$^{13}$—, —NR$^{14}$CONR$^{15}$—, —CO—, —NR$^{16}$CO—, —SO$_2$—, —O—, —S— or —NR$^{17}$—;

V is absent, C$_{1-20}$ alkyl, C$_{2-20}$ alkenyl, C$_{5-10}$ aryl, —O—, —NR$^{10}$— or —S—;

Y is —R$^{18}$R$^{19}$Si—O—, —OCONR$^{20}$—, —NR$^{21}$CONR$^{22}$—, —CO—, —NR$^{23}$CO—, —SO$_2$—, —O—, —S— or —NR$^{24}$;

Z is —SiR$^{25}$R$^{26}$R$^{27}$, —OR$^{28}$, —NR$^{29}$R$^{30}$, —CR$^{31}$R$^{32}$R$^{33}$ or C$_{5-10}$ aryl;

R$^1$, R$^2$, R$^3$, R$^7$, R$^8$, R$^9$, R$^{11}$, R$^{12}$, R$^{18}$ R$^{19}$, R$^{25}$, R$^{26}$, R$^{27}$, R$^{31}$, R$^{32}$ and R$^{33}$ are each independently hydrogen, C$_{1-20}$ alkyl, C$_{2-20}$ alkenyl, C$_{5-10}$ aryl, hydroxyl or C$_{1-20}$ alkoxyl;

R$^4$, R$^5$, R$^6$, R$^{13}$, R$^{14}$, R$^{15}$, R$^{16}$, R$^{17}$, R$^{20}$, R$^{21}$, R$^{22}$, R$^{23}$, R$^{24}$, R$^{28}$, R$^{29}$ and R$^{30}$ are each independently hydrogen, C$_{1-20}$ alkyl, C$_{2-20}$ alkenyl, C$_{5-10}$ aryl; and s and t are each independently an integer from about 0 to about 6000.

In some embodiments, the reactive constituent includes more than one compound of formula I and the compounds of formula once may be the same or different.

X and Y of formula I represent an independent "monomer unit." The number of X and Y monomer units present in formula I is provided by the value of s and t, respectively. Representative monomer units include:

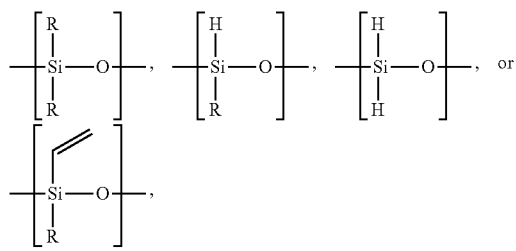

where R is as for defined for R$^1$, R$^2$, R$^3$, etc. above.

It is understood that when more than one X (or Y) monomer unit is present (e.g. s (or t) is more than one), the values for R$^{11}$, R$^{12}$, R$^{13}$, R$^{14}$, R$^{15}$, R$^{16}$, R$^{17}$, R$^{18}$R$^{19}$, R$^{20}$, R$^{21}$, R$^{22}$, R$^{23}$, and R$^{24}$ are selected independently for each individual monomer unit described by —[X]$_s$— (or —[Y]$_t$—). For example, if the value of the monomer unit X is —R$^{11}$R$^{12}$Si—O— and the value of s is 3, then —[X]$_s$— is:

—[R$^{11}$R$^{12}$Si—O—R$^{11}$R$^{12}$Si—O—R$^{11}$R$^{12}$Si—O]—.

In this example, it is understood that the three R$^{11}$ groups present in may be the same or different from each other, for example, one R$^{11}$ may be hydrogen, and the two other R$^{11}$ groups may be methyl.

W and Z of formula I represent independent terminal caps, one on each end of the polymer. For example, terminal caps include:

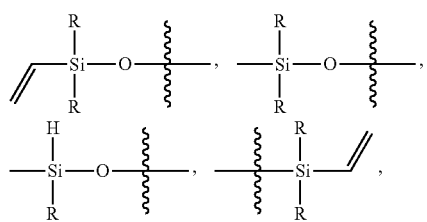

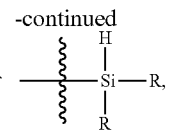

wherein ⸳ denotes attachment to a monomer unit and wherein R is as for defined for R$^1$, R$^2$, R$^3$, etc., above. In one embodiment, W is R$^1$R$^2$R$^3$SiO—, —OR$^4$, —NR$^5$R$^6$, —CR$^7$R$^8$R$^9$ or C$_{5-10}$ aryl;

X is —R$^{11}$R$^{12}$Si—O—, or —NR$^{14}$CONR$^{15}$—;

V is absent, C$_{1-20}$ alkyl, C$_{2-20}$ alkenyl, C$_{5-10}$ aryl, —O—, —NR$^{10}$— or —S—;

Y is —R$^{18}$R$^{19}$Si—O—, or —NR$^{21}$CONR$^{22}$—;

Z is —SiR$^{25}$R$^{26}$R$^{27}$, —OR$^{28}$, —NR$^{29}$R$^{30}$, —CR$^{31}$R$^{32}$R$^{33}$ or C$_{5-10}$ aryl;

R$^1$, R$^2$, R$^3$, R$^7$, R$^8$, R$^9$, R$^{11}$, R$^{12}$, R$^{18}$, R$^{19}$, R$^{25}$, R$^{26}$, R$^{27}$, R$^{31}$, R$^{32}$ and R$^{33}$ are each independently hydrogen, C$_{1-20}$ alkyl, C$_{2-20}$ alkenyl, C$_{5-10}$ aryl, hydroxyl or C$_{1-20}$ alkoxyl;

R$^4$, R$^5$, R$^6$, R$^{14}$, R$^{15}$, R$^{21}$, R$^{22}$, R$^{28}$, R$^{29}$ and R$^{30}$ are each independently hydrogen, C$_{1-20}$ alkyl, C$_{2-20}$ alkenyl, C$_{5-10}$ aryl; and and t are each independently an integer from about 0 to about 6000, wherein the sum of s and t is not 0.

In one embodiment,

W is R$^1$R$^2$R$^3$SiO—, —CR$^7$R$^8$R$^9$ or C$_{5-10}$ aryl;

X is —R$^{11}$R$^{12}$Si—O—, or —NR$^{14}$CONR$^{15}$—;

V is absent, C$_{1-20}$ alkyl, C$_{2-20}$ alkenyl, or C$_{5-10}$ aryl;

Y is —R$^{18}$R$^{19}$Si—O—, or —NR$^{21}$CONR$^{22}$—;

Z is —SiR$^{25}$R$^{26}$R$^{27}$, —CR$^{31}$R$^{32}$R$^{33}$ or C$_{5-10}$ aryl;

R$^1$, R$^2$, R$^3$, R$^7$, R$^8$, R$^9$, R$^{11}$, R$^{12}$, R$^{18}$R$^{19}$, R$^{25}$, R$^{26}$, R$^{27}$, R$^{31}$, R$^{32}$ and R$^{33}$ are each independently hydrogen, C$_{1-20}$ alkyl, C$_{2-20}$ alkenyl, C$_{5-10}$ aryl, hydroxyl or C$_{1-20}$ alkoxyl;

R$^{14}$, R$^{15}$, R$^{21}$, and R$^{22}$ are each independently hydrogen, C$_{1-20}$ alkyl, C$_{2-20}$ alkenyl, C$_{5-10}$ aryl; and s and t are each independently an integer from about 0 to about 6000, wherein the sum of s and t is not 0.

In one embodiment, V is absent, W is R$^1$R$^2$R$^3$SiO—; X is —R$^{11}$R$^{12}$Si—O—; Y is —R$^{18}$R$^{19}$Si—O—; Z is —SiR$^{25}$R$^{26}$R$^{27}$; and R$^1$, R$^2$, R$^3$, R$^{11}$, R$^{12}$, R$^{18}$, R$^{19}$, R$^{25}$, R$^{26}$ and R$^{27}$ are each independently selected from C$_{1-20}$ alkyl (e.g., C$_1$ alkyl, such as methyl) or C$_{2-20}$ alkenyl (e.g., C$_2$ alkenyl, such as vinyl). In one embodiment at least one of R$^1$, R$^2$, R$^3$, R$^{11}$, R$^{12}$, R$^{18}$, R$^{19}$, R$^{25}$, R$^{26}$ and R$^{27}$ is C$_{2-20}$ alkenyl, for example, C$_2$ alkenyl (e.g., vinyl). In another embodiment, at least two of R$^1$, R$^2$, R$^3$, R$^{11}$, R$^{12}$, R$^{18}$, R$^{19}$, R$^{25}$, R$^{26}$ and R$^{27}$ are C$_{2-20}$ alkenyl, for example, C$_2$ alkenyl (e.g., vinyl). In some embodiments, at least one of R$^1$, R$^2$, R$^3$, R$^{25}$, R$^{26}$ and R$^{27}$ are each C$_{2-20}$ alkenyl, for example, C$_2$ alkenyl (e.g., vinyl).

In one embodiment, V is absent, W is R$^1$R$^2$R$^3$SiO—; X is —R$^{11}$R$^{12}$Si—O—; Y is —R$^{18}$R$^{19}$Si—O—; Z is —SiR$^{25}$R$^{26}$R$^{27}$; and R$^1$, R$^2$, R$^3$, R$^{25}$, R$^{26}$ and R$^{27}$ are each independently selected from C$_{1-20}$ alkyl (e.g., C$_1$ alkyl, such as methyl) or C$_{2-20}$ alkenyl (e.g., C$_2$ alkenyl, such as vinyl); and R$^{11}$, R$^{12}$, R$^{18}$, and R$^{19}$ are each independently selected from C$_{1-20}$ alkyl (e.g., C$_1$ alkyl, such as methyl). In one embodiment, at least one of R$^1$, R$^2$, R$^3$, and at least one of R$^{25}$, R$^{26}$ and R$^{27}$ is C$_{2-20}$ alkenyl, for example, C$_2$ alkenyl (e.g., vinyl). In one embodiment, one of R$^1$, R$^2$, R$^3$ is C$_2$ alkenyl (e.g., vinyl) and the others are C$_{1-20}$ alkyl (e.g., C$_1$ alkyl, such as methyl), and at least one of R$^{25}$, R$^{26}$ and R$^{27}$ is C$_{2-20}$ alkenyl, for example, C$_2$ alkenyl (e.g., vinyl) and the others are C$_{1-20}$ alkyl (e.g., C$_1$ alkyl, such as methyl). In one embodiment, at least one of R$^{11}$ or R$^{12}$ and at least one of R$^{18}$ or R$^{19}$ is $C_{2-20}$ alkenyl, for example, $C_2$ alkenyl (e.g., vinyl) for at least one monomer unit. In one embodiment, one of $R^{11}$ or $R^{12}$ is $C_2$ alkenyl (e.g., vinyl) and the others are $C_{1-20}$ alkyl (e.g., $C_1$ alkyl, such as methyl), and at least one of $R^{18}$ or $R^{19}$ is $C_{2-20}$ alkenyl, for example, $C_2$ alkenyl (e.g., vinyl) and the others are $C_{1-20}$ alkyl (e.g., $C_1$ alkyl, such as methyl) for at least one monomer unit.

In some embodiments, the organopolysiloxane includes vinyl moieties only at the terminal caps of the polymer. In some embodiments, the organopolysiloxane is substantially vinyl terminated. In some embodiments, the organopolysiloxane include vinyl moieties only in the monomer units, but not at the terminal cap of the polymer. In other embodiments, the organopolysiloxane includes vinyl moieties at both the terminal cap or in the monomer unit of the polymer. In one embodiment, the polymer includes two vinyl moieties located either at the terminal cap, or within the monomer unit, or a combination thereof. In at least one embodiment, the organopolysiloxane includes vinyl moieties only at the terminal caps of the polymer and contains Si—H units only within the monomer units and not at the terminal caps.

In one embodiment, on average at least two vinyl moieties are present in the polymer. In a specific embodiment, at least two vinyl moieties are present in the polymer and at least two vinyl moieties are present on the two terminal caps of the polymer. In a specific embodiment, only two vinyl moieties are present in the polymer. In a specific embodiment, only two vinyl moieties are present in the polymer and are located on each of the terminal caps. In a specific embodiment, on average at least two vinyl moieties are present in the polymer and at least two vinyl moieties are present in one or more monomer units of the polymer. In a specific embodiment, at least two vinyl moieties are present anywhere in the polymer, but separated from another vinyl moiety by about 2000 monomer units, for example, 1500, 1600, 1700, 1800, 1900, 2000, 2100, 2200, 2300, 2400, or 2500 monomer units. In a specific embodiment, on average at least two vinyl moieties are present anywhere in the polymer, but separated from another vinyl moiety by about 850 monomer units, for example, 350, 450, 550, 650, 750, 850, 950, 1050, 1150, 1250, or 1350 monomer units. In a specific embodiment, on average greater two vinyl moieties are present anywhere in the polymer, but separated from another vinyl moiety by about 40 monomer units, for example, 5, 10, 15, 20, 25, 30, 35, 40, 45, 50, 55, 60, 65, 70, 75, or 80 monomer units. In a specific embodiment, one or more Si—H units are present in addition to the vinyl moiety. Alternatively, in one embodiment, if a vinyl moiety is present then a Si—H is not present.

In one embodiment, V is absent, W is $R^1R^2R^3SiO$—; X is —$R^{11}R^{12}Si$—O—; Y is —$R^{18}R^{19}Si$—O—; Z is —$SiR^{25}R^{26}R^{27}$; $R^1$, $R^2$, $R^3$, $R^{11}$, $R^{12}$, $R^{18}$, $R^{19}$, $R^{25}$, $R^{26}$ and $R^{27}$ are each independently selected from hydrogen or $C_{1-20}$ alkyl (e.g., $C_1$ alkyl, such as methyl). In one embodiment, $R^1$, $R^2$, $R^3$, $R^{25}$, $R^{26}$ and $R^{27}$ are each independently selected from $C_{1-20}$ alkyl (e.g., $C_1$ alkyl, such as methyl); and $R^{11}$, $R^{12}$, $R^{18}$, and $R^{19}$ are each independently selected from hydrogen or $C_{1-20}$ alkyl (e.g., $C_1$ alkyl, such as methyl), wherein at least one of $R^{11}$, $R^{12}$, $R^{18}$, and $R^{19}$ are hydrogen for at least one monomer unit. In one embodiment, on average greater than two Si—H units (e.g. one or more of $R^{11}$, $R^{12}$, $R^{18}$ and $R^{19}$ is hydrogen) are present in the polymer, for example 3-15 Si—H units may be present. In a specific embodiment, 8 Si—H units are present on average. In one embodiment, one or more Si—H units (e.g. one or more of $R^{11}$, $R^{12}$, $R^{18}$, and $R^{19}$ is hydrogen) are present in the polymer. In one embodiment, at least two monomer units on average include a —Si—H unit (e.g. one or more of $R^{11}$, $R^{12}$, $R^{18}$, more of $R^{19}$ and $R^{19}$ is hydrogen). In one embodiment, at least three monomer units on average include a —Si—H unit (e.g. one or more of $R^{11}$, $R^{12}$, $R^{18}$, and $R^{19}$ is hydrogen). In one embodiment, at least four monomer units on average include a —Si—H unit (e.g. one or more of $R^{11}$, $R^{12}$, $R^{18}$, and $R^{19}$ is hydrogen). In one embodiment, at least five monomer units on average include a —Si—H unit (e.g. one or more of $R^{11}$, $R^{12}$, $R^{18}$, and $R^{19}$ is hydrogen). In one embodiment, at least six monomer units on average include a —Si—H unit (e.g. one or more of $R^{11}$, $R^{12}$, $R^{18}$, and $R^{19}$ is hydrogen). In one embodiment, at least seven monomer units on average include a —Si—H unit (e.g. one or more of $R^{11}$, $R^{12}$, $R^{18}$, and $R^{19}$ is hydrogen). In one embodiment, at least eight monomer units on average include a —Si—H unit (e.g. one or more of $R^{11}$, $R^{12}$, $R^{18}$, and $R^{19}$ is hydrogen). In one embodiment, a Si—H unit may be present in one or both the terminal caps in addition to being present in a monomer unit as described above. In one embodiment, one or more Si—H units may be present only in a monomer unit as described above, and not present in either of the terminal caps. In a specific embodiment, Si-(alkyl) or Si-(vinyl) units may also be present in the polymer. In a specific embodiment, only Si—$CH_3$ and Si—H units are present. In a specific embodiment, monomer units or terminal caps include $C_1$-$C_{20}$alkyl, specifically methyl groups, for the non —Si—H positions of the polymer.

In a specific embodiment, on average at least two Si—H units are present in the polymer. In a specific embodiment, on average at least two Si—H moieties are present anywhere in the polymer, but separated from another Si—H moiety by about 2000 monomer units, for example, 1500, 1600, 1700, 1800, 1900, 2000, 2100, 2200, 2300, 2400, or 2500 monomer units. In a specific embodiment, on average at least two Si—H moieties are present only in the monomer units of the polymer and not the terminal cap, and are separated from another Si—H moiety by about 2000 monomer units, for example, 1500, 1600, 1700, 1800, 1900, 2000, 2100, 2200, 2300, 2400, or 2500 monomer units. In a specific embodiment, on average at least two Si—H units are present anywhere in the polymer, but separated from another Si—H moiety by about 850 monomer units, for example, 350, 450, 550, 650, 750, 800, 850, 950, 1050, 1150, 1250, or 1350 monomer units. In a specific embodiment, on average at least two Si—H moieties are present only in the monomer units of the polymer and not the terminal caps, and are separated from another Si—H moiety by about 2000 monomer units, for example, 350, 450, 550, 650, 750, 800, 850, 950, 1050, 1150, 1250, or 1350 monomer units. In a specific embodiment, on average greater than two Si—H units are present anywhere in the polymer, but separated from another Si—H moiety by about 40 monomer units, for example, 5, 10, 15, 20, 25, 30, 35, 40, 45, 50, 55, 60, 65, 70, 75, or 80 monomer units. In a specific embodiment, on average at least two Si—H moieties are present only in the monomer units of the polymer and not the terminal caps, and are separated from another Si—H moiety by about 2000 monomer units, for example, 5, 10, 15, 20, 25, 30, 35, 40, 45, 50, 55, 60, 65, 70, 75, or 80 monomer units.

In one aspect of any one of the above embodiments, the sum of s and t is an integer from about 1000 to about 8000; from about 1300 to about 2700; from about 1500 to about 2700; from about 1600 to about 2600; from about 1600 to about 2500; from about 1700 to about 2500; from about 1800 to about 2400; from about 1800 to about 2300; from about 1900 to about 2300; from about 2000 to about 2200; from about 2050 to about 2150; from about 2100.

In one aspect of any one of the above embodiments, the sum of s and t is an integer from about 200 to about 1100; from about 600 to about 1100; from about 700 to about 1000; from about 800 to about 900; from about 825 to about 875; from about 850; from about 200 to about 800; from about 225 to about 700; from about 250 to about 600; from about 275 to about 500; from about 300 to about 400; from about 350 to about 400; from about 375. In a specific embodiment, the sum of s and t is an integer from about 850.

In one aspect of any one of the above embodiments, the sum of s and t is an integer from about 5 to about 1300; from about 10 to about 1100; from about 10 to about 600; from about 15 to about 500; from about 15 to about 400; from about 20 to about 300; from about 20 to about 200; from about 25 to about 100; from about 25 to about 75; from about 30 to about 50; from about 40.

In some embodiments, the reactive constituent comprises at least one organopolysiloxane. The term "organopolysiloxane" includes compounds of formula II:

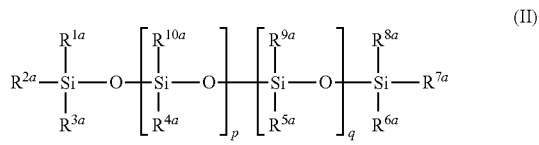

(II)

wherein $R^{1a}$, $R^{2a}$, $R^{3a}$, $R^{4a}$, $R^{5a}$, $R^{6a}$, $R^{7a}$, $R^{8a}$, $R^{9a}$ and $R^{10a}$ are each independently selected from hydrogen, $C_{1-20}$ alkyl, $C_{2-20}$ alkenyl, $C_{5-10}$ aryl, hydroxyl or $C_{1-20}$ alkoxyl and p and q are each independently an integer from between 10 and about 6000.

In some embodiments, the organopolysiloxane is a compound of formula IIa:

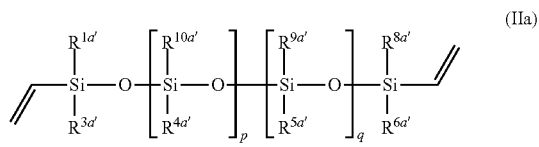

(IIa)

wherein $R^{1a'}$, $R^{3a'}$, $R^{4a'}$, $R^{5a'}$, $R^{6a'}$, $R^{8a'}$, $R^{9a'}$ and $R^{10a'}$ are each independently selected from hydrogen, $C_{1-20}$ alkyl, $C_{2-20}$ alkenyl, $C_{5-10}$ aryl, hydroxyl or $C_{1-20}$ alkoxyl and p and q are each independently an integer from between 10 and about 6000. In one embodiment, $R^{1a}$, $R^{3a'}$, $R^{4a'}$, $R^{5a'}$, $R^{6a'}$, $R^{8a'}$, $R^{9a'}$ and $R^{10a'}$ are alkyl (e.g., $C_1$ alkyl, such as methyl).

The term "alkyl" includes both branched and straight-chain saturated aliphatic hydrocarbon groups having the specified number of carbon atoms. The term "$C_{1-20}$ alkyl" includes branched and straight chain aliphatic groups having between 1 and 20 carbons. Examples of alkyl moieties include methyl, ethyl, n-propyl, i-propyl, n-butyl, s-butyl, t-butyl, n-pentyl, n-hexyl, isopropyl, isobutyl, sec-butyl, tert-butyl, isopentyl, and s-pentyl.

Moreover, the term alkyl includes both "unsubstituted alkyls" and "substituted alkyls," the latter of which refers to alkyl moieties having substituents (e.g., F, Cl, Br, I, $NO_2$, CN, alkyl, aryl, hydroxyl, alkoxy, $COCH_3$ and the like) replacing a hydrogen on one or more carbons of the hydrocarbon backbone.

The term "alkenyl" includes the specified number of hydrocarbon atoms in either straight or branched configuration with one or more unsaturated carbon-carbon bonds that may occur in any stable point along the chain, such as ethenyl and propenyl. The language "$C_{2-20}$ alkenyl" includes branched and straight chain hydrocarbon groups with between 1 and 20 carbons and with one or more unsaturated carbon-carbon bonds. Moreover, the term "alkenyl" includes both "unsubstituted alkenyls" and "substituted alkenyls," the latter of which refers to alkenyl moieties having substituents (e.g., F, Cl, Br, I, $NO_2$, CN, alkyl, aryl, hydroxyl, alkoxy, $COCH_3$ and the like) replacing a hydrogen on one or more carbons of the hydrocarbon backbone.

The term "aryl" includes 5-10 membered monocyclic, bicyclic, or tricyclic rings, wherein at least one ring, if more than one is present, is aromatic. The term "aryl" also includes "heteroaryl" moieties in which one heteroatom (e.g., N, O or S) replaces one or more carbons in the monocyclic, bicyclic, or tricyclic ring. The term "aryl" also includes both "unsubstituted aryls" and "substituted aryls," the latter of which refers to aryl moieties having substituents (e.g., F, Cl, Br, I, $NO_2$, CN, alkyl, hydroxyl, alkoxy, $COCH_3$ and the like) replacing a hydrogen on one or more carbons aromatic ring.

The term "hydroxyl" includes —OH.

The term "alkoxy" includes moieties in which an O is covalently bonded to a $C_{1-20}$ alkyl group, as defined above.

In some embodiments, the organopolysiloxane is vinyl terminated. In some embodiments, the organopolysiloxane is substantially vinyl terminated. The language "vinyl terminated organopolysiloxane" includes organopolysiloxanes that have at least one vinyl group at both terminal ends of the polymer. Specifically, the language "vinyl terminated organopolysiloxane" includes organopolysiloxanes of formula II in which one or both of $R^{2a}$ and $R^{7a}$ are substituted with a $C_2$ alkyl moiety, for example, a vinyl moiety (e.g., —CH=$CH_2$). In a specific embodiment, a "vinyl terminated organopolysiloxane" includes organopolysiloxanes of formula II in which one or both of $R^{2a}$ and $R^{7a}$ are substituted with a $C_2$ alkyl moiety, for example, a vinyl moiety (e.g., —CH=$CH_2$), and $R^{1a}$, $R^{3a}$, $R^{4a}$, $R^{5a}$, $R^{6a}$, $R^{8a}$, $R^{9a}$ and $R^{10a}$ are independently selected from $C_{1-20}$ alkyl, for example, methyl.

In other embodiments, the organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the organopolysiloxane is a high viscosity organopolysiloxane, a low viscosity organopolysiloxane or a combination thereof.

When the organopolysiloxane is a combination of high and low viscosity organopolysiloxanes, the combination of a high viscosity and a low viscosity vinyl organosiloxane provides a bimodal distribution of organosiloxane molecular weights. In at least one embodiment, the organopolysiloxane is a combination of high and low viscosity vinyl-terminal organopolysiloxanes providing a bimodal distribution of the vinyl-terminated organopolysiloxane. In one embodiment, the organopolysiloxane is a combination of formulas I, II, IIa, IIb, and IIc, specifically, of formula IIa, IIb and/or IIc, or more specifically, of formula II and IIc, providing a bimodal distribution of the vinyl-terminated organopolysiloxane. In one embodiment, the bimodal distribution of polymer molecular weight is represented by a ratio of the molecular weights (for example, the sum of s and t) of the high viscosity organopolysiloxanes to the low viscosity organopolysiloxane. In one embodiment, this ratio is from 2 to 3. In a specific embodiment, this ratio is 2.5.

The term "viscosity" refers to the measure of the resistance of a fluid which is being deformed by either shear stress or tensile stress. Viscosity may be reported as either dynamic viscosity, also absolute viscosity, (typical units Pa·s, Poise, P, cP) or kinematic viscosity (typical units $cm^2/s$, Stokes, St, cSt), which is the dynamic viscosity divided by the density. Thus, if and when the density of a fluid is approximately 1, then the dynamic viscosity and the kinematic viscosity are equivalent. One of skill in the art would understand that the density of the fluid may vary with temperature or pressure, and as such would be able to adjust such measurements accordingly. One of skill in the art without undue experimentation would be able to determine how to measure the viscosity of a fluid, for example, using a viscometer or a rheometer. Representative methods include use of a capillary viscometer, rotational viscometer or rheometer to measure viscosity at an instrument specific strain. Specific methods for determining the viscosity of a fluid are shown in Example 5.

The language "high viscosity organopolysiloxane" includes organopolysiloxanes with a viscosity of between about 100,000 and about 500,000 cSt or cP at 25° C., for example, between about 110,000 and about 450,000 cSt or cP at 25° C., between about 120,000 and about 400,000 cSt or cP at 25° C., between about 125,000 and about 350,000 cSt or cP at 25° C., between about 130,000 and about 300,000 cSt or cP at 25° C., between about 135,000 and about 250,000 cSt or cP at 25° C., between about 140,000 and about 200,000 cSt or cP at 25° C., between about 145,000 and about 190,000 cSt or cP at 25° C., between about 150,000 and about 185,000 cSt or cP at 25° C., between about 155,000 and about 175,000 cSt or cP at 25° C., or between about 160,000 and about 170,000 cSt or cP at 25° C. In some embodiments, the viscosity of the high viscosity organopolysiloxane is between about 140,000 and about 200,000 cSt or cP at 25° C. In one embodiment, the high viscosity organopolysiloxane has a viscosity of about 165,000 cSt or cP at 25° C.

In one embodiment, the average molecular weight of the high viscosity organopolysiloxane is between about 100,000 and about 200,000 Da, for example, between about 115,000 and about 195,000 Da, between about 120,000 and about 190,000 Da, between about 125,000 and about 185,000 Da, between about 130,000 and about 180,000 Da, between about 135,000 and about 175,000 Da, between about 140,000 and about 170,000 Da, between about 145,000 and about 165,000 Da or between about 150,000 and about 160,000 Da. In one embodiment, the average molecular weight of the high viscosity organopolysiloxane is about 155,000 Da.

In some embodiments, the high viscosity organopolysiloxane is of formula II, in which $R^{2a}$ and $R^{7a}$ are $C_{2-20}$ alkenyl, for example, $C_2$ alkenyl (e.g., vinyl) and $R^{1a}$, $R^{3a}$, $R^{4a}$, $R^{5a}$, $R^{6a}$, $R^{8a}$, $R^{9a}$ and $R^{10a}$ are each $C_{1-20}$ alkyl, for example, $C_1$ alkyl (e.g., methyl). In some embodiments, the high viscosity organopolysiloxane is vinyl terminated. In other embodiments, the high viscosity organopolysiloxane is vinyl terminated polydimethylsiloxane. In some embodiments, the high viscosity organopolysiloxane is substantially vinyl terminated. In other embodiments, the high viscosity organopolysiloxane is substantially vinyl terminated polydimethylsiloxane.

In some embodiments, the vinyl terminated high viscosity organopolysiloxane has a weight percent of vinyl of between about 0.010 and about 0.100, for example, between about 0.015 and about 0.080, between about 0.020 and about 0.075, between about 0.025 and about 0.060, or between about 0.030 and about 0.050. In one embodiment, the high viscosity organopolysiloxane has a weight percent of vinyl of between about 0.030 and about 0.040.

In other embodiments, the high viscosity organopolysiloxane has a vinyl equivalent per kilogram of between about 0.0100 and about 0.0200, for example, between about 0.0110 and about 0.0190, between about 0.0115 and about 0.0180, between about 0.0120 and about 0.0170, between about 0.0125 and about 0.0165 or between about 0.013 and about 0.016.

In one embodiment, the high viscosity organopolysiloxane has on average at least two vinyl units per high viscosity organopolysiloxane. In one embodiment, the monomer unit including a vinyl moiety are spaced throughout the polymer. In one embodiment, the vinyl-containing monomer unit is spaced about 2000 monomer units away from another vinyl-containing monomer unit or a vinyl-containing terminal cap. For example, the vinyl units in the high viscosity organopolysiloxanes are separated by 1500, 1600, 1700, 1800, 1900, 2000, 2100, 2200, 2300, 2400, or 2500 monomer units.

In some embodiments, the high viscosity organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxane-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

The language "low viscosity organopolysiloxane" includes organopolysiloxanes with a viscosity of between about 500 and about 50,000 cSt or cP at 25° C., for example, between about 1,000 and about 45,000 cSt or cP at 25° C., between about 1,500 and about 40,000 cSt or cP at 25° C., between about 2,000 and about 35,000 cSt or cP at 25° C., between about 2,500 and about 30,000 cSt or cP at 25° C., between about 3,000 and about 25,000 cSt or cP at 25° C., between about 3,500 and about 20,000 cSt or cP at 25° C., between about 4,000 and about 15,000 cSt or cP at 25° C., or between about 4,000 and about 12,000 cSt or cP at 25° C. In some embodiments, the low viscosity organopolysiloxane includes organopolysiloxanes with a viscosity of between about 100 and about 5,000 cSt or cP at 25° C., for example, between about 200 and about 4000 cSt or cP at 25° C., between about 300 and about 3000 cSt or cP at 25° C., between about 400 and about 2000 cSt or cP at 25° C. or between about 750 and about 1500 cSt or cP at 25° C. In one embodiment, the low viscosity organopolysiloxane has a viscosity of about 10,000 cSt or cP at 25° C. In some embodiments, the low viscosity organopolysiloxane has a viscosity of about 1000 cSt or cP at 25° C.

In some embodiments, the low viscosity organopolysiloxane has an average molecular weight of between about 20,000 and about 80,000 Da, for example, between about 50,000 and about 75,000 Da, between about 55,000 and about 70,000 Da, between about 60,000 and about 65,000 Da or between 62,000 and about 63,000 Da. In one embodiment, the low viscosity organopolysiloxane has an average molecular weight of about 62,700 Da. In one embodiment, the low viscosity organopolysiloxane has an average molecular weight of about 28,000 Da.

In some embodiments, the low viscosity organopolysiloxane is of formula II, in which $R^{2a}$ and $R^{7a}$ are $C_{2-20}$ alkenyl, for example, $C_2$ alkenyl (e.g., vinyl) and $R^{1a}$, $R^{3a}$, $R^{4a}$, $R^{5a}$, $R^{6a}$, $R^{8a}$, $R^{9a}$ and $R^{10a}$ are each $C_{1-20}$ alkyl, for example, $C_1$ alkyl (e.g., methyl). In some embodiments, the low viscosity organopolysiloxane is vinyl terminated. In some embodiments, the low viscosity organopolysiloxane is substantially vinyl terminated. In other embodiments, the low viscosity organopolysiloxane is vinyl terminated polydimethylsiloxane. In other embodiments, the low viscosity organopolysiloxane is substantially vinyl terminated polydimethylsiloxane.

In some embodiments, the low viscosity organopolysiloxane has a weight percent of vinyl of between about 0.010 and about 0.30, for example, between about 0.020 and about 0.29, between about 0.030 and about 0.28, between about 0.040 and about 0.27, between about 0.050 and about 0.26, between about 0.060 between about 0.25, between about 0.070 and about 0.24, between about 0.080 and about 0.23, or between about 0.090 and about 0.22. In some embodiments, the low viscosity organopolysiloxane has a weight percent of vinyl of between about 0.18 and about 0.26.

In other embodiments, the low viscosity organopolysiloxane has a vinyl equivalent per kilogram of between about 0.010 and about 0.100, for example, between about 0.015 and about 0.090, between about 0.020 and about 0.080, between about 0.025 and about 0.070, between about 0.030 and about 0.060 or between about 0.040 and about 0.050. In some embodiments, the low viscosity organopolysiloxane has a vinyl equivalent per kilogram of between about 0.030 and about 0.040.

In other embodiments, the low viscosity organopolysiloxane has on average at least two vinyl units per low viscosity organpolysiloxane. In one embodiment, the monomer unit including a vinyl moiety is spaced throughout the polymer. In one embodiment, the vinyl-containing monomer unit is spaced about 850 monomer units away from another vinyl-containing monomer unit or a vinyl-containing terminal cap. For example, the vinyl units in the low viscosity organopolysiloxanes are separated by 450, 550, 650, 750, 800, 850, 950, 1050, 1150, 1250, or 1350 monomer units.

In some embodiments, the low viscosity organopolysiloxane is selected from: vinyl terminated polydimethylsiloxane; vinyl terminated diphenylsiloxane-dimethylsiloxane copolymers; vinyl terminated polyphenylmethylsiloxane, vinylphenylmethyl terminated vinylphenylsiloxane-phenylmethylsiloxane copolymer; vinyl terminated trifluoropropylmethylsiloxane-dimethylsiloxane copolymer; vinyl terminated diethylsiloxne-dimethylsiloxane copolymer; vinylmethylsiloxane-dimethylsiloxane copolymer, trimethylsiloxy terminated; vinylmethylsiloxane-dimethylsiloxane copolymers, silanol terminated; vinylmethylsiloxane-dimethylsiloxane copolymers, vinyl terminated; vinyl gums; vinylmethylsiloxane homopolymers; vinyl T-structure polymers; monovinyl terminated polydimethylsiloxanes; vinylmethylsiloxane terpolymers; vinylmethoxysilane homopolymers and combinations thereof.

In some embodiments, the organopolysiloxane is a compound of formula IIb:

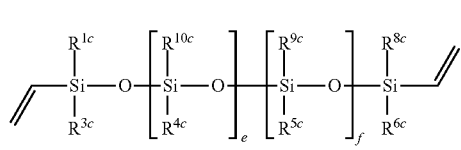

(IIb)

wherein $R^{1c}$, $R^{3c}$, $R^{4c}$, $R^{5c}$, $R^{6c}$, $R^{8c}$, $R^{9c}$ and $R^{10c}$ are each independently selected from hydrogen, $C_{1-20}$ alkyl, $C_{2-20}$ alkenyl, $C_{5-10}$ aryl, hydroxyl or $C_{1-20}$ alkoxyl and e and f are each independently an integer from between 10 and about 6000. In one embodiment, $R^{1c}$, $R^{3c}$, $R^{4c}$, $R^{5c}$, $R^{6c}$, $R^{8c}$, $R^{9c}$ and $R^{10c}$ are alkyl (e.g., $C_1$ alkyl, such as methyl). In some embodiments, the sum of e and f is an integer from about 1000 to about 8000; from about 1300 to about 2700; from about 1500 to about 2700; from about 1600 to about 2600; from about 1600 to about 2500; from about 1700 to about 2500; from about 1800 to about 2400; from about 1800 to about 2300; from about 1900 to about 2300; from about 2000 to about 2200; from about 2050 to about 2150; from about 2100.

In some embodiments, the organopolysiloxane is a compound of formula IIc:

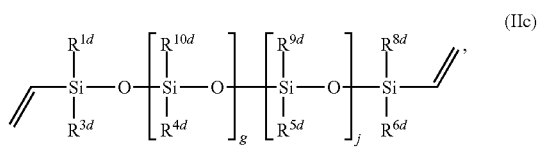

(IIc)

wherein $R^{1d}$, $R^{3d}$, $R^{4d}$, $R^{5d}$, $R^{6d}$, $R^{8d}$, $R^{9d}$ and $R^{10d}$ are each independently selected from hydrogen, $C_{1-20}$ alkyl, $C_{2-20}$ alkenyl, $C_{5-10}$ aryl, hydroxyl or $C_{1-20}$ alkoxyl and g and j are each independently an integer from between 10 and about 6000. In one embodiment, $R^{1d}$, $R^{3d}$, $R^{4d}$, $R^{5d}$, $R^{6d}$, $R^{8d}$, $R^{9d}$ and $R^{10d}$ are alkyl (e.g., $C_1$ alkyl, such as methyl). In some embodiments, the sum of g and j is an integer from about 200 to about 1100; from about 600 to about 1100; from about 700 to about 1000; from about 800 to about 900; from about 825 to about 875; from about 850; from about 200 to about 800; from about 225 to about 700; from about 250 to about 600; from about 275 to about 500; from about 300 to about 400; from about 350 to about 400; from about 375. In some embodiments, the sum of g and j is an integer from about 850.

In some embodiments, the reactive constituent comprises at least one hydride functionalized polysiloxane. The language "hydride functionalized polysiloxane" includes compounds of formula III:

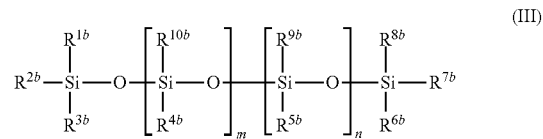

(III)

wherein $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are each independently selected from hydrogen, $C_{1-20}$ alkyl, $C_{2-20}$ alkenyl, $C_{5-10}$ aryl, hydroxyl or $C_{1-20}$ alkoxy and m and n are each independently an integer from between 10 and about 6000, provided that at least one of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ is hydrogen. In some is hydrogen. In some embodiments, at least one of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ is hydrogen and the remainder are $C_{1-20}$ alkyl. In some embodiments, at least two of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., two Si—H units per functionalized hydride polysiloxane molecule). In other embodiments, at least three of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., three Si—H units per functionalized hydride polysiloxane molecule). In some embodiments, at least two of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., two Si—H units per functionalized hydride polysiloxane molecule) and the remainder are $C_{1-20}$ alkyl. In other embodiments, at least three of $R^{1b}$, $R^{2b}$, $R^{3b}$, $R^{4b}$, $R^{5b}$, $R^{6b}$, $R^{7b}$, $R^{8b}$, $R^{9b}$ and $R^{10b}$ are hydrogen (e.g., three Si—H units per functionalized hydride polysiloxane molecule) and the remainder are $C_{1-20}$ alkyl. In some embodiments, at least two of $R^{4b}$, $R^{5b}$, $R^{9b}$ and $R^{10b}$ are hydrogen (e.g., two Si—H units per functionalized hydride polysiloxane molecule) and the remainder are $C_{1-20}$ alkyl. In other embodiments, at least three of $R^{4b}$, $R^{5b}$, $R^{9b}$ and $R^{10b}$ are hydrogen (e.g., three Si—H units per functionalized hydride polysiloxane molecule) and the remainder are $C_{1-20}$ alkyl. In some embodiments, at least two of $R^{4b}$, $R^{5b}$, $R^{9b}$ and $R^{10b}$ are hydrogen (e.g., two Si—H units per functionalized hydride polysiloxane molecule) and the remainder and $R^{1b}$, $R^{2b}$, $R^{3b}$, $R^{6b}$, $R^{7b}$, and $R^{8b}$ are $C_{1-20}$ alkyl. In other embodiments, at least three of $R^{4b}$, $R^{5b}$, $R^{9b}$ and $R^{10b}$ are hydrogen (e.g., three Si—H units per functionalized hydride polysiloxane molecule) and the remainder and $R^{1b}$, $R^{2b}$, $R^{3b}$, $R^{6b}$, $R^{7b}$, and $R^{8b}$ are $C_{1-20}$ alkyl.

In one embodiment, at least greater than two monomer units of formula III include a —Si—H unit (e.g. one or more of $R^{4b}$, $R^{5b}$, $R^{9b}$ and $R^{10b}$ is hydrogen). In one embodiment, at least greater than two monomer units of formula III include a —Si—H unit (e.g. one or more of $R^{4b}$, $R^{5b}$, $R^{9b}$ and $R^{10b}$ is hydrogen) and the remaining non —Si—H monomer units are Si—$CH_3$. For example, on average 2 to 15 monomer units of formula III include a Si—H unit. In one embodiment, at least two monomer units of formula III include a —Si—H unit (e.g. one or more of $R^{4b}$, $R^{5b}$, $R^{9b}$ and $R^{10b}$ is hydrogen). In one embodiment, at least three monomer units of formula III include a —Si—H unit (e.g. one or more of $R^{4b}$, $R^{5b}$, $R^{9b}$ and $R^{10b}$ is hydrogen). In one embodiment, at least four monomer units of formula III include a —Si—H unit (e.g. one or more of $R^{4b}$, $R^{5b}$, $R^{9b}$ and $R^{10b}$ is hydrogen). In one embodiment, at least five monomer units of formula III include a —Si—H unit (e.g. one or more of $R^{4b}$, $R^{5b}$, $R^{9b}$ and $R^{10b}$ is hydrogen). In one embodiment, at least six monomer units of formula III include a —Si—H unit (e.g. one or more of $R^{4b}$, $R^{5b}$, $R^{9b}$ and $R^{10b}$ is hydrogen). In one embodiment, at least seven monomer units of formula III include a —Si—H unit (e.g. one or more of $R^{4b}$, $R^{5b}$, $R^{9b}$ and $R^{10b}$ is hydrogen). In one embodiment, at least eight monomer units of formula III include a —Si—H unit (e.g. one or more of $R^{4b}$, $R^{5b}$, $R^{9b}$ and $R^{10b}$ is hydrogen). In a specific embodiment, the non Si—H positions may include a Si-(alkyl) or Si-(vinyl) unit. In a specific embodiment, the non —Si—H positions are Si—$CH_3$. In some of the embodiments, $R^{1b}$, $R^{2b}$, $R^{3b}$, $R^{6b}$, $R^{7b}$, and $R^{8b}$ are $C_{1-20}$ alkyl. In a specific embodiment, the Si—H positions are not present in the terminal caps. In some embodiments, the compound of formula III is substantially alkyl-terminated. In some embodiments, the compound of formula III is alkyl-terminated. In one embodiment, the Si—H units in the hydride-functionalized organopolysiloxanes are separated by 5, 10, 15, 20, 25, 30, 35, 40, 45, 50, 60, 65, 70, 75, 80, 85, 90, 100, 125, 150, or 200 monomer units.

In one aspect of any one of the above embodiments, the sum of m and n is an integer from about 10 to about 1300; from about 10 to about 1100; from about 10 to about 600; from about 15 to about 500; from about 15 to about 400; from about 20 to about 300; from about 20 to about 200; from about 25 to about 100; from about 25 to about 75; from about 30 to about 50; from about 40.

In some embodiments, the hydride functionalized polysiloxane includes Si—H units only at the terminal caps of the polymer. In some embodiments, the polysiloxane include Si—H units only in the monomer units, but not at the terminal caps of the polymer. In other embodiments, the polysiloxane includes Si—H units at both the terminal cap or in the monomer unit of the polymer. In one embodiment, the polysiloxane includes two to twelve Si—H units on average located either at the terminal cap, or within the monomer unit, or a combination thereof. In one embodiment, the polysiloxane includes four to fifteen Si—H units on average located either at the terminal cap, or within the monomer unit, or a combination thereof. In one embodiment, the polysiloxane includes eight Si—H units on average located either at the terminal cap, or within the monomer unit, or a combination thereof. In one embodiment, the polysiloxane includes two to twelve Si—H units on average located within the monomer unit, and not at the terminal caps. In one embodiment, the polysiloxane includes four to fifteen Si—H units on average located within the monomer unit, and not at the terminal caps. In one embodiment, the polysiloxane includes eight Si—H units on average located within the monomer unit, and not at the terminal caps. In some embodiments, the hydride functionalized polysiloxane is substantially alkyl terminated.

In some embodiments, the hydride functionalized polysiloxane has a viscosity of between about 5 and about 11,000 cSt or cP at 25° C., for example, between about 10 and about 10,000 cSt or cP at 25° C., between about 15 and about 5,000 cSt or cP at 25° C., between about 20 and about 1,000 cSt or cP at 25° C., between about 25 and about 500 cSt or cP at 25° C., between about 30 and about 100 cSt or cP at 25° C., and between about 40 and about 50 cSt or cP at 25° C. In one embodiment, the hydride functionalized polysiloxane has a viscosity of about 45 cSt or cP at 25° C.

In some embodiments, the hydride functionalized polysiloxane has an average molecular weight of between about 900 and about 60,000 Da, for example, between about 1000 and about 50,000 Da, between about 1200 and about 25,000 Da, between about 1400 and about 20,000 Da, between about 1600 and about 15,000 Da, between about 1800 and about 10,000 Da, between about 2000 and about 5000 Da, between about 2200 and about 4000 Da, and between 2300 and about 2500 Da. In one embodiment, the average molecular weight of the hydride functionalized polysiloxane is about 2400 Da.

In some embodiments, the hydride functionalized polysiloxane has a percent SiH content of between about 3 and about 45%, for example, between about 5 and about 40%, between about 10 and about 35%, between about 20 and about 30%, or between about 26 and 27%. In some embodiments, the hydride functionalized polysiloxane has a percent SiH content of about 26%.

In some embodiments, the hydride functionalized polysiloxane has an SiH content of between about 0.500 mmol/g and about 10.00 mmol/g, for example, between about 1.00 mmol/g and about 9.00 mmol/g, between about 2.00 and about 8.00 mmol/g, between about 3.00 mmol/g and about 7.00 mmol/g, and about 4.00 mmol/g and about 6.00 mmol/g. In one embodiment, the hydride functionalized polysiloxane has an SiH content of between about 4.00 and about 5.00 mmol/g, for example, 4.35 mmol/g.

In other embodiments, the hydride functionalized polysiloxane is alkyl terminated. In other embodiments, the hydride functionalized polysiloxane is substantially alkyl terminated. The language "alkyl terminated" includes hydride functionalized polysiloxanes of formula III in which one or both of $R^{2b}$ and $R^{7b}$ are $C_{1-20}$ alkyl. In some embodiments, "alkyl terminated" includes hydride functionalized polysiloxanes of formula III in which one, two, three, four, five or six of $R^{1b}$, $R^{2b}$, $R^{3b}$, $R^{6b}$, $R^{7b}$ and $R^{8b}$ are $C_{1-20}$ alkyl. In one embodiment, $R^{1b}$, $R^{2b}$, $R^{3b}$, $R^{4b}$, $R^{5b}$, $R^{6b}$, $R^{7b}$, $R^{8b}$ and $R^{10b}$ are each $C_{1-20}$ alkyl, for example $C_1$ alkyl (e.g., methyl) and $R^{9b}$ is hydrogen. In one embodiment, $R^{1b}$, $R^{2b}$, $R^{3b}$, $R^{4b}$, $R^{5b}$, $R^{6b}$, $R^{7b}$, $R^{8b}$ and $R^{9b}$ are each $C_{1-20}$ alkyl, for example, $C_1$ alkyl (e.g., methyl) and $R^{10b}$ is hydrogen.

In some embodiments, the hydride functionalized polysiloxane is selected from the group consisting of hydride terminated polydimethylsiloxane; polyphenyl-(dimethylhydrosiloxy)siloxane, hydride terminated; methylhydrosiloxane-phenylmethylsiloxane copolymer, hydride terminated; methylhydrosiloxane-dimethylsiloxane copolymers, trimethylsiloxy terminated; polymethylhydrosiloxanes, trimethylsiloxy terminated; polyethylhydrosiloxane, triethylsiloxane, methylhydrosiloxane-phenyloctylmethylsiloxane copolymer; methylhydrosiloxane-phenyloctylmethylsiloxane terpolymer and combinations thereof.

In some embodiments, the reactive constituent comprises combinations of polymers of formulas I, II, IIa, IIb, IIc, IId, and/or III. In a specific embodiment, the reactive constituent comprises a combination of polymers of formulas IIa, IIb, IIc and/or III. In a specific embodiment, the reactive constituent comprises a combination of polymers of formulas IIb, IIc and III.

In some embodiments, the reactive constituent comprises combinations of high molecular weight vinyl organopolysiloxanes, low molecular weight vinyl organopolysiloxanes, and/or hydride-functionalized organopolysiloxanes. In one embodiment, each of the high and low molecular weight organopolysiloxanes includes on average at least two vinyl moieties per polymer. In a specific embodiment, each vinyl organopolysiloxane includes exactly two vinyl moieties on average. In some embodiments, the reactive constituent comprises one high viscosity organopolysiloxane and one low viscosity organopolysiloxane. In one aspect of this embodiment, the ratio of the viscosity of the high viscosity organopolysiloxane to the viscosity of the low viscosity organopolysiloxane is between 100 and 1, for example, is between 90 and 5; 85 and 10; 80 and 15; 75 and 20; 70 and 25; 65 and 30; 60 and 35; 55 and 40; 50 and 45; 100 and 90; 90 and 80; 80 and 70; 70 and 60; 60 and 50; 50 and 40; 40 and 30; 30 and 20; 20 and 10 and 110 and 1. In some embodiments, the fractional weight of the high viscosity organopolysiloxane to the viscosity of the low viscosity organopolysiloxane is between 0.1 and 0.5, for example, 0.1 to 0.2; 0.2 to 0.3; 0.3 to 0.4; 0.4 to 0.5; 0.15 to 0.45; 0.2 to 0.35; or 0.25 to 0.3. The ratio may be selected in order to adjust the chemical and physical properties of the film in order to suit a specific method or part of the body. In one embodiment, the hydride-functionalized organopolymer includes on average greater than two Si—H units in the polymer. In a specific embodiment, there are 8 Si—H units on average per hydride-functionalized organopolysiloxane.

In some embodiments, the reactive constituent comprises combinations of high molecular weight hydride-functionalized organopolysiloxanes, low molecular weight hydride functionalized organopolysiloxanes, and/or vinyl organopolysiloxanes. In one embodiment, each of the high and low molecular weight organopolysiloxanes include on average at least two Si—H units per polymer. In a specific embodiment, each hydride-functionalized organopolysiloxane includes exactly two Si—H moieties. In one embodiment, the ratio of the high molecular organopolysiloxane to the low molecular weight organopolysiloxane is 2 to 3, for example 2, 2.5 or 3. The ratio may be selected in order to adjust the chemical and physical properties of the film in order to suit a specific method or part of the body. In one embodiment, the vinyl organopolymer includes on average greater than at least two vinyl units in the polymer. In a specific embodiment, there are 8 vinyl units on average per vinyl organopolysiloxane.

The language "reinforcing constituent" includes one or more constituents of the reactive reinforcing component that provide the required physical properties of the film that results from the in situ reaction between the reactive reinforcing component and the cross-linking component. Such physical properties include, for example, mechanical elements (e.g., elasticity, durability, fracture strain, tensile strength, etc. . . . ), biocompatibility (e.g., selective breathability, adhesion, etc. . . . ), optical effects (e.g., reflectance, color, etc. . . . ) and surface modulation (e.g., texture, chemistry, etc. . . . ). Examples of reinforcing constituents include clays, (e.g., $Al_2O_3$, $SiO_2$), chalk, talc, calcite (e.g., $CaCO_3$), mica, barium sulfate, zirconium dioxide, zinc sulfide, zinc oxide, titanium dioxide, aluminum oxide, silica aluminates, calcium silicates, or optionally surface treated silica (e.g., fumed silica, hydrated silica or anhydrous silica). In some embodiments, reinforcing constituent is silica, for example, surface treated silica, such as silica treated with hexamethyldisilazane. In some embodiments, reinforcing constituent is silica, for example, surface treated silica, such as silica treated with hexamethyldisilazane, polydimethylsiloxane, hexdecylsilane or methacrylsilane. In some embodiments, fumed silica has been surface treated with hexamethyldisilazane.

In some embodiments, the reinforcing constituent has a surface area of between about 100 and about 300 $m^2/g$, for example, between about 110 and about 250 $m^2/g$, between about 120 and about 225 $m^2/g$, between about 130 and about 200 $m^2/g$, between about 135 and about 185 $m^2/g$, between about 160 and about 170 $m^2/g$, and between about 164 and about 166 $m^2/g$. In one embodiment, the reinforcing constituent has a surface area of about 160±25 $m^2/g$.

In some embodiments, the reinforcing constituent has an average particle size of between about 1 and about 20 μm. In some embodiments, the fumed silca has an average primary particle size of between about 5 nm and about 20 μm.

In some embodiments, the reinforcing constituent is compounded with the low viscosity and/or the high viscosity organopolysiloxane.

In some embodiments, reactive constituent and reinforcing constituent comprise between about 20 and about 90% of the reactive reinforcing component, for example, between about 40% and about 60% of the reactive reinforcing component. In some embodiments, the reactive constituent and reinforcing constituent comprise between about 45.0 and about 61.0% of the reactive reinforcing component, for example, about 45.0%, about 45.5%, about 46.0%, about 46.5%, about 47.0%, about 47.5%, about 48.5%, about 49.0%, about 49.5%, about 50.0%, about 50.5%, about 51.0%, about 51.5%, about 52.0%, about 52.5%, about 53.0%, about 53.5%, about 54.0%, about 54.5%, about 55.0%, about 55.5%, about 56.0%, about 56.5%, about 57.0%, about 58.0%, about 58.5%, about 59.0%, about 59.5%, about 60.0%, or about 60.5%. In some embodiments, the reactive constituent and the reinforcing constituent comprise about 45% of the reactive reinforcing component. In one embodiment, the reactive constituent and reinforcing constituent comprise about 48.0% of the reactive reinforcing component. In some embodiments, the reactive constituent and the reinforcing constituent comprise about 50.0% of the reactive reinforcing component. In another embodiment, the reactive constituent and reinforcing constituent comprise about 51.0% of the reactive reinforcing component. In some embodiments, the reactive constituent and the reinforcing constituent comprise about 51.5% of the reactive reinforcing component. In another embodiment, the reactive constituent and reinforcing constituent comprise about 54.5% of the reactive reinforcing component. In another embodiment, the reactive constituent and reinforcing constituent comprise about 55.0% of the reactive reinforcing component. In some embodiments, the reactive constituent and the reinforcing constituent comprise about 59.5% of the reactive reinforcing component. In another embodiment, the reactive constituent and reinforcing constituent comprise about 60.5% of the reactive reinforcing component. In some embodiments, the reactive constituent and reinforcing constituent comprise between about 30.0 and about 40.0% of the reactive reinforcing component, for example, about 30.0%, about 30.5%, about 31.0%, about 31.5%, about 32.0%, about 32.5%, about 33.0, about 33.5%, about 34.0%, about 34.5%, about 35.0%, about 35.5%, about 36.0%, about 36.5%, about 37.0%, about 37.5%, about 38.0%, about 38.5%, about 39.0%, about 39.5%, about 40.0%. In some embodiments, the reactive constituent and reinforcing constituent comprise between about 33.0 and about 40.0% of the reactive reinforcing component In one embodiment, the reinforcing constituent comprises between about 8.0 and about 13.0% of the reactive reinforcing component, for example, about 8.5%, about 9.0%, about 9.5%, about 10.0%, about 10.5%, about 11.0%, about 11.5%, about 12.0% or about 12.5%. In one embodiment, the reinforcing constituent comprises between about 1.0 and about 13.0% of the reactive reinforcing component, for example, about 1.0%, about 1.5%; about 2.0%, about 2.5%; about 3.0%, about 3.5%, about 4.0%, about 4.5%, about 5.0%, about 5.5%, about 6.0% or about 6.5%; about 7.0% or about 7.5%; about 8.0%; about 8.5%; about 9.0%, about 9.5%, about 10.0%, about 10.5%, about 11.0%, about 11.5%, about 12.0% or about 12.5%. In some embodiments, the reinforcing constituent comprises about 8.5% of the reactive reinforcing component. In one embodiment, the reinforcing constituent comprises about 9.0% of the reactive reinforcing component. In another embodiment, the reinforcing constituent comprises about 9.5% of the reactive reinforcing component. In some embodiments, the reinforcing constituent comprises about 10.0% of the reactive reinforcing component. In some embodiments, the reinforcing constituent comprises about 10.5% of the reactive reinforcing component. In another embodiment, the reinforcing constituent comprises about 11.0% of the reactive reinforcing component. In another embodiment, the reinforcing constituent comprises about 12.0% of the reactive reinforcing component. In another embodiment, the reinforcing constituent comprises about 13.0% of the reactive reinforcing component.

In another embodiment, the reactive constituent comprises between about 30.0 and about 60.0% of the reactive reinforcing component, for example, about 30.5%, about 31.0%, about 32.0%, about 33.0%, about 34%, about 35.0%, about 36.0%, about 37.0%, about 38.0%, about 39.0%, about 40.0%, about 41.0%, about 42.0%, about 43.0%, about 44.0%, about 45.0%, about 46.0%, about 47.0%, about 48.0%, about 49.0%, about 50.0%, about 51.0%, about 52.0%, about 53.0%, about 54.0%, about 55.0%, about 56.0%, about 57.0%, about 58.0% or about 59.0%.

In some embodiments, the reactive reinforcing component has a viscosity of between about 5,000 and 1,000,000 cSt or cP at 25° C. In some embodiments, the reactive reinforcing component has a viscosity of between about 5,000 and 2,000,000 cSt or cP at 25° C. In some embodiments, the reactive reinforcing component has a viscosity of between about 10,000 and 10,000,000 cSt or cP at 25° C., for example, about 10,000,000, about 9,000,000, about 8,000,000, about 7,000,000, about 6,000,000, about 5,000,000, about 4,000,000, about 3,000,000 or about 2,000,000, about 1,000,000, about 900,000, about 800,000, about 700,000, about 600,000, about 500,000, about 400,000, about 300,000, about 200,000, about 100,000, about 90,000, about 80,000, about 70,000, about 60,000, about 50,000, about 40,000, about 30,000, about 20,000, about 10,000 cSt. In one embodiment, the reactive reinforcing component has a viscosity of about 1,000,000 cSt. The viscosity of the reactive reinforcing component is determined independently from the viscosity of its constituent members.

In some embodiments, the reactive reinforcing component has a vinyl to functional hydride (e.g., —CH═CH$_2$ of the one or more organopolysiloxanes to Si—H of the hydride functionalized polysiloxane) ratio of between about 1:10 and about 1:100, for example, between about 1:15 and about 1:90, between about 1:20 and about 1:80, between about 1:25 and about 1:70, between about 1:30 and about 1:60, between about 1:35 and about 1:50. In one embodiment, the reactive reinforcing component has a vinyl to functional hydride ratio of about 1:40. In another embodiment, the reactive reinforcing component has a vinyl to functional hydride ratio of about 1:20. In some embodiments, the reactive reinforcing component has a vinyl to functional hydride ratio of about 1:15. In some embodiments, the reactive reinforcing component has a vinyl to functional hydride (e.g., —CH═CH$_2$ of the one or more organopolysiloxanes to Si—H of the hydride functionalized polysiloxane) ratio of between about 1:4 and about 1:100.

The language "cross-linking component" includes a component that, when applied to the reactive reinforcing component, catalyzes the in situ formation of the film. Similarly, "cross-linking component" includes a component that, when applied to the reactive reinforcing component, facilitates in situ formation of the film The term "catalyzes the in situ formation of a film" or "facilitates in situ formation of the film" includes causing a reaction to occur between the reactive constituents of the reactive reinforcing component, such that a film is formed on the skin. Without being bound by theory, the cross-linking component induces a reaction between the one or more organopolysiloxanes and the hydride functionalized polysiloxane of the reactive reinforcing component causing the condensation of these constituents, such that a film is formed upon the skin.

In some embodiments, the film formed on skin is a polymerized film. In some embodiments, the polymerized film has a crosslink density at the skin interface that is lower than that at the film surface. In a particular aspect of this embodiment, the ratio of the cross-link density at the skin interface and that at the film surface is between 0.0001 and 0.9, for example, between 0.0001 and 0.1; 0.1 and 0.3; 0.3 and 0.5; and 0.5 and 0.7; 0.7 and 0.9; 0.0010 and 0.8; 0.0020 and 0.7; 0.0030 and 0.6; 0.0040 and 0.6; 0.005 and 0.5; 0.006 and 0.4; 0.007 and 0.3; 0.008 and 0.2; and 0.009 and 0.1.

In some embodiments, the cross-linking component comprises a metal catalyst, for example, a platinum catalyst, a rhodium catalyst or a tin catalyst. Examples of platinum catalysts include, for example, platinum carbonyl cyclovinylmethylsiloxane complexes, platinum divinyltetramethyldisiloxane complexes, platinum cyclovinylmethylsiloxane complexes, platinum octanaldehyde/octanol complexes and combinations thereof. An example of a rhodium catalyst includes Tris (dibutylsulfide) Rhodium trichloride. Examples of tin catalysts include tin II octoate, Tin II neodecanoate, dibutyltin diisooctylmaleate, Di-n-butylbis(2,4 pentanedionate)tin, di-n-butylbutoxychlorotin, dibutyltin dilaurate, dimethyltin dineodecanoate, dimethylhydroxy(oleate)tin and tin II oleate.

In some embodiments, the cross-linking component further comprises a vinyl substituted cyclic or linear organopolysiloxane or a vinyl terminated siloxane. In some embodiments, the amount of vinyl-substituted siloxane or vinyl terminated siloxane is a stabilizing amount of tetramethyltetravinylcyclotetrasiloxane or divinyltetramethyldisiloxane or vinyl terminated siloxane or a combination thereof. The language "stabilizing amount" includes an amount that prevents the degradation of the catalyst and/or the crosslinking component and/or the film. In some embodiments, the stabilizing amount of vinyl-substituted siloxane is less than about 10%, less than about 4%, less than about 3%, less than about 2%, less than about 1%, less than about 0.5% or less than about 0.2%. In some embodiments, the stabilizing amount of vinyl-terminated polysiloxane is about 0.1%. In some embodiments, the stabilizing amount of vinyl-terminated polysiloxane is about 1%.

In some embodiments, the viscosity of the reactive reinforcing component is higher than the viscosity of the crosslinking component. In other embodiments, viscosity of the reactive reinforcing component is lower than the viscosity of the crosslinking component. In yet other embodiments, viscosity of the reactive reinforcing component is similar to the viscosity of the crosslinking component. In a particular embodiment, the viscosity of the reactive reinforcing component is at least 1.5 times greater than the viscosity of the crosslinking component.

In some embodiments, the cross-linking component has a viscosity of between about 1,000 and about 50,000 cSt or cP at 25° C.

In some embodiments, the catalyst is added as a solution and the solution comprises between about 1.0 and about 5.0% of the cross-linking component, for example, about 1.5%, about 2.0%, about 2.5%, about 3.0%, about 3.5%, about 4.0% or about 4.5%. In one embodiment, the catalyst is about 2.0% of the cross-linking component.

In some embodiments, the catalyst comprises between about 0.005 and about 0.04% of the cross-linking component, for example, about 0.005%, about 0.010%, about 0.015%, about 0.020%, about 0.025%, about 0.030% or about 0.035% or about 0.040%. In one embodiment, the catalyst is about 0.02% of the cross-linking component.

In some embodiments, the catalyst is present in the cross-linking component in an amount of between about 100 ppm and about 500 ppm.

In some embodiments, the methods described herein comprise applying to the subject a composition comprising:
 a high viscosity vinyl-terminated dimethylpolysiloxane;
 a low viscosity vinyl-terminated dimethylpolysiloxane;
 alkyl-terminated silicon-hydride polysiloxane; and
 a platinum-divinyltetramethyldisiloxane complex.
In one aspect, the composition may further comprise fumed silica.

In some embodiments, the reactive reinforcing component and the cross-linking component are prevented from coming into contact prior to use. The reactive reinforcing component and the cross-linking component can be kept from coming into contact prior to use by usual means known to one of skill in the art. In one embodiment, the composition is a two part composition in which the reactive reinforcing component and said cross-linking component are packaged in separate containers and mixed prior to use. In another embodiment, the reactive reinforcing component is applied to the skin first, and the cross-linking component is applied on top of the reactive reinforcing component. In yet another embodiment, the cross-linking component is applied to the skin first and the reactive reinforcing component is applied on top of the cross-linking component. In a further embodiment, the reactive reinforcing component and the cross-linking component are packaged together in the same container with a barrier between the two components, and are mixed when the components are extracted from the container.

The term "body" includes any part of the subject's body that can benefit from the formulations disclosed herein. Examples of the subject's body include the skin, the neck, the brow, the jowls, the eyes, the hands, the feet, the face, the cheeks, the breasts, the abdomen, the buttocks, the thighs, the back, the legs, the ankles, cellulite, fat deposits, and the like.

The term "skin" includes the stratum corneum, epidermis and dermis of the subject's skin, which is the outer layer of the skin and includes the stratified squamous epithelium composed of proliferating basal and differentiated suprabasal keratinocytes.

In one embodiment, the composition further comprises one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. In other embodiments, the reactive reinforcing component and/or the cross-linking component further comprise one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. One of skill in the art could readily determine further appropriate additives based on the INCI dictionary, which is incorporated herein by reference in its entirety.

Examples of cosmetic or therapeutic agents include sunscreens (for example, UV protecting agents) anti-aging agents, anti-acne agents, anti-wrinkle agents, spot reducers, moisturizers, anti-oxidants, vitamins.

In some embodiments, the emulsifier is SIMULGEL™.

In some embodiments of the invention, the non-reactive constituents (i.e. the organopolysiloxanes present that are not the vinyl or hydride containing polysiloxanes and the other nonvolatile liquid polymer constituents) comprise less than 5% of the reactive reinforcing component.

In some embodiments, the composition or film is administered first, followed by administration of the one or more additional cosmetic or therapeutic agents. In some embodiments, the composition or film is administered after the one or more additional cosmetic or therapeutic agents. In some embodiments, the film and the one or more additional cosmetic or therapeutic agents are administered substantially at the same time. In some embodiments, the composition or film is used to deliver the one or more additional cosmetic or therapeutic agents.

In some embodiments, a finishing formulation may be applied to the therapeutic formulation during or after formation of the film on the body. The term "finishing formulation" includes a composition comprising components that provide a desired tactile sensation or a desired aesthetic look to the film after formation. For example, the finishing formulation may provide a silky, soft and/or smooth tactile sensation or a dewy, fresh, matte, shiny or luminescent aesthetic look after application to the film.

In some embodiments, the finishing formulation comprises one or more of oils, esters or ethers, for example, triglycerides, PPG-3 benzyl ether myristate, Schercemol DISD ester, or particles, for example, nylon, silica and silicone elastomer beads. In some embodiments, the one or more of these components comprise from about 0.5% to about 100% of the finishing formulation.

In some embodiments, the finishing formulation is a cream, spray, foam, ointment, serum, gel or powder.

In some embodiments, the finishing formulation further comprises one or more feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, dyes (e.g., fluorescent dyes), cosmetic agents or therapeutic agents.

In some embodiments, the films and formulations described herein comprise one or more pigments. These include natural or non-natural coloring agents or dyes. In one embodiment, the pigments are fluorescent dyes.

In some embodiments, the films and formulation further comprise a pigment dispersion formulation. The language "pigment dispersion formulation" includes a formulations that are capable of providing one or more pigments to the films or formulations as a separate component of the formulation or film. In some embodiments, the pigment dispersion formulation allows for an even distribution of the pigment in the films and formulations. In some embodiments, the pigment dispersion formulation comprises at least one reactive constituent. In some embodiments, the pigment dispersion formulation comprises at least one reinforcing constituent. In some embodiments, the pigment dispersion formulation comprises one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents. In other embodiments, the reactive reinforcing component and/or the cross-linking component further comprise one or more of feel modifiers, tack modifiers, spreadability enhancers, diluents, adhesion modifiers, optics modifiers, particles, volatile siloxanes, emulsifiers, emollients, surfactants, thickeners, solvents, film formers, humectants, preservatives, pigments, cosmetic agents or therapeutic agents.

In some embodiments, the pigment dispersion formulation is applied prior to or after the application of the reactive reinforcing component to the skin. In some embodiments, the pigment dispersion formulation is applied prior to or after the application of the cross-linking component to the skin. In some embodiments, the pigment dispersion formulation is applied in between the application of the reactive reinforcing component and the cross-linking component to the skin.

In some embodiments, the pigment dispersion formulation may be applied to skin that has not been subjected to the application of a therapeutic formulation or film. For example, a subject may apply the pigment dispersion formulation to the skin in the area around the therapeutic film or formulation, or the subject may apply the pigment formulation to the skin in lieu of applying the therapeutic film or formulation.

In some embodiments, the invention pertains, at least in part, to a kit comprising a therapeutic formulation comprising a reactive reinforcing component and a cross-linking component. In some embodiments, the kit is a multi-compartment kit comprising at least two compartments in which one compartment comprises the reactive reinforcing component and the second compartment comprises the cross linking component. In some embodiments, the kit further comprises instructions for use of the kit, one or more brushes, one or more swabs, a film removing cleanser or a mirror. In some embodiments, the kit further comprises one or more finishing formulations.

In some embodiments, the invention pertains, at least in part, to a therapeutic film prepared by a process comprising the steps of applying a reactive reinforcing component to the body; and applying a cross-linking component to the reactive reinforcing component, in which the cross-linking component catalyzes an in situ cross-linking of the reactive reinforcing component.

In some embodiments, the invention pertains, at least in part, to a therapeutic film prepared by a process comprising the steps of applying a cross-linking component to the body; and applying a reactive reinforcing component to the cross-linking component, in which the cross-linking component catalyzes an in situ cross-linking of the reactive reinforcing component.

In some embodiments, the film has the appearance of natural skin upon application to the skin. The language "appearance of natural skin" includes the perception that the film, when applied to the skin, has the look, feel and texture of real skin and that the film treated skin has the physical properties (e.g., the elasticity and stiffness) of real (e.g., live) skin. A trained observer and/or a technician would be able to determine whether the film upon application to the body has the appearance of natural skin. For example, a trained observer would be able to determine whether the film, upon application to the body, appears excessively shiny, or whether the film appears not to move with the underlying musculature of the skin by, for example, breaking, buckling or deforming, in response to natural skin motion.

A technician would be able to determine whether the film has the appearance of natural skin upon application to the body. For example, the elasticity and stiffness of skin, with or without the film applied to it, can be assessed by a wide variety of methods (Agache et al., *Arch. Dermatol. Rev.,* 269 (1980) 221), the teachings of which are incorporated herein by reference. For example, the DermaLab suction cup instrument provides one common method to assess the mechanical properties of skin, and has previously shown younger skin to be less stiff and more elastic than aged skin (Grahame et al. *Clinical Science* 39 (1970) 223-238, the teachings of which are incorporated herein by reference). With this method, the stiffness of the skin is indicated by the Young's Modulus, a measure calculated by the instrument based on the pressure required to suck skin up a predetermined distance.

In some embodiments, the Young's Modulus of the skin treated with the film is reduced by between about 5% to about 70%, for example, between about 30% and about 60%, or between about 40% and about 50% compared to untreated skin. In some embodiments, the Young's Modulus of skin treated with the film is reduced by between about 5% and about 25% compared to untreated skin.

The elasticity of the skin is determined by the skin retraction time. The retraction time is obtained by measuring the time it takes for the skin to drop a predetermined distance towards its natural position, after the suction pressure is removed. In some embodiments, the retraction time of skin treated with the film is decreased by between about 5% and about 75%, for example, between about 30% and about 60%, or about 50% and about 65% when compared to untreated skin. In some embodiments, the retraction time of skin treated the film is decreased by between about 5% and about 10% compared to untreated skin. In some embodiments, the retraction time of the skin treated with the film approaches the retraction time of the film alone.

In some embodiments, the film, upon application to the skin, has the appearance and physical properties of youthful, unblemished natural skin. The language "youthful skin" includes skin that has mild or no damage, as measured by the Griffith's score. The Griffith's score (GS), as shown below, is a quantitative measurement of the amount of skin damage subject has.

| | |
|---|---|
| 1. | 0-1: No damage |
| 2. | 2-3: Mild damage |
| 3. | 4-5: Moderate damage |
| 4. | 6-7: Moderate to severe damage |
| 5. | 8-9: Severe damage |

In some embodiments, youthful skin includes skin that has a Griffith's score of between about 0 and about 3.

In some embodiments, the subject's skin has a negative change in Griffith's score (ΔGS) of about 1, about 2, about 3, about 4, about 5, about 6, about 7 or about 8 after application of the film. In some embodiments, the subject's skin has a ΔGS of between about −0.5 and about −3.0 upon application of the film. In one embodiment, the subject's skin has a ΔGS between about −1 and about −1.5, between about −1.2 and about −1.3 (e.g., about −1.25) upon application of the film. In another embodiment, the subject's skin has a ΔGS of between about −2.0 and about −3.0, for example, between about −2.0 and about −2.5, or between about −2.1 and about −2.2 (e.g., about −2.15) upon application of the film.

In other embodiments, the film, upon application to the skin, provides stiffness and elasticity such that the skin treated with the film appear substantially more similar to youthful skin than untreated skin. The term "elasticity" includes the skin's tendency to return to its original shape once it's been deformed. The language "elasticity substantially similar to youthful skin" includes the ability of the skin to return to its original shape once it's been deformed in a manner similar to that of young skin. The term "stiffness" includes the skin's resistance to deformation. The language "stiffness substantially similar to youthful skin" includes the ability of the skin to resist deformation in a manner similar to that of young skin. A technician would also be able to determine whether the film, upon application to the body, has the aforementioned physical properties of youthful, unblemished, natural skin by the techniques described above (e.g., using the Dermalab suction cup instrument).

In some embodiments, the subject and/or observers of the subject perceive an age reduction upon application of the film. In some embodiments, the perceived age reduction is about 1 year, about 2 years, about 3 years, about 4 years, about 5 years, about 6 years, about 7 years, about 8 years, about 9 years, about 10 years, about 11 years, about 12 years, about 13 years, about 14 years or about 15 years less than the subject's actual age. In some embodiments, the perceived age reduction is about 7.5 years less than the subject's actual age upon application of the film. In other embodiments, the perceived age reduction is about 8.5 years less than the subject's actual age upon application of the film.

The language "the film is formed" and "film formation" includes the results of the polymerization reaction that occurs upon the interaction of the reactive reinforcing component and the cross-linking component. Without being bound by theory, film formation is characterized by a phase transition from the viscous sol state of a mixture to that of a continuous interconnected polymer state of film.

A technician could determine when the film is formed on the skin by using routine methods. For example, rheological measurements using small amplitude oscillatory shear can determine the continuous evolution of the viscoelastic properties, such as elastic modulus (G'), the viscous modulus (G") and the loss of tangent (tan δ) of the reacting mixture continuously through the film formation process. In some embodiments, the rheometer can be used to determine the cross over time between G' and G" and the time when tan δ becomes frequency independent, which is a measure of film formation. In some embodiments, the film is formed within at least about five minutes, for example, within about one minute, about two minutes, about three minutes or about four minutes. In some embodiments, the film is formed within at least about 10 seconds and about 3 minutes.

In some embodiments, the film has a Young's Modulus (e.g., tensile strength) of between about 0.01 and about 1 MPa.

In some embodiments, the fracture strain of the film has a fracture strain of at least about 150%.

In some embodiments, the film has a leather adhesive force of greater than about 20 N/mm, for example, greater than about 25 N/mm, greater than about 30 N/mm, greater than about 35 N/mm, greater than about 40 N/mm, greater than about 45 N/mm, greater than about 50 N/mm, greater than about 55 N/mm, greater than about 60 N/mm, greater than about 65 N/mm, greater than about 70 N/mm, greater than about 75 N/mm, or greater than about 80 N/mm. In one embodiment, the leather adhesive force is between about 50 and about 80 N/mm.

In some embodiments, the film has a hysteresis of less than about 10% for example, least than about 9%, less than about 8%, less than about 7%, less than about 6%, less than about 5%, less than about 4%, less than about 3%, less than about 2%, less than 1% or about 0%.

In some embodiments, the film is between about 10 μm and about 1500 μm thick, for example, between about 50 μm and about 500 μm thick. In some embodiments, the film is less than about 100 μm thick. In some embodiments, the film is less than about 75 μm thick. The film thickness may be measured by methods known to one of skill in the art, for example, by the combination of calipers and a calibrated microscope. The thickness of the film may also be digitally measured from a micrograph of the film cross-section. The microscope calibration allows for the conversion of measured pixelar distance into metric distance units.

In some embodiments, the film shrinks by less than between about 1 and 30%, for example, between about 1 to about 15%. The amount of shrinking may be determined by methods known to one of skill in the art, for example, by the Croll method (Croll, S. G. *J. Coatings Tech.* 52 (1980) 35, the teachings of which are incorporated herein by reference). In this method the film is used to coat one side of a thin flexible substrate. The amount of curve developed in the substrate due to the shrinking of the coating is used to calculate the magnitude of shrinking of the coating (Francis et al., *J Mater Sci* 2002; 37:4717-31, the teachings of which are incorporated herein by reference.)

In some embodiments, the film is physiologically stable. The language "physiologically stable" includes the durability of the film upon exposure to normal skin conditions, for example, humidity, tears, sweat or sebum. The physiological stability may be determined by methods typically used by one of ordinary skill in the art, such as an uptake test, which measures the change in weight of the film after exposure to a physiological factor. For example, the uptake test may employ a formulation of simulated sweat (e.g., 1× phosphate buffered saline solution) or simulated sebum (e.g., 25% wax monoesters, 41% triglycerides, 16% free fatty acids and 12% squalene). In some embodiments, the weight of the film increases by less than about 10%, for example, less than about 9%, less than about 8%, less than about 7%, less than about 6%, less than about 5%, less than 4%, less than 3%, less than 2%, less than 1% or exhibits no increase upon exposure to humidity, tears, sweat or sebum.

In some embodiments, the film is used in combination with one or more additional therapeutic agents. In some embodiments, the additional therapeutic agent is a moisturizer, mineral oil, petroleum jelly, coal tar, anthralin, a corticosteroid, fluocinonide, vitamin $D_3$ analogues, retinoids, phototherapy, methotrexate, cyclosporine, a monoclonal antibody, pimecrolimus, tacrolimus, azathioprine, fluoruracil, salicylic acid, benzoyl peroxide, antibiotics or alpha-hydroxy acids. In some embodiments, the film is administered first, followed by administration of the one or more additional therapeutic agents. In some embodiments, the film is administered after the one or more additional therapeutic agents.

In some embodiments, the film and the one or more additional therapeutic agents are administered substantially at the same time. In some embodiments, the film is used to deliver the one or more additional therapeutic agents.

In some embodiments, the film as maintained on the skin for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours.

In some embodiments, the invention provides a kit for use in treating a subject with a dermatological disorder or treating a subject post-laser or light or chemical peel treatment, the kit comprising a) a reactive reinforcing component; b) a cross-linking component; and c) instructions for use. In some embodiments, the kit further comprises one or more additional therapeutic agents. In some embodiments, the kit is a multi-compartment kit comprising at least two compartments. In some embodiments, the reactive reinforcing component is in one compartment and the cross-linking component is in a second compartment. In some embodiments, the kit further comprises one or more brushes, one or more swabs, a film removing cleanser and/or a mirror.

In some embodiments, the invention pertains, at least in part, to a film removing cleanser for use in removing a therapeutic film, wherein said film is prepared by a process comprising the steps of a) applying a reactive reinforcing component to skin; and b) applying a cross-linking component to said reactive reinforcing component, wherein said cross-linking component catalyzes an in situ cross-linking of the reactive reinforcing component.

In other embodiments, the invention pertains, at least in part, to a film removing cleanser comprising a film wetting component, a penetration component, a film swelling component and a film release component.

The language "film removing cleanser" includes a cosmetic formulation that, when applied to a therapeutic film, breaks down the components of the film such that the film may be removed from the body. In some embodiments, the film cleanser removes the film by wetting the film, penetrating the film, swelling the film and releasing the film from the skin.

The language "film wetting component" includes those components of the cleanser that allow the film to absorb liquid. In some embodiments, the film wetting component comprises caprylyl methicone, ethyl trisiloxane or a combination thereof.

The language "penetration component" includes those components of the cleanser that allow the cleanser to permeate the film. Examples of penetration components include siloxane emulsifiers, caprylyl methicone, ethyl trisiloxane or a combination thereof.

The language "film swelling component" includes components of the cleanser which cause the film to expand. Examples of film swelling components include caprylyl methicone, ethyl trisiloxane, isododecane or a combination thereof.

The language "film releasing component" includes components of the cleanser that cause the film to not adhere to the skin or body of the subject to which the film is applied. Examples of film releasing components include glycols, water or a combination thereof.

In some embodiments, the cleanser disrupts the film's mechanical integrity. The language "disrupt the film's mechanical integrity" includes the disturbance of the mechanical features that provide the film its unique properties (e.g., the stiffness, elasticity, elongation, adhesion and the like).

In some embodiments, the cleanser comprises a siloxane phase, an emulsifier phase and an aqueous phase. The language "siloxane phase" includes a component of the cleanser that comprises one or more siloxanes, for example, caprylyl methicone and ethyl trisiloxane. In some embodiments, the siloxane phase also includes isododecane and Aerogel VM2270 (Dow Corning). The language "emulsifier phase" includes a component of the cleanser that comprises one or more emulsifiers, for example, siloxane emulsifiers such as lauryl PEG-9 polydiethylsiloxyethyl dimethicone, PEG-35 Castor oil, or isododecane and lauryl dimethicone/polyglycerin 3 cross polymer. The language "aqueous phase" includes a component of the cleanser that is soluble in water, for example, water, propylene glycol, butylenes diglycol, glycerol or combinations thereof. In some embodiments, the aqueous phase includes MPdiol glycol, preservatives (e.g., neolone PE), optical particles (e.g., silica and DMPA/isophthalic acid/SMDI copolymer & Green 5) and structural particles (e.g., nylon-12).

In some embodiments, the siloxane phase is about 50% of the cleanser, the emulsifier phase is about 8% of the cleanser and the aqueous phase is about 42% of the cleanser.

In some embodiments, the invention pertains, at least in part, to a method of cleaning a body surface having a therapeutic film, comprising applying an effective amount of a film dissolving cleanser to the film, such that said film dissolves. In some embodiments, the body surface is the skin.

In some embodiments, the invention pertains, at least in part, to a formulation for repairing a therapeutic skin applied to the skin in which the formulation comprises a) a reactive reinforcing component and b) a cross-linking component; wherein the cross-linking component catalyzes an in situ cross-linking of the reactive reinforcing component such that a film is formed on the skin.

The terms "repair" and "repairing" includes ameliorating imperfections in the therapeutic film after formation of the film on the skin. In some embodiments, the term "repair" includes mending or patching tears, gaps or breaks in the film. In some embodiments, the term "repair" includes replacing a portion of the film that may have been removed from the skin. In some embodiments, the term "repair" includes re-adhering or re-attaching a portion of the film that may have come loose from the skin (e.g. de-laminated from the skin). In some embodiments, the term "repair" includes swelling the edges of the tear, gap or break in the film to make the film more malleable, such that the film may be able to be reshaped.

In some embodiment, the invention pertains, at least in part, to a method for repairing a therapeutic film applied to skin by a) identifying an area of the film in need of repair; b) optionally smoothing the edges of the film; and c) applying a formulation for repairing the film, wherein the formulation comprises a reactive reinforcing component and a cross-linking component; wherein the cross-linking component catalyzes an in situ cross-linking of the reactive reinforcing component such that a film is formed on the skin, thereby repairing the therapeutic film.

The language "smoothing the edges of the film" includes removing, swabbing, swelling, brushing or grinding the edges of the film in the area in need of repair to remove jagged or uneven portions of the film.

In some embodiments, the invention pertains to a kit comprising a reactive reinforcing component, and a cross-linking component, wherein the cross-linking component catalyzes an in situ cross-linking of the reactive reinforcing component such that a film is formed on the skin. In some embodiments, the invention pertains, at least in part, to a kit for repairing a therapeutic film in which the kit comprises a formulation comprising a) a reactive reinforcing component and b) a cross-linking component wherein the cross-linking component catalyzes an in situ cross-linking of the reactive reinforcing component such that a film is formed on the skin.

In some embodiments, the kit is a multi-compartment kit comprising at least two compartments. In some embodiments, the reactive reinforcing component is in one compartment and the cross-linking component is in a second compartment. In some embodiments, the kit further comprises one or more brushes, one or more swabs, a film removing cleanser, instructions for use or a mirror. In some embodiments, the kit further comprises a pigment dispersion formulation.

Example 1

Formulations

Examples of formulations illustrating the two-step application method are provided below. The reactive reinforcing component first step (e.g., the treatment) includes formulations 60-140-1, 60-140-1B, 60-140-HP2, SK 87/2, 60-140-LX2, SK 87/1, 48-196, 48-199, 60-211, 60-200-1N, 60-208, 66-166-F, 66-167-E, 66-166-C, 66-169-3, 66-170, 79-23, 79-24b, 79-45, 79-46, 79-41, 88-30-1, 83-16, 79-55a, 79-55b, 79-55c, 79-55d, 79-55e, 79-55f, 79-55g, 83-54, 79-55h, 81-18, 81-19, 81-20, 81-21, 79-74, 80-23, 79-88, 79-88-3A, 79-74-RD, 79-90-B, 88-70, 88-72, 88-75-2, 88-75-3, 88-80, 88-85-1, 88-85-2, 88-83-V2, 88-83-V3 and 83-54 shown below.

Components of the formulations are commercially available. The following table provides the generic name for any trade name used throughout this application.

| Tradename | International Nomenclature Cosmetic Ingredient (INCI) name |
|---|---|
| Aerogel VM2270 | Silica Silylate |
| Aerosil 8200 ™ or Aerosil R8200 ™ | Fumed silica modified with hexamethyldisilazane |
| Andisil C1000 ™ | Silicon dioxide + Dimethylpolysiloxane |
| Andisil C1300 ™ | Silicon dioxide + Dimethylpolysiloxane |
| Andisil CE-4 ™ | Vinyl Dimethicone |
| Andisil MV 2,000 ™ or MV2000 | Vinyl Dimethicone |
| Andisil VS 1,000 ™ | Vinyl Dimethicone |
| Andisil VS 10,000 ™ | Vinyl Dimethicone |
| Andisil VS 165,000 ™ or Andisil VS165K | Vinyl Dimethicone |
| Andisil VS 20,000 ™ | Vinyl Dimethicone |
| Andisil VS 250 ™ | Vinyl Dimethicone |
| Andisil VS 500 ™ or VS500 | Vinyl Dimethicone |
| Andisil VS 65,000 ™ or VS65,000 | Vinyl Dimethicone |
| Andisil XL-11 ™ | Hydrogen Dimethicone, SiH Functional |
| Andisil XL-1B ™ or XL-1B | Hydrogen Dimethicone, SiH Functional |
| Aquadispersable Rutile Titanium Dioxide ™ | Titanium dioxide |
| Barium Sulfate HL | Barium Sulfate |
| Beaver UV/Fluorescent Pigment | AROMATIC HETEROCYCLE |
| Cabosperse 1030K | CAB-O-SPERSE ® 1030K is an aqueous dispersion of CAB-O-SIL ® L-90, a very low surface area, fumed silica. It is electrostatically stabilized with Potassium Hydroxide and has an alkaline pH. |
| Carbopol Ultrez 21 | Acrylates/C10-30 Alkyl Acrylate Crosspolymer |
| Cetiol OE | Dicapryl Ether |
| Chronosphere Optical Brite or Chronosphere Opticals/Opticals Brite | Silica and polyurethane-40/silica and polyurethane-40 and green 5 |
| Covacryl MV60 | Sodium Polyacrylate |
| cremaphor EL | PEG-35 Castor Oil |
| Crodamol STS | PPG 3 Benzyl Ether Myristate |
| DC 200 Fluid (1 cSt) | Dimethicone |
| DC 2-1184 fluid (DOW CORNING ® 2-1184 FLUID) | Trisiloxane (and) Dimethicone |
| DC 556 | Phenyl Trimethicone |
| DMF5 CS | dimethicone |
| DMS-V41 | Poly(Dimethylsiloxane), Vinyl Terminated |
| Dow 245 Fluid (Dow CORNING 245 Fluid) | Cyclopentasiloxane |
| Dow 246 Fluid (Dow CORNING 246 Fluid) | Cyclohexasiloxane |
| Dow 9011 Elastomer Blend (Dow Corning 9011 Elastomer Blend) | Cyclopentasiloxane (and) PEG-12 Dimethicone Crosspolymer |
| Dow Corning 9011 Silicone Elastomer Blend ™ or Dow Elastomer Blend 9011 | Cyclopentasiloxane (and) PEG-12 Dimethicone Crosspolymer |
| Dow 9045 Elastomer Blend or Dow Corning 9045 Silicone Elastomer Blend ™ | Cyclopentasiloxane (and) Dimethicone Crosspolymer |
| Dow Corning 200 Fluid 0.65 cSt ™ | Hexamethyldisiloxane |
| Dow Corning 245 Fluid ™ | Decamethylcyclopentasiloxane |
| Dow Corning 5329 | PEG-12 Dimethicone |
| Dow Elastomer Blend 9041 or DOW CORNING ® 9041 SILICONE ELASTOMER BLEND | Dimethicone (and) Dimethicone Crosspolymer |
| dowanol DPM | Dipropylene Glycol Methyl Ether |
| Dri-Flow Elite BN or DRY-FLO Elite BN | Aluminum Starch Octenylsuccinate (and) Boron Nitride |
| Flo-Beads SE-3207B ™ | Ethylene-methyl methacrylate copolymer |
| Dow Corning FZ-3196 | Caprylyl Methicone |
| Ganzpearl GMP-0830 ™ | Acrylates Crosspolymer |
| Granhydrogel O ™ | Water (and) Glyceryl Polyacrylate (and) 1,3-Butylene Glycol (and) PVM/MA (and) Propylparaben (and) Methylparaben |
| Granpowder Nylon ™ | Nylon-12 |
| Gransil EP-LS ™ | Polysilicone-11 (and) Laureth-12 |
| Gransurf 90 | Cetyl PEG/PPG-10/1 Dimethicone |
| Iris | C12-17 Alkanes |
| Iron Oxide Tint or Iron Oxide Tint Mixture | Iron Oxides |
| Isododecane | mixture of highly branched C12 isoparaffins, mainly the 2,2,4,6,6-pentamethylheptane isomer (typically c.a. 85%). |
| Jeechem BUGL ™ or Jeen BUGL | Butylene Glycol |
| Jeecide cap 5 | Phenoxyethanol, Caprylyl Glycol, Potassium Sorbate, Aqua, Hexylene Glycol |
| Jeensilc CPS-312 ™ | Cyclomethicone |

-continued

| Tradename | International Nomenclature Cosmetic Ingredient (INCI) name |
|---|---|
| Kaolin USP BC2747 | Kaolin |
| KF6013 | PEG-9 Dimethicone |
| KTZ Xian Vistas ™ | Titanium Dioxide (And) Mica (And) Iron Oxide (C.I. 77491); chemical name: Mica (and) Titanium Dioxide (and) Ferrous Oxide |
| Labrafac CC ™ | Caprylic/Capric Triglyceride |
| LILAC ™ (Sonneborn) | C14-22 Alkane |
| MPDiol | Methyl Propanediol |
| Neolone PE ™ | Phenoxyethanol, Methylisothiazolinone |
| Nylon | Nylon 12 |
| Nylon 10-I2 ™ | Nylon 12 (And) Isopropyl Titanium Triisostearate |
| PC 075.3 | Hydrogen Dimethicone |
| Permethyl 99A | Isododecane |
| Pink tint mix | Iron Oxides |
| Plantacare 818 UP ™ | Coco-Glucoside; Chemical Description is "C8-16 fatty alcohol glucoside" |
| Platinum divinyl complex (for example PT-50175F) | UPAC name "1,3-Diethenyl-1,1,3,3-tetramethyldisiloxane-platinum (1:1)"; Trade name: "Platinum-divinyltetramethyldisiloxane complex"; Synonyms: Platinum(0)-1,3-divinyl-1,1,3,3-tetramethyldisiloxane complex solution; pt(0)-1,3-divinyl-tetrame-disiloxane compl 0.100; 1,3-Divinyl-1,1,3,3-tetramethyl-disiloxane-platinum (0) |
| Pluracare ® L 64 | Poloxamer 184 (Emulsifier) |
| PMX-1184 or XIAMETER ® PMX-1184 Silicone Fluid | Dimethicone and trisiloxane |
| Polyglycol P425 | PPG-9 |
| prestige pearlescent beige | mixture of titanium and iron oxides of a beige color |
| PS123-KG | Hydrogen Dimethicone |
| RM 2051 or RM 2051 Thickening Agent | Sodium Polyacrylate (and) Dimethicone (and) Cyclopentasiloxane (and) Trideceth-6 (and) PEG/PPG 18/18 |
| Schercemol ™ 318 Ester | Isopropyl Isostearate |
| Sepiplus 400 ™ | Polyacrylate 13 (and) Polyisobutene (and) Polysorbate 20 |
| Shin Etsu KF 6038 | Lauryl PEG-9 Polymethylsiloxyethyl Dimethicone |
| Shin Etsu KSG 820 | Lauryl Dimethicone/Polyglycerin-3 Crosspolymer |
| Silsoft 034 | caprylyl methicone |
| silsoft ETS | ethyl trisiloxane |
| Simulgel EG ™ | Sodium acrylate/acryloyldimethyl taurate copolymer & Isohexadecane & Polysorbate 80 |
| SIMULGEL NS | Hydroxyethylacrylate/sodium acryloyldimethyl taurate copolymer & squalane & polysorbate 60 |
| Soft Bead B or Soft Beads B | Ethylene/Methacrylate Copolymer |
| Solagum AX | Acacia senegal gum and xanthan gum |
| SR 1000 Resin | Trimethylsiloxysilicate |
| Tint | Iron Oxides |
| TMF 1.5 | Methyl Trimethicone |
| Tween 20 | Polysorbate 20 |
| UCT-PS448.5 | Polydimethylsiloxane, Vinyldimethyl Terminated |
| Ultracolor Blue 1% dye | Water and Propylene Glycol and FD & C Blue 1 |
| USG 102 | Dimethicone/Vinyl Dimethicone Crosspolymer |
| Veegum Pro | Tromethamine Magnesium Aluminum Silicate |
| Veegum Ultra Granules | Magnesium Aluminum Silicate |
| Velvesil 125 ™ | Cyclopentasiloxane (and) C30-45 Alkyl Cetearyl Dimethicone Crosspolymer |
| Velvet Veil 310 ™ | Mica (and) Silica |
| Vitamin-A complex | retinol |
| Vitamin-C complex | ascorbic acid |
| Vitamin-E complex | Tocopherol |
| Xirona caribbean blue | Mica, Titanium Dioxide, Silica, Tin Oxide |

Formulation 60-140-1

| Component No. | Component | Percent of Formulation (%) |
|---|---|---|
| 1 | DMS-V41 | 23.80 |
| 2 | Aerosil 8200 | 9.45 |
| 3 | PS123-KG | 12.00 |
| 4 | UCT-PS448.5 | 5.55 |
| 5 | Velvesil 125 | 3.60 |
| 6 | Gransil EP-LS | 3.60 |
| 7 | Soft Beads B | 1.20 |
| 8 | Sepiplus 400 | 1.20 |
| 9 | Water | 27.00 |
| 10 | Granhydrogel O | 6.70 |
| 11 | Granpowder Nylon | 5.90 |

Procedure:

Components 1-4 were hand mixed in a graduated 4-oz until mixture was free of white particulates. Subsequently, components 5-8 were added and the mixture was confirmed as homogenous (Mixture A). In a separate vessel, components 9 and 10 were hand mixed until homogenous (Mixture B). Mixture B was added to Mixture A under strong agitation, provided by a 4-blade, 40 mm propeller at 550 rpm, then component 11 was added and the mixing speed was to 1000 rpm and mix for 5 minutes. The mixture was confirmed as homogenous.

Formulation 60-140-1B

| Component No. | Component | Percent of Formulation (%) |
|---|---|---|
| 1 | DMS-V41 | 22.60 |
| 2 | Aerosil 8200 | 8.94 |
| 3 | PS123-KG | 11.30 |
| 4 | UCT-PS448.5 | 5.30 |
| 5 | Velvesil 125 | 3.42 |
| 6 | Gransil EP-LS | 3.42 |
| 7 | Soft Beads B | 1.20 |
| 8 | Sepiplus 400 | 1.20 |
| 9 | Water | 25.66 |
| 10 | Granhydrogel O | 6.36 |
| 11 | Granpowder Nylon | 5.60 |
| 12 | Cetiol OE | 5.00 |

Procedure:

Components 1-4 were hand mixed in a graduated 4-oz and the mixture was confirmed as free of white particulates. Subsequently, components 5-8 were added and the mixture was confirmed homogenous (Mixture A). In a separate vessel, components 9 and 10 were hand mixed until homogenous (Mixture B). Mixture B to was added Mixture A under strong agitation, provided by a 4-blade, 40 mm propeller at 550 rpm, then components 11 and 12 were added and the mixing speed was increased to 1000 rpm and mix for 5 minutes. The mixture was confirmed as homogenous.

Formulation 60-140-HP2

| Component No. | Component | Percent of Formulation (%) |
|---|---|---|
| 1 | UCT-PS448.5 | 32.97 |
| 2 | Aerosil 8200 | 12.82 |
| 3 | PS123-KG | 14.65 |
| 4 | Velvesil 125 | 4.40 |
| 5 | Gransil EP-LS | 4.40 |
| 6 | Soft Beads B | 1.47 |

-continued

| Component No. | Component | Percent of Formulation (%) |
|---|---|---|
| 7 | Sepiplus 400 | 1.47 |
| 8 | Granhydrogel O | 20.63 |
| 9 | Granpowder Nylon | 7.20 |

Procedure:

Components 1-3 were hand mixed in a graduated 4-oz and the mixture was confirmed as free of white particulates. Subsequently, components 4-7 were added the mixture was confirmed homogenous (Mixture A). In a separate vessel, component 8 was mixed until homogenous (Mixture B). Mixture B to was added Mixture A under strong agitation, provided by a 4-blade, 40 mm propeller at 550 rpm, then component 9 was added and the mixing speed was increased to 1000 rpm and mix for 5 minutes. The mixture was confirmed as homogeneous.

Formulation SK 87/2

| Component No. | Component | Percent of Formulation (%) |
|---|---|---|
| 1 | DMS V41 | 35.00 |
| 2 | Aerosil 8200 | 11.60 |
| 3 | PS123-KG | 5.20 |
| 4 | Velvesil 125 | 11.20 |
| 5 | Gransil EP-LS | 8.70 |
| 6 | Water | 6.70 |
| 7 | Polyvinyl alcohol | 2.00 |
| 8 | Granhydrogel O | 8.70 |
| 9 | Granpowder Nylon | 6.10 |
| 10 | Silsoft 034 | 4.80 |

Procedure:

Components 1-3 were hand mixed in a graduated 4-oz and the mixture was confirmed as free of white particulates. Subsequently, components 4 and 5 were added and the mixture was confirmed as homogenous (Mixture A). In a separate vessel, components 6 and 7 were hand mixed until homogenous (Mixture B). Mixture B was added to Mixture A under strong agitation, provided by a 4-blade, 40 mm propeller at 550 rpm, then components 8-10 were added and the mixing speed was increased to 1000 rpm and mix for 5 minutes. The mixture was confirmed as homogeneous.

Formulation 60-140-LX2

| Component No. | Component | Percent of Formulation (%) |
|---|---|---|
| 1 | DMS V41 | 27.51 |
| 2 | Aerosil 8200 | 10.87 |
| 3 | PS123-KG | 3.47 |
| 4 | UCT-PS448.5 | 13.41 |
| 5 | Velvesil 125 | 4.16 |
| 6 | Gransil EP-LS | 4.16 |
| 7 | Soft Bead B | 1.39 |
| 8 | Sepiplus 400 | 1.39 |
| 9 | Water | 21.45 |
| 10 | Granhydrogel O | 5.38 |
| 11 | Granpowder Nylon | 6.82 |

Procedure:

Components were hand mixed 1-4 in a graduated 4-oz and the mixture was confirmed as free of white particulates. Subsequently, components 5-8 were added and mixture was confirmed as homogenous (Mixture A). In a separate vessel, components 9 and 10 were hand mixed until homogenous (Mixture B). Mixture B was added to Mixture A under strong agitation, provided by a 4-blade, 40 mm propeller at 550 rpm, then component 11 was added and the mixing speed was increased to 1000 rpm and mixed for 5 minutes. The mixture was confirmed as homogeneous.

Formulation SK 87/1

| Component No. | Component | Percent of Formulation (%) |
|---|---|---|
| 1 | DMS V41 | 36.90 |
| 2 | Aerosil 8200 | 12.30 |
| 3 | PS123-KG | 5.50 |
| 4 | Velvesil 125 | 11.60 |
| 5 | Gransil EP-LS | 9.10 |
| 6 | Water | 7.10 |
| 7 | Polyvinyl alcohol | 2.00 |
| 8 | Granhydrogel O | 9.10 |
| 9 | Granpowder Nylon | 6.40 |

Procedure:

Components 1-3 were hand mixed in a graduated 4-oz and the mixture was confirmed as free of white particulates. Subsequently, components 4 and 5 were added and the mixture was confirmed as homogenous (Mixture A). In a separate vessel, components 6 and 7 were hand mixed until homogenous (Mixture B). Mixture B was added to Mixture A under strong agitation, provided by a 4-blade, 40 mm propeller at 550 rpm, then components 8 and 9 were added and the mixing speed was increased to 1000 rpm and mixed for 5 minutes. The mixture was confirmed as homogeneous.

Formulation 48-196

| Component No. | Component | Percent of Formulation (%) |
|---|---|---|
| 1 | Andisil VS10,000 | 24.46 |
| 2 | Andisil VS165K | 3.66 |
| 3 | Aerosil 8200 | 9.72 |
| 4 | Andisil XL-11 | 12.33 |
| 5 | Velvesil 125 | 3.70 |
| 6 | Gransil EP-LS | 3.70 |
| 7 | Soft Beads B | 1.23 |
| 8 | Sepiplus 400 | 1.23 |
| 9 | Water | 27.75 |
| 10 | Granhydrogel O | 6.87 |
| 11 | Neolone PE | 0.21 |
| 12 | Granpowder Nylon | 4.11 |
| 13 | Tint | 1.03 |

Procedure:

Components 1-3 were mixed in a graduated 4-oz with a 4-blade propeller at 1000 RPM until homogenous (Mixture A) and the mixture was confirmed as homogenous. In a separate container components 4-8 were mixed with a 4-blade propeller at 750 RPM until homogenous (Mixture B). In another container, components 9-11 were mixed with a 4-blade propeller at 750 RPM until homogenous (Mixture C). Mixture B was added to Mixture C under strong agitation, provided by a 4-blade, 40 mm propeller at 750 rpm, then Mixture A was added to combined Mixtures B and C drop by drop. Finally, components 12 and 13 were added and the mixing speed increased to 1000 RPM and mix for 10 minutes. The mixture was confirmed as homogeneous.

Formulation 48-199

| Component No. | Component | Percent of Formulation (%) |
|---|---|---|
| 1 | Andisil VS10,000 | 22.11 |
| 2 | Andisil VS165K | 3.31 |
| 3 | Aerosil 8200 | 8.79 |
| 4 | Andisil XL-11 | 11.15 |
| 5 | Velvesil 125 | 3.35 |
| 6 | Gransil EP-LS | 3.35 |
| 7 | Soft Beads B | 1.12 |
| 8 | Sepiplus 400 | 1.12 |
| 9 | Water | 25.09 |
| 10 | Granhydrogel O | 6.21 |
| 11 | Neolone PE | 0.19 |
| 12 | Granpowder Nylon | 4.94 |
| 13 | Silsoft 034 | 9.29 |

Procedure:

Components 1-3 were mixed in a graduated 4-oz with a 4-blade propeller at 1000 RPM until homogenous (Mixture A). In a separate container, components 4-8 were mixed with a 4-blade propeller at 750 RPM until homogenous (Mixture B). In another container, components 9-11 were mixed with a 4-blade propeller at 750 RPM until homogenous (Mixture C). Mixture B to Mixture C was added under strong agitation, provided by a 4-blade, 40 mm propeller at 750 rpm, then Mixture A was added to combined Mixtures B and C drop by drop. Finally, components 12 and 13 were added and the mixing speed was added to 1000 RPM and mixed for 10 minutes. The mixture was confirmed as homogeneous.

Formulation 60-211

| Component No. | Component | Percent of Formulation (%) |
|---|---|---|
| 1 | Andisil C1000 | 33.66 |
| 2 | Andisil C1300 | 6.73 |
| 3 | Andisil XL-11 | 9.62 |
| 4 | Velvesil 125 | 3.46 |
| 5 | Gransil EP-LS | 3.46 |
| 6 | Soft Beads B | 1.15 |
| 7 | Sepiplus 400 | 1.15 |
| 8 | Water | 25.97 |
| 9 | Granhydrogel O | 6.42 |
| 10 | Jeechem BUGL | 3.85 |
| 11 | Neolone PE | 0.19 |
| 12 | Granpowder Nylon | 3.85 |
| 13 | Tint | 0.49 |

Procedure:

Components 1-7 were mixed in a graduated 4-oz with a 4-blade propeller at 2000 RPM until homogenous (Mixture A). In a separate container, components 8-11 were mixed with a 4-blade propeller at 750 RPM until homogenous (Mixture B). Mixture B was slowly added to Mixture A under strong agitation provided by a 4-blade propeller at 2000 RPM. Components 12 and 13 were added and the mixing speed was increased to 2000 RPM for 5 minutes. The mixture was confirmed as homogeneous.

Formulation 60-200-1N

| Component No. | Component | Percent of Formulation (%) |
|---|---|---|
| 1 | Andisil C1000 | 33.88 |
| 2 | Andisil C1300 | 7.65 |
| 3 | Andisil XL-11 | 18.03 |
| 4 | SR 1000 Resin | 10.93 |
| 5 | Iris | 2.19 |
| 6 | Dri-Flow Elite BN | 10.93 |
| 7 | Barium Sulfate HL | 4.37 |
| 8 | Gransil EP-LS | 8.74 |
| 9 | Sepiplus 400 | 2.19 |
| 10 | Neolone PE | 0.55 |
| 11 | Tint | 0.54 |

Procedure:

Components 1-5 were mixed in a graduated 4-oz with a 4-blade propeller at 2000 RPM until homogenous (Mixture A). Components 6-9 were then added and mixed with a 4-blade propeller at 2000 RPM until homogenous. Components 10 and 11 were added and the mixing speed was mixed at 2000 RPM until homogeneous.

Formulation 60-208

| Component No. | Component | Percent of Formulation (%) |
|---|---|---|
| 1 | Andisil C1000 | 30.05 |
| 2 | Andisil C1300 | 6.56 |
| 3 | Andisil XL-11 | 22.95 |
| 4 | SR 1000 Resin | 10.93 |
| 5 | Iris | 2.19 |
| 6 | Dri-Flow Elite BN | 10.93 |
| 7 | Barium Sulfate HL | 4.37 |
| 8 | Gransil EP-LS | 8.74 |
| 9 | Sepiplus 400 | 2.19 |
| 10 | Neolone PE | 0.55 |
| 11 | Tint | 0.54 |

Procedure:

Components 1-5 were mixed in a graduated 4-oz with a 4-blade propeller at 2000 RPM until homogenous (Mixture A). Components 6-9 were then added and mixed with a 4-blade propeller at 2000 RPM until homogenous. Components 10 and 11 were added and the mixing speed was mixed at 2000 RPM until homogeneous.

Formulation 66-166-F

| Component No. | Component | Percent of Formulation (%) |
|---|---|---|
| 1 | Aerosil 8200 ™ | 8.43% |
| 2 | Andisil VS 10,000 ™ | 21.22% |
| 3 | Andisil VS 165,000 ™ | 3.17% |
| 4 | Andisil XL11 ™ | 10.34% |
| 5 | Velvesil 125 ™ | 3.10% |
| 6 | Gransil EP-LS ™ | 3.10% |
| 7 | Flo-Beads SE-3207B ™ | 1.03% |
| 8 | Sepiplus 400 ™ | 1.03% |
| 9 | Water | 23.28% |
| 10 | Granhydrogel O ™ | 5.75% |
| 11 | Neolone PE ™ | 0.17% |
| 12 | Granpowder Nylon ™ | 4.23% |
| 13 | Ganzpearl GMP-0830 ™ | 0.31% |
| 14 | Velvet Veil 310 ™ | 0.21% |
| 15 | Aquadispersable Rutile Titanium Dioxide ™ | 0.21% |
| 16 | Yellow Iron Oxide | 0.09% |
| 17 | Red Iron Oxide | 0.04% |
| 18 | Black Iron Oxide | 0.01% |
| 19 | Dow Corning 200 Fluid 0.65 cSt ™ | 14.29% |

Procedure:

Components 1-3 were mixed together as siloxane phase A. Into siloxane phase B, components 4-8 were mixed. Components 9-11 were combined as the water phase. The water phase was slowly added to siloxane phase B and mixed until homogenous. Into this new phase, phase A was added very slowly drop by drop. Once all of siloxane phase A was added, components 12-19 were added to the formula and mix until homogenous.

Formulation 66-167-E

| Component No. | Component | Percent of Formulation (%) |
|---|---|---|
| 1 | Aerosil 8200 ™ | 8.36% |
| 2 | Andisil VS 10,000 ™ | 21.05% |
| 3 | Andisil VS 165,000 ™ | 3.15% |
| 4 | Andisil XL11 ™ | 10.25% |
| 5 | Velvesil 125 ™ | 3.08% |
| 6 | Gransil EP-LS ™ | 3.08% |
| 7 | Flo-Beads SE-3207B ™ | 1.02% |
| 8 | Sepiplus 400 ™ | 1.02% |
| 9 | Water | 23.09% |
| 10 | Granhydrogel O ™ | 5.70% |
| 11 | Neolone PE ™ | 0.17% |
| 12 | Granpowder Nylon ™ | 4.20% |
| 13 | Ganzpearl GMP-0830 ™ | 0.31% |
| 14 | Velvet Veil 310 ™ | 0.20% |
| 15 | Aquadispersable Rutile Titanium Dioxide ™ | 0.20% |
| 16 | Yellow Iron Oxide | 0.09% |
| 17 | Red Iron Oxide | 0.04% |
| 18 | Black Iron Oxide | 0.01% |
| 19 | LILAC ™ (Sonneborn) | 2% |
| 20 | Cetyl Dimethicone | 5% |
| 21 | Granhydrogel O ™ | 8% |

Procedure:

Components 1-3 were mixed together as siloxane phase A. Into siloxane phase B components 4-8 were added. Components 9-11 were combined as the water phase. The water phase was slowly added to siloxane phase B and mixed until homogenous. Into this new phase, phase A was added very slowly drop by drop. Once all of siloxane phase A was added, components 12-21 were added to the formula and mixed until homogenous.

Formulation 66-166-C

| Component No. | Component | Percent of Formulation (%) |
|---|---|---|
| 1 | Aerosil 8200 ™ | 8.43% |
| 2 | Andisil VS 10,000 ™ | 21.22% |
| 3 | Andisil VS 165,000 ™ | 3.17% |
| 4 | Andisil XL11 ™ | 10.34% |
| 5 | Velvesil 125 ™ | 3.10% |
| 6 | Gransil EP-LS ™ | 3.10% |
| 7 | Flo-Beads SE-3207B ™ | 1.03% |
| 8 | Sepiplus 400 ™ | 1.03% |
| 9 | Water | 23.28% |
| 10 | Granhydrogel O ™ | 5.75% |
| 11 | Neolone PE ™ | 0.17% |
| 12 | Granpowder Nylon ™ | 4.23% |
| 13 | Ganzpearl GMP-0830 ™ | 0.31% |
| 14 | Velvet Veil 310 ™ | 0.21% |
| 15 | Aquadispersable Rutile Titanium Dioxide ™ | 0.21% |
| 16 | Yellow Iron Oxide | 0.09% |
| 17 | Red Iron Oxide | 0.04% |
| 18 | Black Iron Oxide | 0.01% |
| 19 | Granhydrogel O ™ | 14.29% |

Procedure:

Components 1-3 were mixed together as siloxane phase A. Into siloxane phase B components 4-8 were added. Components 9-11 were combined as the water phase. The water phase was slowly added to siloxane phase B and mixed until homogenous. Into this new phase, phase A was very slowly added drop by drop. Once all of siloxane phase A was added, components 12-19 was added to the formula and mixed until homogenous.

Formulation 66-169-3

| Component No. | Component | Percent of Formulation (%) |
|---|---|---|
| 1 | Ganzpearl GMP-0830 ™ | 0.16% |
| 2 | Velvet Veil 310 ™ | 0.10% |
| 3 | Aquadispersable Rutile Titanium Dioxide ™ | 0.10% |
| 4 | Yellow Iron Oxide | 0.04% |
| 5 | Red Iron Oxide | 0.02% |
| 6 | Black Iron Oxide | 0.01% |
| 7 | Gransil EP-LS ™ | 0.76% |
| 8 | Andisil XL-11 ™ | 8.61% |
| 9 | Gransil EP-LS ™ | 2.34% |
| 10 | Andisil C1000 ™ | 33.51% |
| 11 | Andisil C1300 ™ | 6.67% |
| 12 | Andisil XL-11 ™ | 1.59% |
| 13 | Velvesil 125 ™ | 3.48% |
| 14 | Flo-Beads SE-3207B ™ | 1.15% |
| 15 | Sepiplus 400 ™ | 1.27% |
| 16 | Water | 25.18% |
| 17 | Granhydrogel O ™ | 6.22% |
| 18 | Jeechem BUGL ™ | 3.75% |
| 19 | Neolone PE ™ | 0.21% |
| 20 | Granpowder Nylon ™ | 3.83% |
| 21 | KTZ Xian Vistas ™ | 1.00% |

Procedure:

Components 1-8 were mixed together and homogenized at 26,000 RPM for 10 minutes. After 10 minutes, component 9 was added and homogenized again for 10 minutes at 26,000 RPM. To this homogenized mixture, components 10-15 were added and mixed with an overhead stirrer at 2,000 RPM until homogenous in appearance (this is the siloxane phase). In a separate container, components 16-19 were mixed until homogenous to form the water phase. The water phase was added to the siloxane phase very slowly, with continuous stirring at 2,000 RPM. Once the water phase was completely mixed in, components 20 and 21 were added to the formula and mixed at 2,000 RPM until homogenous.

Formulation 66-170

| Component No. | Component | Percent of Formulation (%) |
|---|---|---|
| 1 | Andisil C1300 ™ | 8.92% |
| 2 | Andisil C1000 ™ | 44.21% |
| 3 | Andisil XL-11 ™ | 12.67% |
| 4 | Sepiplus 400 ™ | 1.30% |
| 5 | Ganzpearl GMP-0830 ™ | 0.18% |
| 6 | Velvet Veil 310 ™ | 0.12% |
| 7 | Aquadispersable Rutile Titanium Dioxide ™ | 0.12% |
| 8 | Yellow Iron Oxide | 0.05% |
| 9 | Red Iron Oxide | 0.02% |
| 10 | Black Iron Oxide | 0.01% |

| Component No. | Component | Percent of Formulation (%) |
|---|---|---|
| 11 | Dow Corning 9011 Silicone Elastomer Blend ™ | 3.25% |
| 12 | Dow Corning 9045 Silicone Elastomer Blend ™ | 3.25% |
| 13 | Dow Corning 245 Fluid ™ | 2.62% |
| 14 | Jeensilc CPS-312 ™ | 0.65% |
| 15 | Water | 9.49% |
| 16 | Plantacare 818 UP ™ | 0.16% |
| 17 | Propylene Glycol | 6.60% |
| 18 | Glycerin | 1.29% |
| 19 | Jeechem BUGL ™ | 3.22% |
| 20 | Sodium Chloride | 0.32% |
| 21 | Nylon 10-I2 ™ | 1.53% |

Procedure:

Components 1-10 were mixed together to create the siloxane phase A. Next, components 11-14 were mixed to create siloxane phase B. A water phase was created by mixing components 15-20. The water phase was slowly added into siloxane phase B while mixing at 2,000 RPM to create phase C. Finally, phase C was mixed into siloxane phase A until homogenous.

Formulation 79-23

| Component No. | Component | Percent of Formulation (%) |
|---|---|---|
| 1 | Andisil VS 500 ™ | 0.72 |
| 2 | Andisil MV 2000 ™ | 1.02 |
| 3 | Andisil VS 65,000 ™ | 17.20 |
| 4 | Andisil XL-1B ™ | 22.52 |
| 5 | Aerosil R8200 ™ | 11.77 |
| 6 | Ganzpearl GMP-0830 ™ | 0.19 |
| 7 | Velvet Veil 310 ™ | 0.13 |
| 8 | Aquadispersable Rutile Titanium Dioxide ™ | 0.13 |
| 9 | Yellow Iron Oxide | 0.05 |
| 10 | Red Iron Oxide | 0.03 |
| 11 | Black Iron Oxide | 0.01 |
| 12 | Gransil EP-LS ™ | 3.59 |
| 13 | Velvesil 125 ™ | 3.58 |
| 14 | Flo-Beads SE-3207B ™ | 1.02 |
| 15 | Sepiplus 400 ™ | 1.10 |
| 16 | Water | 23.72 |
| 17 | Granhydrogel O ™ | 6.99 |
| 18 | Jeechem BUGL ™ | 3.50 |
| 19 | Sodium Chloride | 0.35 |
| 20 | Neolone PE ™ | 0.35 |
| 21 | Granpowder Nylon ™ | 2.05 |

Procedure:

Components 1-5 were combined and mixed (Mixture A) in a dual asymmetric centrifugal mixer at 2500 RPM while confirming that the mixture was free of white particulates. Components 6-15 were mixed into Mixture A and mixed in a dual asymmetric centrifugal mixer. Mixture A was confirmed as homogenous. In a separate vessel, components 16 and 20 were mixed with a 4-blade, 40 mm propeller at 550 rpm until homogenous (Mixture B). Mixture B was added to Mixture A dropwise while mixing with a 4-blade 40 mm propeller at 2000 rpm and the mixture was confirmed as homogenous. Component 21 was added to the product of Mixture A and Mixture B and mixed with 4-blade 40 mm propeller at 1000 rpm until homogenous.

Formulation 79-24b

| Component No. | Component | Percent of Formulation (%) |
|---|---|---|
| 1 | Andisil VS 500 ™ | 0.72 |
| 2 | Andisil MV 2000 ™ | 1.07 |
| 3 | Andisil VS 65,000 ™ | 17.91 |
| 4 | Andisil XL-1B ™ | 23.15 |
| 5 | Aerosil R8200 ™ | 12.12 |
| 6 | Ganzpearl GMP-0830 ™ | 0.19 |
| 7 | Velvet Veil 310 ™ | 0.13 |
| 8 | Iron Oxide Tint | 0.22 |
| 9 | Gransil EP-LS ™ | 3.70 |
| 10 | Velvesil 125 ™ | 3.70 |
| 11 | Flo-Beads SE-3207B ™ | 1.06 |
| 12 | Sepiplus 400 ™ | 1.11 |
| 13 | Water | 22.31 |
| 14 | Granhydrogel O ™ | 6.56 |
| 15 | Jeechem BUGL ™ | 3.28 |
| 16 | Sodium Chloride | 0.33 |
| 17 | Neolone PE ™ | 0.33 |
| 18 | Granpowder Nylon ™ | 2.12 |

Procedure:

Components 4, 8 and 9 were combined and homogenized until smooth at 20000 RPM. Components 1-3, 6-7, 10-12 were added and mixed with a dual asymmetric centrifugal mixer at 2500 RPM for 6 minutes until particulates were no longer visible (Mixture A). In a separate vessel, components 13-17 were mixed with a 4-blade, 40 mm propeller at 550 rpm until homogenous (Mixture B). Mixture B was added to Mixture A dropwise while mixing with a 4-blade 40 mm propeller at 2000 rpm and the mixture was confirmed as homogenous. Component 18 was added to the product of Mixture A and Mixture B and mixed with 4-blade 40 mm propeller at 1000 rpm until homogenous.

Formulation 79-45

A 2:1 blend of Formulations 60-211 and 79-24b was mixed together with a 4-blade 40 mm propeller at 2000 rpm for 2 minutes.

Formulation 79-46

A 1:2 blend of Formulations 60-211 and 79-24b was mixed together with a 4-blade 40 mm propeller at 2000 rpm for 2 minutes.

Formulation 79-41

A 1:5 blend of Formulations 60-211 and 79-24b was mixed together with a 4-blade 40 mm propeller at 2000 rpm for 2 minutes.

Formulation 88-30-1

| Component No. | Component | Percent of Formulation (%) |
|---|---|---|
| 1 | VS500 | 0.68 |
| 2 | MV2000 | 1.02 |
| 3 | VS65,000 | 17.00 |
| 4 | XL-1B | 21.96 |
| 5 | Aerosil R 8200 | 11.51 |
| 6 | Dow 246 Fluid | 10.43 |
| 7 | Crodamol STS | 1.15 |
| 8 | 83-49 | 12.00 |
| 9 | 83-50 | 3.39 |
| 10 | Cabosperse 1030K | 20.87 |

Procedure:

Ingredients 1 through 7 were mixed using a propeller blade at 275 RPM to prepare phase A. In a separate vessel components 8 through 10 were mixed, using a propeller blade at 275

RPM, to prepare phase B. Phase B was mixed into phase A at 275 RPM until the emulsion is uniform. An amount of 0.01% iron oxides was added to the final formulation to impart color. Formulation 83-49 and 83-50 are emulsions of VS 165,000 vinyl siloxane and XL-11 hydride functionalized siloxane, respectively, containing 65% siloxanes, 8% oleth-10 surfactant, and the balance water.

Formulation 83-16

| Component No. | Component | Percent of Formulation (%) |
|---|---|---|
| 1 | Gransil EP-LS ™ | 3.5 |
| 2 | Andisil XL-11 ™ | 9.76 |
| 3 | Andisil VS 1,000 ™ | 25.53 |
| 4 | Andisil VS 165,000 ™ | 5.12 |
| 5 | Aerosil R8200 ™ | 10.23 |
| 6 | Velvesil 125 ™ | 3.51 |
| 7 | Flo-Beads SE-3207B ™ | 1.17 |
| 8 | Sepiplus 400 ™ | 1.22 |
| 9 | Granpowder Nylon ™ | 3.9 |
| 10 | Water | 25.47 |
| 11 | Granhydrogel O ™ | 6.32 |
| 12 | Jeechem BUGL ™ | 3.97 |
| 13 | Neolone PE ™ | 0.22 |
| 14 | Iron Oxide Tint Mixture | 0.08 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates were no longer visible (Mixture B). Mixture A and Mixture B were combined and centrifuge mixed for 6 minutes at 2500 RPM (Mixture A+B). In a separate vessel, components 10 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55a

| Component No. | Component | Percent of Formulation (%) |
|---|---|---|
| 1 | Gransil EP-LS ™ | 3.50 |
| 2 | Andisil XL-11 ™ | 8.17 |
| 3 | Andisil VS 1,000 ™ | 32.59 |
| 4 | Andisil VS 165,000 ™ | 6.52 |
| 5 | Andisil XL-11 ™ | 3.04 |
| 6 | Aerosil R8200 ™ | 13.04 |
| 7 | Sepiplus 400 ™ | 1.14 |
| 8 | Water | 21.76 |
| 9 | Granhydrogel O ™ | 6.40 |
| 10 | Jeechem BUGL ™ | 3.20 |
| 11 | Sodium Chloride | 0.32 |
| 12 | Neolone PE ™ | 0.32 |
| 13 | Iron Oxide Tint Mixture | 0.01 |

Procedure:

Components 1 and 2 were combined and homogenized until smooth at 20000 RPM (Mixture A). Components 3 to 7 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 8 to 12 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 13 was added to the product of Mixture A+B and Mixture C and mixed with 4-blade 40 mm propeller at 1000 rpm until homogenous.

Formulation 79-55b

| Component No. | Component | Percent of Formulation (%) |
|---|---|---|
| 1 | Gransil EP-LS ™ | 3.50 |
| 2 | Andisil XL-11 ™ | 8.17 |
| 3 | Andisil VS 10,000 ™ | 30.33 |
| 4 | Andisil VS 165,000 ™ | 7.10 |
| 5 | Andisil XL-11 ™ | 5.49 |
| 6 | Aerosil R8200 ™ | 12.26 |
| 7 | Sepiplus 400 ™ | 1.14 |
| 8 | Water | 21.76 |
| 9 | Granhydrogel O ™ | 6.40 |
| 10 | Jeechem BUGL ™ | 3.20 |
| 11 | Sodium Chloride | 0.32 |
| 12 | Neolone PE ™ | 0.32 |
| 13 | Iron Oxide Tint Mixture | 0.01 |

Procedure:

Components 1 and 2 were combined and homogenized until smooth at 20000 RPM (Mixture A). Components 3 to 7 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 8 to 12 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 13 was added to the product of Mixture A+B and Mixture C and mixed with 4-blade 40 mm propeller at 1000 rpm until homogenous.

Formulation 79-55c

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 500 ™ | 0.84 |
| 4 | Andisil MV 2,000 ™ | 1.29 |
| 5 | Andisil VS 65,000 ™ | 21.04 |
| 6 | Andisil XL-1B ™ | 17.82 |
| 7 | Aerosil R8200 ™ | 14.20 |
| 8 | Sepiplus 400 ™ | 1.14 |
| 9 | Water | 21.76 |
| 10 | Granhydrogel O ™ | 6.40 |
| 11 | Jeechem BUGL ™ | 3.20 |
| 12 | Sodium Chloride | 0.32 |
| 13 | Neolone PE ™ | 0.32 |
| 14 | Iron Oxide Tint Mixture | 0.01 |

Procedure:

Components 1 and 2 were combined and homogenized until smooth at 20000 RPM (Mixture A). Components 3 to 8 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 9 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55d

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 20,000 ™ | 24.52 |
| 6 | Andisil CE-4 ™ | 1.94 |
| 7 | Andisil XL-1B ™ | 0.33 |
| 8 | Andisil XL-11 ™ | 10.97 |
| 9 | Aerosil R8200 ™ | 14.20 |
| 10 | Sepiplus 400 ™ | 1.14 |
| 11 | Water | 21.76 |
| 12 | Granhydrogel O ™ | 6.40 |
| 13 | Jeechem BUGL ™ | 3.20 |
| 14 | Sodium Chloride | 0.32 |
| 15 | Neolone PE ™ | 0.32 |
| 16 | Iron Oxide Tint Mixture | 0.01 |

Procedure:

Components 1 and 2 were combined and homogenized until smooth at 20000 RPM (Mixture A). Components 3 to 10 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 11 to 15 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 16 was added to the product of Mixture A+B and Mixture C and mixed with 4-blade 40 mm propeller at 1000 rpm until homogenous.

Formulation 79-55e

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 65,000 ™ | 22.91 |
| 6 | Andisil XL-1B ™ | 6.78 |
| 7 | Andisil XL-11 ™ | 8.07 |
| 8 | Aerosil R8200 ™ | 14.20 |
| 9 | Sepiplus 400 ™ | 1.14 |
| 10 | Water | 21.76 |
| 11 | Granhydrogel O ™ | 6.40 |
| 12 | Jeechem BUGL ™ | 3.20 |
| 13 | Sodium Chloride | 0.32 |
| 14 | Neolone PE ™ | 0.32 |
| 15 | Iron Oxide Tint Mixture | 0.01 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 10 to 14 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.

Formulation 79-55f

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.34 |
| 4 | Andisil VS 65,000 ™ | 23.74 |
| 5 | Andisil XL-1B ™ | 7.03 |
| 6 | Andisil XL-11 ™ | 8.36 |
| 7 | Aerosil R8200 ™ | 14.71 |
| 8 | Sepiplus 400 ™ | 1.14 |
| 9 | Water | 21.76 |
| 10 | Granhydrogel O ™ | 6.40 |
| 11 | Jeechem BUGL ™ | 3.20 |
| 12 | Sodium Chloride | 0.32 |
| 13 | Neolone PE ™ | 0.32 |
| 14 | Iron Oxide Tint Mixture | 0.01 |

Procedure:

Components 1 and 2 were combined and homogenized until smooth at 20000 RPM (Mixture A). Components 3 to 8 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 9 to 13 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 14 was added to the product of Mixture A+B and Mixture C and mixed with 4-blade 40 mm propeller at 1000 rpm until homogenous.

Formulation 79-55g

| Component No. | Component | Percent of Formulation (%) |
|---|---|---|
| 1 | Gransil EP-LS ™ | 3.50 |
| 2 | Andisil XL-1B ™ | 8.17 |
| 3 | Andisil VS 250 ™ | 1.29 |
| 4 | Andisil MV 2,000 ™ | 1.94 |
| 5 | Andisil VS 20,000 ™ | 22.91 |
| 6 | Andisil XL-1B ™ | 6.78 |
| 7 | Andisil XL-11 ™ | 8.07 |
| 8 | Aerosil R8200 ™ | 14.20 |
| 9 | Sepiplus 400 ™ | 1.14 |
| 10 | Water | 21.76 |
| 11 | Granhydrogel O ™ | 6.40 |
| 12 | Jeechem BUGL ™ | 3.20 |

-continued

| Component No. | Component | Percent of Formulation (%) |
|---|---|---|
| 13 | Sodium Chloride | 0.32 |
| 14 | Neolone PE ™ | 0.32 |
| 15 | Iron Oxide Tint Mixture | 0.01 |

Procedure:

Components 1 and 2 were combined and homogenized until smooth at 20000 RPM (Mixture A). Components 3 to 9 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 10 to 14 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.
Formulation 83-54

| Component No. | Component | Percent of Formulation (%) |
|---|---|---|
| 1 | Andisil VS 10,000 ™ | 27.58 |
| 2 | Andisil VS 165,000 ™ | 6.46 |
| 5 | Andisil XL-11 ™ | 13.50 |
| 6 | Aerosil R8200 ™ | 17.50 |
| 7 | Labrafac CC ™ | 3.00 |
| 7 | Sepiplus 400 ™ | 1.44 |
| 8 | Water | 29.29 |
| 9 | Plantacare 818UP ™ | 0.50 |
| 11 | Sodium Chloride | 0.36 |
| 12 | Neolone PE ™ | 0.36 |
| 13 | Iron Oxide Tint Mixture | 0.01 |

Procedure:

Components 1 to 7 were added and mixed with a dual asymmetric centrifugal mixer at 2500 RPM for 6 minutes until particulates are no longer visible (Mixture A). In a separate vessel, components 8 to 12 were mixed with a 4-blade, 40 mm propeller at 550 rpm until homogenous (Mixture B). Mixture B was added to Mixture A dropwise while mixing with a 4-blade 40 mm propeller at 400 rpm and the mixture was confirmed as homogenous. Component 13 was added to the product of Mixture A and Mixture B and mixed with 4-blade 40 mm propeller at 1000 rpm until homogenous.
Formulation 79-55h

| Component No. | Component | Percent of Formulation (%) |
|---|---|---|
| 1 | Gransil EP-LS ™ | 3.50 |
| 2 | Andisil XL-1B ™ | 8.15 |
| 3 | Andisil VS 250 ™ | 1.25 |
| 4 | Andisil MV 2,000 ™ | 1.85 |
| 5 | Andisil VS 20,000 ™ | 24.40 |
| 6 | Andisil CE-4 ™ | 1.85 |
| 7 | Andisil XL-1B ™ | 0.30 |
| 8 | Andisil XL-11 ™ | 10.80 |

-continued

| Component No. | Component | Percent of Formulation (%) |
|---|---|---|
| 9 | Aerosil R8200 ™ | 14.20 |
| 10 | Sepiplus 400 ™ | 1.14 |
| 11 | Water | 21.50 |
| 12 | Granhydrogel O ™ | 6.30 |
| 13 | Jeechem BUGL ™ | 3.15 |
| 14 | Sodium Chloride | 0.30 |
| 15 | Neolone PE ™ | 0.30 |
| 16 | Beaver UV/Fluorescent Pigment | 1.00 |

Procedure:

Components 1 and 2 were combined and homogenized until smooth at 20000 RPM (Mixture A). Components 3 to 10 were added and mixed with a dual asymmetric centrifugal mixer at 2500 RPM for 6 minutes until particulates are no longer visible (Mixture B). Mixture A and Mixture B were combined and centrifuge mixed for 6 minutes at 2500 RPM (Mixture A+B). In a separate vessel, components 11 to 15 were mixed with a 4-blade, 40 mm propeller at 550 rpm until homogenous (Mixture C). Mixture C was added to Mixture A+B dropwise while mixing with a 4-blade 40 mm propeller at 400 rpm and the mixture was confirmed as homogenous. Component 15 was added to the product of Mixture A+B and Mixture C and mixed with 4-blade 40 mm propeller at 1000 rpm until homogenous.
Formulation 81-18

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 30.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. The final formulation was further homogenized for 2 minutes.
Formulation 81-19

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 29.83 |

| Component No. | Component | Percent of Formulation (%) |
|---|---|---|
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 0.5 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.

Formulation 81-20

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 29.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 1.0 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.

Formulation 81-21

| Component No. | Component | Percent of Formulation (%) |
|---|---|---|
| 1 | Dow 9011 Elastomer Blend | 10.45 |
| 2 | Dow 9045 Elastomer Blend | 10.45 |
| 3 | Dow 245 Fluid | 8.4 |
| 4 | Jeensilc CPS-312 | 2.09 |
| 5 | PT-50175F | 1.00 |
| 6 | Water | 27.33 |
| 7 | Plantacare 818 UP | 0.55 |
| 8 | Neolone PE | 0.21 |
| 9 | Propylene Glycol | 20.87 |
| 10 | Glycerin | 4.16 |
| 11 | Jeechem BUGL | 10.44 |
| 12 | Sodium Chloride | 1.05 |
| 13 | Nylon 10-12 | 3.0 |

Procedure:

Components 1-5 were mixed in a glass beaker at 2000 rpm with 4-blade 40 mm propeller for 2 minutes until mixture was homogeneous (Mixture A). Separately, components 6-12 were mixed until homogenous (Mixture B). Mixture B was added to Mixture A under strong agitation provided by a 4-blade, 40 mm propeller at 2000 rpm until homogeneous. Component 13 was then added and the resulting mixture was homogenized for 2 minutes.

Formulation 79-74

| Component No. | Component | Percent of Formulation (%) |
|---|---|---|
| 1 | Andisil VS 10,000 ™ | 27.58 |
| 2 | Andisil VS 165,000 ™ | 6.46 |
| 5 | Andisil XL-11 ™ | 13.50 |
| 6 | Aerosil R8200 ™ | 17.50 |
| 7 | Schercemol ™ 318 Ester | 3.00 |
| 7 | Sepiplus 400 ™ | 1.44 |
| 8 | Water | 29.29 |
| 9 | Plantacare 818UP ™ | 0.50 |
| 11 | Sodium Chloride | 0.36 |
| 12 | Neolone PE ™ | 0.36 |
| 13 | Iron Oxide Tint Mixture | 0.01 |

Procedure:

Components 1 to 7 were added and mixed with a dual asymmetric centrifugal mixer at 2500 RPM for 6 minutes until particulates are no longer visible (Mixture A). In a separate vessel, components 8 to 12 were mixed with a 4-blade, 40 mm propeller at 550 rpm until homogenous (Mixture B). Mixture B was added to Mixture A dropwise while mixing with a 4-blade 40 mm propeller at 400 rpm and the mixture was confirmed as homogenous. Component 13 was added to the product of Mixture A and Mixture B and mixed with 4-blade 40 mm propeller at 1000 rpm until homogenous.

Pigment Dispersion Formulation 80-23

| Component No. | Component | Percent of Formulation (%) |
|---|---|---|
| 1 | Dow 9011 Elastomer Blend | 10 |
| 2 | Dow 9045 Elastomer Blend | 10 |
| 3 | Dow 245 Fluid | 10 |
| 4 | Water | 27 |
| 5 | Plantacare 818 UP | 0.5 |
| 6 | Neolone PE | 0.5 |
| 7 | Propylene Glycol | 20 |
| 8 | Glycerin | 4 |
| 9 | Jeechem BUGL | 10 |
| 10 | Sodium Chloride | 1 |
| 11 | Nylon | 4.5 |
| 12 | Tint | 2.5 |

Procedure:

Components 1-3 were mixed in a glass beaker at 2000 rpm with 4-blade 40 mm propeller for 2 minutes until homogenous (Mixture A). Separately, components 5-10 were mixed until homogenous (Mixture B). Mixture was added B to Mixture A under strong agitation, provided by a 4-blade, 40 mm propeller at 2000 rpm until homogeneous. Components 11 and 12 were then added and mix at 200 rpm and until homogeneous. The final mixture was then homogenized for 2 minutes.

Formulation 79-88

| Component No. | Component | Percent of Formulation (%) |
|---|---|---|
| 1 | Andisil VS 10,000 ™ | 27.59 |
| 2 | Andisil VS 165,000 ™ | 6.46 |
| 3 | Andisil XL-11 ™ | 13.50 |
| 4 | Aerosil R8200 ™ | 17.50 |
| 5 | Labrafac CC ™ | 3.00 |
| 6 | Sepiplus 400 ™ | 1.44 |
| 7 | Water | 29.29 |
| 8 | Plantacare 818UP ™ | 0.50 |
| 9 | Sodium Chloride | 0.36 |
| 10 | Neolone PE ™ | 0.36 |

Procedure:

Components 1 to 4 were combined and mixed with KitchenAid mixer for 5 hours. Subsequently the mixture was vacuumed overnight. Components 5 and 6 were then added and the mixture was homogenized in a dual asymmetric centrifugal mixer at 2500 RPM. In a separate vessel, components 7 to 10 were mixed with a 4-blade, 40 mm propeller at 550 rpm until homogenous (Mixture B). Mixture B was added to Mixture A dropwise while mixing with a 4-blade 40 mm propeller at 500 rpm and the mixture was confirmed as homogenous.

Formulation 79-88-3A

| Component No. | Component | Percent of Formulation (%) |
|---|---|---|
| 1 | Andisil VS 10,000 ™ | 27.59 |
| 2 | Andisil VS 165,000 ™ | 6.46 |
| 3 | Andisil XL-11 ™ | 13.50 |
| 4 | Aerosil R8200 ™ | 17.50 |
| 5 | Labrafac CC ™ | 3.00 |
| 6 | Simulgel EG ™ | 1.44 |
| 7 | Water | 29.29 |
| 8 | Plantacare 818UP ™ | 0.50 |
| 9 | Sodium Chloride | 0.36 |
| 10 | Neolone PE ™ | 0.36 |

Procedure:

Components 1 to 4 were combined and mixed with KitchenAid mixer for 5 hours.

Subsequently the mixture was vacuumed overnight. Components 5 and 6 were then added and the mixture was homogenized in a dual asymmetric centrifugal mixer at 2500 RPM. In a separate vessel, components 7 to 10 were mixed with a 4-blade, 40 mm propeller at 550 rpm until homogenous (Mixture B). Mixture B was added to Mixture A dropwise while mixing with a 4-blade 40 mm propeller at 500 rpm and the mixture was confirmed as homogenous.

Formulation 79-74-RD

| Component No. | Component | Percent of Formulation (%) |
|---|---|---|
| 1 | Andisil VS 500 ™ | 0.52 |
| 2 | Andisil MV 2000 ™ | 0.80 |
| 3 | Andisil VS 65,000 ™ | 13.04 |
| 4 | Andisil XL-1B ™ | 16.84 |
| 5 | Aerosil R8200 ™ | 8.80 |
| 6 | Water | 50.00 |
| 7 | Veegum Pro | 4.00 |
| 8 | Solagum AX | 1.00 |
| 9 | Dow Corning 5329 | 5.00 |

Procedure:

Components 1 to 5 were combined and mixed under vacuum (Mixture A). In a separate vessel, components 6 to 7 were mixed with a 4-blade, 40 mm propeller at 550 rpm until the mixture was homogenous and the particulates were fully wetted (Mixture B). Component 8 was added to Mixture B and mixed in with a 4-blade 40 mm propeller at 500 rpm until the mixture thickened and became homogenous. Component 9 was added to Mixture B and mixed in with a 4-blade 40 mm propeller at 500 rpm for 10 minutes. Mixture A was added slowly to Mixture B under continuous mixing at 500 rpm. The product was homogenized for 5 minutes at 10,000 rpm.

Formulation 79-90-B

| Component No. | Component | Percent of Formulation (%) |
|---|---|---|
| 1 | Andisil VS 500 ™ | 0.68 |
| 2 | Andisil MV 2000 ™ | 1.04 |
| 3 | Andisil VS 65,000 ™ | 16.95 |
| 4 | Andisil XL-1B ™ | 21.89 |
| 5 | Aerosil R8200 ™ | 11.44 |
| 6 | Water | 40.00 |
| 7 | Veegum Pro | 4.00 |
| 8 | Solagum AX | 1.00 |
| 9 | Dow Corning 5329 | 3.00 |

Procedure:

Components 1 to 5 were combined and mixed under vacuum (Mixture A). In a separate vessel, components 6 to 7 were mixed with a 4-blade, 40 mm propeller at 550 rpm until the mixture was homogenous and the particulates were fully wetted (Mixture B). Component 8 was added to Mixture B and mixed in with a 4-blade 40 mm propeller at 500 rpm until the mixture thickened and became homogenous. Component 9 was added to Mixture B and mixed in with a 4-blade 40 mm propeller at 500 rpm for 10 minutes. Mixture A was added slowly to Mixture B under continuous mixing at 500 rpm. The product was homogenized for 5 minutes at 10,000 rpm.

Formulation 88-70

| Component No. | Component | Percent of Formulation (%) |
|---|---|---|
| 1 | Andisil VS10,000 | 28.7% |
| 2 | Andisil VS165,000 | 6.7% |
| 3 | Andisil XL-11 | 14.0% |
| 5 | Aerosil R8200 | 18.2% |
| 6 | KF6013 | 2.1% |
| 7 | TMF 1.5 | 2.3% |
| 8 | USG 102 | 2.3% |
| 9 | DI water | 22.3% |
| 10 | Glycerin | 1.1% |
| 11 | Jeen BUGL | 1.2% |
| 12 | Jeecide Cap-5 | 1.0% |

Procedure:

Components 1-8 (part A) and components 9-11 (part B). Part B was introduced to part A while mixing part A with a flat propeller blade at 500 RPM. The resulting solution was mixed until a uniform emulsion formed. Component 12 was subsequently added to the emulsion.

Formulation 88-72

| Component No. | Component | Percent of Formulation (%) |
|---|---|---|
| 1 | Andisil VS10,000 | 28.60% |
| 2 | Andisil VS165,000 | 6.69% |
| 3 | Andisil XL-11 | 13.99% |
| 5 | Aerosil R8200 | 18.16% |
| 6 | KF6013 | 2.08% |
| 7 | TMF 1.5 | 2.25% |
| 8 | USG 102 | 2.35% |
| 9 | Pink tint mix | 0.02% |
| 10 | DI water | 22.25% |
| 11 | Glycerin | 1.16% |
| 12 | Jeen BUGL | 1.24% |
| 13 | Veegum Ultra Granules | 0.11% |
| 14 | Kaolin USP BC2747 | 0.10% |
| 15 | Jeecide Cap-5 | 1.00% |

Procedure:

Components 1-9 (Phase A) were mixed separately from components 10-14 (Phase B). Phase B was added to Phase A while mixing at 500 RPM using a 4 paddle mixing blade, followed by homogenization using a Silverson homogenizer for 1 hour at 3000 to 5000 RPM. Subsequently, component 15 was added using mixing blade at 200 rpm.

Formulation 88-75-2

| Component No. | Component | Percent of Formulation (%) |
|---|---|---|
| 1 | Andisil VS10,000 | 21.39% |
| 2 | Andisil VS165,000 | 5.00% |
| 3 | Andisil XL-11 | 10.47% |
| 4 | Aerosil R8200 | 13.58% |
| 5 | RM2051 | 1.95% |
| 6 | DC 556 | 3.12% |
| 7 | FZ3196 | 3.11% |
| 8 | Squalane | 1.85% |
| 9 | USG 102 | 6.90% |
| 10 | Jeechem BUGL | 1.85% |
| 11 | DI water | 29.03% |
| 12 | Polyglycol P425 | 1.22% |
| 13 | Jeecide Cap-5 | 0.52% |

Procedure:

Components 1-4 (Phase A) were mixed. Separately, components 5-9 were also mixed (Phase B) until a uniform dispersion was formed. Components 10-12 (Phase C) were also mixed separately. Phase C was slowly introduced into Phase B, while mixing at 700 RPM with 4 blade propeller rod to create a uniform emulsion (Phase D). Phase D was slowly introduced into Phase A at 700 RPM until uniform, and the resulting formulation was mixed for 5 minutes. Component 13 was added and mixed for 2 minutes.

Formulation 88-75-3

| Component No. | Component | Percent of Formulation (%) |
|---|---|---|
| 1 | Andisil VS10,000 | 18.64% |
| 2 | Andisil VS165,000 | 4.36% |
| 3 | Andisil XL-11 | 9.12% |
| 4 | Aerosil R8200 | 11.84% |
| 5 | RM2051 | 2.21% |
| 6 | DC 556 | 3.53% |
| 7 | FZ3196 | 3.52% |
| 8 | Squalane | 2.10% |
| 9 | USG 102 | 7.81% |
| 10 | Jeechem BUGL | 2.10% |
| 11 | DI water | 32.85% |
| 12 | Polyglycol P425 | 1.38% |
| 13 | Jeecide Cap-5 | 0.54% |

Procedure:

Components 1-4 (Phase A) were mixed. Components 5-9 (Phase B) were mixed separately from Phase A until a uniform dispersion was formed. Components 10-12 (Phase C) were also mixed separately from Phase A and Phase B. Phase C was slowly introduced into Phase B, while mixing at 700 RPM with 4 blade propeller rod to create a uniform emulsion (Phase D). Phase D was slowly introduced to Phase A at 700 RPM until uniform, and mixed for 5 minutes. Component 13 was then introduced to the resulting formulation and mixed for 2 minutes, followed by homogenization at 5000 RPM for 15 minutes.

Formulation 88-80

| Component No. | Component | Percent of Formulation (%) |
|---|---|---|
| 1 | Andisil VS10,000 | 12.72% |
| 2 | Andisil VS165,000 | 2.98% |
| 3 | Andisil XL-11 | 6.23% |
| 4 | Aerosil R8200 | 8.08% |
| 5 | RM2051 | 2.79% |
| 6 | DC 556 | 4.45% |
| 7 | FZ3196 | 4.44% |
| 8 | Squalane | 2.64% |
| 9 | USG 102 | 9.85% |
| 10 | Jeechem BUGL | 2.64% |
| 11 | DI water | 41.44% |
| 12 | Polyglycol P425 | 1.74% |
| 13 | Jeecide Cap-5 | 0.005% |

Procedure:

Components 1-4 (Phase A) were mixed. Components 5-9 (Phase B) were mixed separately from Phase A until a uniform dispersion was formed. Components 10-12 (Phase C) were also mixed separately from Phase A and Phase B. Phase C was slowly introduced into Phase B, while mixing at 700 RPM with 4 blade propeller rod to create a uniform emulsion (Phase D). Component 13 was added to Phase D and mixed for 2 minutes. The resulting emulsion was lowly introduced into Phase A at 700 RPM until uniform, and mixed for 5 minutes, followed by homogenization at 9000 RPM for 7 minutes.

Formulation 88-85-1

| Component No. | Component | Percent of Formulation (%) |
|---|---|---|
| 1 | RM 2051 | 3.28% |
| 2 | FZ 3196 | 4.92% |

-continued

| Component No. | Component | Percent of Formulation (%) |
|---|---|---|
| 3 | USG 102 | 12.11% |
| 4 | water | 48.83% |
| 5 | Jeecide CAP-5 | 0.87% |
| 6 | Andisil VS10,000 | 12.72% |
| 7 | Andisil VS165,000 | 2.98% |
| 8 | Andisil XL-11 | 6.23% |
| 9 | Aerosil R8200 | 8.08% |

Procedure:

Components 1-3 (Phase A) were mixed. Component 4 was added while mixing Phase A, until a white emulsion formed. Components 6-9 (Phase B) were mixed and Phase B was subsequently added to the emulsion and mixed for 5 minutes at 1300 RPM. The resulting formulation was homogenized (Silverson) for 5 minutes and component 5 was added, followed by mixing for 2 minutes at 700 RPM with a propeller blade.

Formulation 88-85-2

| Component No. | Component | Percent of Formulation (%) |
|---|---|---|
| 1 | RM 2051 | 2.62% |
| 2 | FZ 3196 | 3.93% |
| 3 | USG 102 | 9.68% |
| 4 | water | 39.03% |
| 5 | Jeecide CAP-5 | 0.78% |
| 6 | Andisil VS10,000 | 18.6% |
| 7 | Andisil VS165,000 | 4.4% |
| 8 | Andisil XL-11 | 9.1% |
| 9 | Aerosil R8200 | 11.8% |

Procedure:

Components 1-3 (Phase A) were mixed. Component 4 was added while mixing phase A until a white emulsion formed. Components, 6-9 (Phase B) were mixed separately and subsequently added to the emulsion while mixing at 1300 RPM for 5 minutes. The mixture was homogenized (Silverson) for 5 minutes. Component 5 was added and the resulting formulation was mixed for 2 minutes at 700 RPM with a propeller blade.

Formulation 88-83-V2

| Component No. | Component | Percent of Formulation (%) |
|---|---|---|
| 1 | RM 2051 | 3.3% |
| 2 | FZ 3196 | 3.3% |
| 3 | DC 2-1184 fluid | 10.0% |
| 4 | USG 102 | 3.3% |
| 5 | water | 46.3% |
| 6 | Jeecide CAP-5 | 0.3% |
| 7 | Andisil VS10,000 | 14.1% |
| 8 | Andisil VS165,000 | 3.3% |
| 9 | Andisil XL-11 | 6.9% |
| 10 | Aerosil R8200 | 9.0% |

Procedure:

Components 1-4 were mixed (Phase A), followed by addition of component 5, until a white emulsion formed. Component 6 was added to the emulsion and mixed for 5 minutes (emulsion base). Components 7-10 (Phase B) were mixed separately and added to the emulsion base at 1300 RPM, followed by mixing for 5 minutes and homogenization (Silverson) for 10 minutes.

Formulation 88-83-V3

| Component No. | Component | Percent of Formulation (%) |
|---|---|---|
| 1 | RM 2051 | 3.3% |
| 2 | DC 2-1184 fluid | 13.3% |
| 3 | water | 49.7% |
| 4 | Jeecide CAP-5 | 0.3% |
| 5 | Andisil VS10,000 | 14.1% |
| 6 | Andisil VS165,000 | 3.3% |
| 7 | Andisil XL-11 | 6.9% |
| 8 | Aerosil R8200 | 9.0% |

Procedure:

Components 1 and 2 were mixed (Phase A), followed by addition of component 3, until a white emulsion formed. Component 4 was added to the emulsion and mixed for 5 minutes (emulsion base). Components 5-8 (Phase B) were mixed separately and added to the emulsion base at 1300 RPM, followed by mixing for 5 minutes and homogenization (Silverson) for 10 minutes.

Formulation 83-54

Reactive constituent and Reinforcing constituent composition (Vinyl, hydride, fumed silica)

| Tradename | Description | weight percent | ranges lower | ranges upper |
|---|---|---|---|---|
| Andisil VS10,000 | 0.05 mmol/g vinyl, 10,000 cSt | 42.40% | 30 | 50 |
| Andisil VS165,000 | 0.015 mmol/g vinyl, 165,000 cSt | 9.92% | 5 | 15 |
| Andisil XL-11 | 4.35 mmol/g, 45 cSt | 20.75% | 10 | 30 |
| Aerosil R8200 | Silica Silylate | 26.93% | 20 | 34 |
| | total | 100.00% | | |
| Reinforcing Component | | | | |
| RM 2051 Thickening Agent | Sodium Polyacrylate (and) Dimethicone (and) Cyclopentasiloxane (and) Trideceth-6 (and) PEG/PPG-18/18 Dimethicone | 3.63% | 3.00% | 5.00% |

| Tradename | Description | weight percent | ranges lower | ranges upper |
|---|---|---|---|---|
| Gransurf 90 | Cetyl PEG/PPG-10/1 Dimethicone | 0.50% | 0.20% | 2.00% |
| PMX-1184 | dimethicone and trisiloxane | 13.63% | 10.00% | 40.00% |
| Water | N/A | 46.00% | 20.00% | 60.00% |
| Vitamin-C complex | Ascorbic Acid | 0.08% | 0.05% | 0.50% |
| Jeecide CAP-5 | Phenoxyethanol, Caprylyl Glycol, Potassium Sorbate, Aqua, Hexylene Glycol | 0.33% | | 1.00% |
| Tween 20 | Polysorbate 20 | 0.33% | | 5.00% |
| Vitamin-A complex | Vitamin A Palmitate 1.7 MIU/g | 0.40% | | 5.00% |
| Vitamin-E complex | Vitamin E Acetate | 0.10% | | 5.00% |
| Reactive constituent and Reinforcing constituent composition (Vinyl, hydride, fumed silica) from above | N/A | 35.00% | 30.00% | 60.00% |
| | total | 100.00% | | |

Procedure:

Formulation 83-54 was prepared by a procedure similar to 88-83-V3.

Andisil VS 10,000, Andisil VS 165,000, Andisil XL-11 were obtained from Anderson and Associates, Aerosil R8200 was obtained from Evonik, and the four componets were mixed by Crisil. RM 2051 Thickening Agent and PMX-1184 were obtained from Dow. Gransurf 90 was obtained from Grant. Vitamin-C complex and Vitamin A comples were obtained from DSM. Jeecide CAP-5 was obtained from Jeen. Tween 20 was obtained from Croda. Vitamin-E complex was obtained from TRI-K.

The cross-linking component second step includes formulations 60-148-99, 60-144-San 86-114, and 86-141c shown below.

Formulation 60-148-99

| Component No. | Component | Percent of Formulation (%) |
|---|---|---|
| 1 | Water | 28.60 |
| 2 | Plantacare 818UP | 0.49 |
| 3 | Propylene Glycol | 19.72 |
| 4 | Glycerin | 3.94 |
| 5 | Jeechem BUGL | 9.86 |
| 6 | Sodium Chloride | 0.99 |
| 7 | Dow Elastomer Blend 9011 | 9.86 |
| 8 | Dow Elastomer Blend 9041 | 9.86 |
| 9 | Dow 245 Fluid | 7.89 |
| 10 | Jeensilc CPS-312 | 1.97 |
| 11 | Nylon 10-12 | 4.64 |
| 12 | Chronosphere Optical Brite | 0.18 |
| 13 | Platinum divinyl complex PC 075.3 | 1.00 |

Procedure:

Components 1-6 were combined and mixed at 750 RPM for two minutes with a 4-blade 40 mm propeller until homogenous to create an aqueous phase. In a separate container components 7-10 were mixed at 750 RPM for two minutes with a 4-blade 40 mm propeller until homogenous to create a Silicon Mixture A. To the aqueous phase, components 11 and 12 were added and mixed at 750 RPM with a 4-blade 40 mm propeller. The mixing speed was increased to 1000 RPM and the mixture was mixed until homogenous and thickened. Component 13 was added and stirred at 1000 RPM for 1 minute, then homogenized at 25,000 RPM for 5 minutes.

Formulation 60-144-San

| Component No. | Component | Percent of Formulation (%) |
|---|---|---|
| 1 | Water | 67.47 |
| 2 | Carbopol Ultrez 21 | 1.01 |
| 3 | Denatured Ethanol 190 Proof | 29.35 |
| 4 | Glycerin | 2.02 |
| 5 | 2% Sodium Hydroxide | 0.20 |
| 6 | Platinum divinyl complex 3% PC 075.3 | 1.99 |

Procedure:

Components 1 and 2 were gently blended with a 4-blade 40 mm propeller blade at 250 RPM until the Carbopol was completely wetted and the mixture was free of white particulates. Components 3 and 4 were added under moderate agitation provided by a 4-blade 40 mm propeller at 500 RPM. Component 5 was added dropwise under moderate agitation provided by a 4-blade 40 mm propeller at 550 RPM until the mixture was homogenous and thickened. Component 6 was added under moderate agitation provided by a 4-blade 40 mm propeller at 550 RPM, followed by mixing at 1000 RPM for 5 minutes until the mixture was homogeneous.

Formulation 86-114 and 86-141c

| Tradename | Description | weight percent | Supplier | lower | upper |
|---|---|---|---|---|---|
| Platinum Divinyl Complex 2% PT-50175F (CAS# 68478-92-2, 2627-95-4, 68083-19-2) | Karstedt's catalyst in stabilizing vinyl-dimethicone | 1.00% | Umicore | 0.50% | 2.50% |
| | | 1.00% total | | | |
| 86-114 | Crosslinking Component #1 | | | | |
| Dow 9011 Elastomer Blend | Cyclopentasiloxane (and) PEG-12 Dimethicone Crosspolymer | 10.00% | Dow Corning | 5.00% | 20.00% |
| Dow 9045 Elastomer Blend | Cyclopentasiloxane and Dimethicone Crosspolymer | 10.00% | Dow Corning | 5.00% | 20.00% |
| PMX-0245 | Cyclopentasiloxane | 10.00% | Dow Corning | 5.00% | 25.00% |
| Water | | 28.50% | NA | — | 90.00% |
| Sodium Chloride | Sodium Chloride | 1.00% | Spectrum | — | 5.00% |
| Plantacare 818 UP | Coco-Glucoside | 0.50% | Cognis | — | 4.00% |
| Tween 20 | Polysorbate 20 | 0.00% | Cognis | — | 2.00% |
| Propylene Glycol | Propylene Glycol | 20.00% | Ruger Chemical Co | — | 40.00% |
| Lipo Polyglycol® 200 | PEG-4 | 0.00% | Lipo Chemicals Inc | — | 40.00% |
| Glycerin | Glycerin | 4.00% | Ruger Chemical Co | — | 10.00% |
| Jeechem BUGL | 1,3-Butylene Glycol | 10.00% | Jeen | — | 50.00% |
| Nylon 10-12 | Nylon 12 and Isopropyl Titabium Triisostearate | 4.50% | KOBO | — | 15.00% |
| Jeecide CAP-5 | Phenoxyethanol, Caprylyl Glycol, Potassium Sorbate, Aqua, Hexylene Glycol | 0.50% | Jeen | — | 2.00% |
| PT-50175F | Platinum Divinyldisiloxane | 1.00% | Umicore | 0.50% | 2.50% |
| | total | 100.00% total | | | |
| 86-141c | Crosslinking Component #2 | | | | |
| KSG-240 | Dimethicone/PEG-10/15 Crosspolymer | 10.00% | Shin Etsu | 3.00% | 20.00% |
| DC 9045 | Cyclopentasiloxane and Dimethicone Crosspolymer | 7.50% | Dow Corning | | 25.00% |
| KF-995 | Cyclopentasiloxane | 11.50% | Shin Etsu | | 25.00% |
| KF-6028 | PEG-9 Polydimethylsiloxyethyl Dimethicone | 1.00% | Shin Etsu | | 4.00% |
| Water | | 28.25% | NA | | 90.00% |
| Sodium Chloride | Sodium Chloride | 1.00% | Spectrum | | 5.00% |
| Plantacare 818 UP | Coco-Glucoside | 0.50% | Cognis | | 4.00% |

| Tradename | Description | weight percent | Supplier | lower | upper |
|---|---|---|---|---|---|
| Tween 20 | Polysorbate 20 | 0.00% | Cognis | | 2.00% |
| Propylene Glycol | Propylene Glycol | 20.00% | Ruger Chemical Co | | 40.00% |
| Lipo Polyglycol ® 200 | PEG-4 | 0.00% | Lipo Chemicals Inc | — | 40.00% |
| Glycerin | Glycerin | 4.00% | Ruger Chemical Co | | 10.00% |
| Jeechem BUGL | 1,3-Butylene Glycol | 10.00% | Jeen | | 50.00% |
| Nylon 10-12 | Nylon 12 and Isopropyl Titabium Triisostearate | 4.50% | KOBO | | 15.00% |
| Jeecide CAP-5 | Phenoxyethanol, Caprylyl Glycol, Potassium Sorbate, Aqua, Hexylene Glycol | 0.50% | Jeen | | 2.00% |
| PT-50175F | Platinum Divinyldisiloxane | 1.25% | Umicore | | 2.50% |
| | | 100.00% | total | | |

Procedure for 86-114:

Components 1-3 were combined and mixed at 750 RPM for two minutes with until homogenous to create an silicone phase. In a separate container components 4-11 and 13 were mixed at 750 RPM for 15 minutes with a until homogenous to create a water phase. The water phase was added slowly to the silicone phase and mixed at 750 RPM. The mixing speed was increased to 2000 RPM and the mixture was mixed until homogenous and thickened. Component 12 was added and stirred at 1000 RPM for 5 minutes. Component 14 was added and stirred at 1000 RPM for 5 minutes.

Procedure for 86-141c:

Components 1-4 were combined and mixed at 750 RPM for two minutes with until homogenous to create an silicone phase. In a separate container components 5-12 and 14 were mixed at 750 RPM for 15 minutes with a until homogenous to create a water phase. The water phase was added slowly to the silicone phase and mixed at 750 RPM. The mixing speed was increased to 2000 RPM and the mixture was mixed until homogenous and thickened. Component 13 was added and stirred at 1000 RPM for 5 minutes. Component 15 was added and stirred at 1000 RPM for 5 minutes.

LPS026 (88-116)

| phase | ingredient | INCI | lot number | Manufacturer | % |
|---|---|---|---|---|---|
| A | DI water | | NA | | 50.0% |
| A | Jeechem BUGL | Butylene glycol | J9816G07890 | JEEN | 5.0% |
| A | Cremaphor EL | PEG-35 Castor Oil | 9288465680 | BASF | 5.0% |
| A | schercelmol 318 | Isopropyl Isostearate | 100979775 | Lubrizol | 2.0% |
| A | Jeecide CAP-5 | Phenoxyethanol, Caprylyl Glycol, Potassium Sorbate, Aqua, Hexylene Glycol | J6916E0207 | JEEN | 0.5% |
| B | PMX1184 | dimethicone and trisiloxane | 6462279 | Dow Corning | 37.5% |

Mix the components of phase A in the mixing vessel and stir until it appears uniform.
Mix the components of phase B in a separate vessel until it appears uniform.
Add phase B to Phase A (step 2 to step 1) slowly and mix until uniform.

Formulation LPS-033 (STEP 1)

| Component No. | Component | Percent of Formulation (%) |
|---|---|---|
| 1 | Andsil VS10,000 | 14.13 |
| 2 | Andsil VS165,000 | 3.30 |
| 3 | Andsil XL-11 | 6.92 |
| 4 | Aerosil R8200 | 8.98 |
| 5 | PMX-1184 | 13.33 |
| 6 | RM 2051 | 5.00 |
| 7 | Water | 48.01 |
| 8 | Jeecide CAP-5 | 0.33 |

Procedure:

Components 1-4 are mixed in a beaker until the mixture is uniform and free of white particulates. Subsequently, Component 5 is added and the mixture is confirmed homogenous. Component 6 is then added to this and mixed until uniform (Mixture A). In a separate vessel, Components 7 and 8 are hand mixed until homogenous (Mixture B). Mixture B is very slowly added to Mixture A while maintaining a relatively low mixing speed. After all of Mixture B is added, the whole mixture is mixed for 10 minutes to assure homogeneity.

Formulation 100-47-300D (STEP 1)

| Component No. | Component | Percent of Formulation (%) |
|---|---|---|
| 1 | Andsil VS 10,000 | 14.13 |
| 2 | Andsil VS 165,000 | 3.30 |
| 3 | Andsil XL-11 | 6.92 |
| 4 | Aerosil R8200 | 8.98 |
| 5 | PMX-1184 | 13.33 |
| 6 | RM 2051 | 3.33 |
| 7 | Covacryl MV60 | 0.43 |
| 8 | Water | 49.25 |
| 9 | Jeecide CAP-5 | 0.33 |

Procedure:

Components 1-4 are premixed until confirm as free of white particulates. Component 5 is added and mixed at 200 rpm until uniform (Mixture A). Components 6 and 7 are added sequentially with mixing at 500 rpm after each addition until homogeneous. (Mixture A) In a separate vessel, components 8 and 9 are hand mixed until homogenous (Mixture B). Mixture B to was added Mixture A under strong agitation, provided by a 4-blade, 40 mm propeller at 800 rpm. After all of Mixture B is incorporated mix for 5 minutes. The mixture is confirmed as homogenous.

Formulation LPS-034 (STEP 2)

| Component No. | Component | Percent of Formulation (%) |
|---|---|---|
| 1 | Dow 9011 Elastomer Blend | 10.00 |
| 2 | Dow 9045 Elastomer Blend | 10.00 |
| 3 | KF-995 | 10.00 |
| 4 | PT-50175F | 1.00 |
| 5 | Water | 28.5 |
| 6 | Plantacare 818 UP | 0.50 |
| 7 | Propylene Glycol | 20.00 |
| 8 | Glycerin USP | 4.00 |
| 9 | Jeechem BUGL | 10.00 |
| 10 | Sodium Chloride | 1.00 |
| 11 | Nylon 10-I2 | 4.5 |
| 12 | Jeecide CAP-5 | 0.5 |

Procedure:

Components 5 and 10 are mixed until mixture is uniform. Component 12 is added to the mixture and mixed well. In a separate vessel, components 6 to 9 are mixed until the mixture is homogeneous. The mixture of components 5, 10 and 12 are then added to this mixture and stirred (Mixture A). Components 1, 2 and 3 are mixed in a separate vessel until they appear homogenous. 25% of Mixture A is slowly added to the vessel containing components 1 to 3 and mixed until the emulsion forms. Then, the rest of Mixture A is slowly added while continuously mixing. Once the mixture appears homogenous, Component 11 is slowly added and mixed until the mixture appears uniform. Finally, Component 4 is added and the mixture is stirred for a few minutes.

Formulation 92-059-10 (REMOVER)

| Component No. | Component | Percent of Formulation (%) |
|---|---|---|
| 1 | Water | 52.94 |
| 2 | PMX-1184 | 29.96 |
| 3 | Permethyl 99A | 9.99 |
| 4 | Jeechem BUGL | 4.24 |
| 5 | Potassium Phosphate Dibasic | 0.90 |
| 6 | Sodium Chloride | 0.75 |
| 7 | Jeecide CAP-5 | 0.50 |
| 8 | Disodium EDTA | 0.50 |
| 9 | Maltodextrin | 0.30 |
| 10 | Ultracolor Blue 1% Dye | 0.09 |
| 11 | Pluracare ® L 64 | 0.03 |

Procedure:

All the components except components 2 and 3 are mixed until the mixture is uniform. Components 2 and 3 are added to the mixture to form a two-phase mixture.

The additional formulations below can be made by the methods similar to those described above.

Formulation A: Step 1

| # | Ingredient | Weight (%) |
|---|---|---|
| 1 | Water | 49.96% |
| 2 | Vinyl dimethicone | 17.44% |
| 3 | Silica silylate | 8.98% |
| 4 | Hydrogen dimethicone | 6.92% |
| 5 | Decamethyltetrasiloxane | 5.71% |
| 6 | Octamethyltetrasiloxane | 5.71% |
| 7 | Dodecamethylpentasiloxane | 2.86% |
| 8 | Sodium Polyacrylate | 1.30% |
| 9 | Cyclopentasiloxane | 0.45% |
| 10 | Trideceth-6 | 0.30% |
| 11 | Polyoxyalkylated dimethicone | 0.05% |
| 12 | Phenoxyethanol | 0.33% |
| 13 | Caprylyl Glycol | |
| 14 | Potassium Sorbate | |
| 15 | Hexylene Glycol | |
| | Total | 100.00% |

Formulation B: Step 2

| # | Ingredient | Weight (%) |
|---|---|---|
| 1 | Water | 28.50% |
| 2 | Cyclopentasiloxane | 26.00% |
| 3 | Propylene Glycol | 20.00% |
| 4 | Butylene Glycol | 10.00% |
| 5 | Nylon-12 | 4.50% |
| 6 | Glycerin | 4.00% |
| 7 | Polyoxyalkylated Dimethicone Crosspolymer | 2.00% |
| 8 | Dimethicone Crosspolymer | 2.00% |
| 9 | Sodium Chloride | 1.00% |
| 10 | Polyalkylglucoside | 0.50% |
| 11 | Divinyldisiloxane | 0.97% |
| 12 | Phenoxyethanol | 0.50% |
| 13 | Caprylyl Glycol | |
| 14 | Potassium Sorbate | |
| 15 | Hexylene Glycol | |

-continued

| # | Ingredient | Weight (%) |
|---|---|---|
| 16 | Platinum | 0.02% |
| 17 | Isopropyl Titanium Tri-Isostearate | 0.01% |
| | Total | 100.00% |

Formulation C: Remover

| # | Ingredient | Weight % |
|---|---|---|
| 1 | Water | 52.94% |
| 2 | Decamethyltetrasiloxane | 11.98% |
| 3 | Octamethyltetrasiloxane | 11.98% |
| 4 | Isododecane | 9.99% |
| 5 | Dodecamethylpentasiloxane | 5.99% |
| 6 | Butylene Glycol | 4.24% |
| 7 | Potassium phosphate dibasic | 0.90% |
| 8 | Sodium Chloride | 0.75% |
| 9 | Disodium EDTA | 0.30% |
| 10 | Maltodextrin | 0.30% |
| 11 | Phenoxyethanol | 0.50% |
| 12 | Caprylyl Glycol | |
| 13 | Potassium Sorbate | |
| 14 | Hexylene Glycol | |
| 15 | Polaxomer 184 | 0.03% |
| 16 | Propylene Glycol | 0.09% |
| 17 | FD&C Blue 1 | |
| | | 100.00% |

Example 2

Hydration Study

I. Objective

To evaluate the effects of the test products utilizing measurements of skin hydration and elasticity. Skin hydration has been shown to significantly improve skin conditions and quality of life for patients suffering from conditions of compromised skin barrier such as subjects suffering from dermatological disorders or recovering from light or laser treatment. Skin hydration provides transient relief from irritation. Subsequently, an improved barrier function and stratum corneum hydration makes the epidermis more resistant to external stressors and reduces the induction of Koebner phenomena (excoriation, maceration and infectious foci (Streptococcus pyogenes)). Therefore, treatments that result in enhanced hydration of the subject's skin may be useful in treating subjects suffering from conditions of compromised skin barrier including dermatological disorders or subjects recovering from laser or light or chemical peel treatment. In addition, hydration of skin is useful in relieving or resolving the symptoms of such conditions including symptoms such as itchy skin; flaking or peeling skin; blisters on skin; redness or swelling of the skin; or oozing, scabbing and scaling skin.

II. Experimental Design

A. General Considerations

The experimental design was based on previous studies by several different investigators which have been published as follows:

M. Obata and H. Tagami. A rapid in vitro test to assess skin moisturizers. J. Soc. Cosmet. Chem., 41, 235-241 (July/August, 1990) and P. Agache, S. Mary, P. Muret, A. M. Matta, P. Humbert. Assessment of the Water Content of the Stratum corneum using a Sorption-Desorption Test. Dermatology, 2001, 202; 308-313, the teachings of which are incorporated herein by reference.

Brief Description of the Protocol

Five panelists participated in this study. There were 6 test sites, 3 on each volar forearm of the selected panelists. Four of the six volar forearm test sites will be treated (randomized) and two sites will remain non-treated to serve as controls. Following Baseline measurements with a Skicon-200 Conductance Meter, cyberDERM RG1 Evaporimeter and DermaLab Suction Cup the test products were applied to 4 of the 6 sites and the remaining two sites served as non-treated controls. Follow-up measurements with the evaporimeter and suction cup were taken from each of the six volar forearm test sites approximately 4 hours after treatment. After the 4-hour TEWL and suction cup volar forearm measurements have been completed, the test product will be removed from the 4 volar forearm test sites. Conductance measurements will be taken from the 6 volar forearm sites immediately and 5, 10 and 15 minutes after removal. Post removal TEWL and suction cup measurements will be taken from the volar forearm sites following completion of the 15-minute post removal conductance measurements. The panelists will be required to acclimate in an environmentally controlled room for approximately 25-30 minutes prior to all measurements.

Summary of Events:

| PROCEDURES | Pre-Study | Baseline | 4 Hours Post Treatment | Post Removal Immed. | 5 min | 10 min | 15 min |
|---|---|---|---|---|---|---|---|
| Sign consent | X | | | | | | |
| Pre-trial conditioning | X | | | | | | |
| Wash test sites, dry 15 minutes | | X | | | | | |
| Acclimate 30 minutes | | X | X | | | | |
| Skicon measurements | | X | | X | X | X | X |
| TEWL measurements | | X | X | | | | X |
| Suction Cup measurements | | X | X | | | | X |
| Treatment and control applied to 4 of 6 volar forearm sites | | X | | | | | |
| Treatment and control removed from 4 volar forearm sites | | | X | | | | |

B. Panelist Selection

Six (6) panelists were recruited in order to finish with 5 panelists. Five panelists were scheduled for the study and one panelist was recruited as a back-up. Volunteers were recruited from a pool of healthy suburban women who met the inclusion/exclusion criteria. The inclusion/exclusion criteria were as follows:

1. Inclusion Criteria
   a. Is female between the ages of 40 and 50
   b. Agrees to discontinue use of all moisturizing products (soaps, lotions, sunscreens, insect repellent, etc.) on their arms for the 3 days prior to their day of testing
   c. Agrees to refrain from exercising and/or drinking hot or caffeinated beverages during the 2 hours prior to their appointment on the day of testing (this affects the measurements)

d. Willing to remain at the lab until their 4 hour measurements are completed on the day of testing
e. Willing to wear a short-sleeved shirt or a shirt with sleeves that can be pulled or rolled above the elbows to each visit
f. Willing to wear non-occlusive, non-contact protective arm guards in between product application and their 4-hour measurements on the day of testing
g. Willing and able to follow all study requirements and restrictions h. Is able to read, understand, and sign the consent form.
2. Exclusion Criteria
a. Is pregnant, nursing or planning a pregnancy as determined by interview.
b. Is currently going through menopause (i.e., experiencing hot flashes).
c. Is a smoker.
d. Has any current skin condition on their arms other than dry skin (e.g. psoriasis, eczema, atopic dermatitis, etc.)
e. Has any marks, scars, scratches, etc. on their volar forearms
f. Have known sensitivities to adhesives, cosmetics, moisturizers or fragrances.
g. Any other condition or factor the Investigator or his duly assigned representative believes may affect the skin response or the interpretation of the test results.

Each volunteer signed a consent form and HIPAA Authorization form after being informed as to their obligations and any risks that they might encounter as a participant in this study.

Each candidate was instructed to stop the use of all moisturizing products (soaps, lotions, sunscreens, insect repellent, etc.) on their arms during a 3 day pre-conditioning period prior to testing. Candidates were instructed not to exercise or drink hot or caffeinated beverages within 2 hours prior to their day of testing visit as this will affect the measurements. They were also instructed to wear a short-sleeved shirt or a shirt with sleeves that can be pulled or rolled above the elbows to each visit.

C. Treatments and Procedures

Prior to Baseline acclimation, the test areas on each panelist was cleansed with Kimwipes wetted with water and patted dry with dry Kimwipes. The cleansing should be as minimal as wiping twice with wet Kimwipes and subsequent patted drying by stroking twice with dry Kimwipes.

Six 5 cm by 5 cm test sites on the left and right volar forearms (3 on each arm) using a standard template were outlined on each panalist. The panelists were instructed to keep their arms air-exposed for the duration of this study and not to touch their arms during the study.

1. IBS Skicon-200 Conductance Meter Measurements (Skin hydration)

All measurements were taken following a 25-30 minute acclimation period in a controlled environment with the relative humidity maintained at less than 50% and temperature maintained at 19-22° C.

As has been shown, most notably by Obata and Tagami [Obata, M. and Tagami, H. A rapid in vitro test to assess skin moisturizers. In: J. Soc. Cosmet. Chem., 41, 235-241 (July/August, 1990), the teachings of which are incorporated herein by reference], the ability of an alternating current to flow through the stratum corneum is an indirect measure of its water content. The value recorded which is expressed in units of microsiemens represents the AC conductance 2-3 seconds after placing the spring-loaded probe tip to the sample site. This timing interval is sufficiently long enough for the electronic circuits to stabilize in response to this change in conductance but short enough not to be influenced by an increased hydration at the probe tip due to its being occlusive and acting as a hindrance to the normal water loss at the test site.

In this study, an IBS Skicon-200 Conductance Meter equipped with a Measurement Technologies probe to further enhance its ability to measure changes in skin surface hydration was used. It was anticipated that skin occlusion or treatment with a moisturizer will produce increased conductance values.

Three conductance measurements from each of the six volar forearm test sites at Baseline were taken. Following completion of the 4 hour TEWL and suction cup measurements (as described below), the test products removed sequentially from each test site and another series of measurements were taken immediately and again every 5 minutes for 15 minutes.

2. cyberDERM RG1 Evaporimeter Measurements (Transepidermal Water Loss (TEWL))

All water loss measurements were taken following a 25-30 minute acclimation period in a controlled environment with the relative humidity maintained at less than 50% and temperature maintained at 19-22° C.

At Baseline, evaporative water loss measurements were taken from each of the test sites as described below. Any individuals with water loss values outside the normal range ($>10.0$ gms/$m^2$ hr) were excluded at this time.

Evaporative water loss measurements provide an instrumental assessment of skin barrier function. These measurements were made using a recently calibrated cyberDERM RG1 Evaporimeter System (Broomall, Pa.) with TEWL Probes that are manufactured by Cortex Technology (Hadsund, Denmark) and available in the US through cyberDERM, inc. (Broomall, Pa.).

This instrument is based on the vapor pressure gradient estimation method as designed by Nilsson and initially utilized by the Servo Med Evaporimeter. There are slight dimensional differences and the sensor technology is greatly improved in the DermaLab® TEWL probe but the underlying principles of the measurement remain the same. Both probes contain two sensors that measure the temperature and relative humidity at two fixed points along the axis normal to the skin surface. This arrangement is such that the device can electronically derive a value that corresponds to evaporative water loss expressed in gm/m2 hr. Evaporimetry with TEWL Probe is more fully described in two publications by Grove et al: Grove, G. L., M. J. Grove, C. Zerweck and E. Pierce: Comparative metrology of the evaporimeter and the DermaLab® TEWL probe. Skin Res. & Tech. 5:1-8, 1999 and Grove, G. L., M. J. Grove, C. Zerweck and E. Pierce: Computerized evaporimetry using the DermaLab® TEWL probe. Skin Res. & Tech. 5:9-13, 1999, the teachings of which are incorporated herein by reference. The guidelines established for using the Servo Med Evaporimeter as described by Pinnagoda [Pinnagoda, J., R. A. Tupker, T. Anger and J. Serup. Guidelines for transepidermal water loss (TEWL) measurement. In: Contact Dermatitis 1990: 22:164-178, the teachings of which are incorporated herein by reference] are quite appropriate for the DermaLab® TEWL Probe as well.

The cyberDERM RG1 Evaporimeter System is completely computerized and continuously communicates with its PC through a USB port and associated cyberDERM, inc. software for the Evaporimeters. The application program entitled x1WL2M that captures the water loss data from the attached evaporimeter at a sampling rate of 8 inputs/second was used. These inputs were graphed as a real time display on the computer monitor. The extracted value refers to the average evaporative water loss rate collected over a twenty-second interval once steady state conditions had been achieved. These were directly transferred to an Excel file using a DDE link.

At Baseline, approximately 4 hours after treatment and again post removal of the test products, duplicate water loss readings were taken from each volar forearm site and electronically recorded using a spreadsheet format based on Excel software that computes the average value for each test site. These values were also manually recorded on a worksheet that serves as a back up in case of possible computer malfunction. Such measures provide a noninvasive method for determining the barrier function of the stratum corneum.

3. DermaLab® USB with a Suction Cup (skin elasticity via measurements of skin recoil time)

All water loss measurements were taken following a 25-30 minute acclimation period in a controlled environment with the relative humidity maintained at less than 50% and temperature maintained at 19-22° C.

4. Test Product & Treatment Procedures a. Test Products

The 2-step test product: LP Product A (Treatment) and LP Product B (Perfector) designed as LP A+B.

Control: Vaseline (Petrolatum)

b. Test Product Application

Six test sites were located on the left and right volar forearms, with three sites on each arm. Each site was approximately 5 cm×5 cm in size.

After the Baseline assessments and measurements are completed, the test sites for each panelist were treated according to the randomization schedule described below. Products were applied in duplicate with each product being applied to one site on each arm. One site on each arm remained non-treated to serve as untreated controls.

Randomization Scheme:

| Panelist # | Arm R | | | Arm L | | |
|---|---|---|---|---|---|---|
| | RU | RC | RL | LU | LC | LL |
| 1 | Blank | LP A + B | Vaseline | LP A + B | Vaseline | Blank |
| 2 | Vaseline | Blank | LP A + B | Blank | LP A + B | Vaseline |
| 3 | LP A + B | Vaseline | Blank | Vaseline | Blank | LP A + B |
| 4 | Blank | LP A + B | Vaseline | LP A + B | Vaseline | Blank |
| 5 | Vaseline | Blank | LP A + B | Blank | LP A + B | Vaseline |

A DermaLab® USB with a Suction Cup was used to evaluate skin elasticity. The suction probe which was placed on the test site is capable of producing a vacuum up to 65 kPa. Within the suction chamber there were 2 light beams set at fixed distances from the skin surface. The measuring aperture was 10 mm in diameter and the probe itself had an ultra low weight of approximately 7 g for minimum skin bias. The probe was secured to the panelist's site using an adhesive ring. When the suction pump was activated it created a vacuum that drew the skin into the chamber. The pressure required to draw the skin to the point where it blocks the lower light beam was recorded. The pump remained on and the skin continues to draw into the chamber to the point that it eventually blocked the upper light beam as well. The skin was then allowed to relax for 10 seconds before the vacuum resumed for a total of 5 cycles. The time it took for the skin to retract through the light beams to its natural state is reported and referred to as the "retraction time". The geometry of the suction cup standard probe was such that the 10 mm diameter section of the skin being sampled was extended approximately 2% and 12% when lifted to these respective levels. As both the stress and strain at these 2 points is known, the "stiffness" ratio that is similar to Young's Modulus for more ideal materials can be computed. The results obtained with the DermaLab® Suction Cup in terms of a stiffness index:

$$\frac{\Delta \text{ pressure in KPa}}{\Delta \text{ distance in mm}}$$

Skin that is firm and taut will have a much higher stiffness index than skin that is loose and saggy.

The one measurement from each site at Baseline, 4 hours post treatment and again post removal of the test products was taken. At each of these time points, suction cup measurements were taken after the TEWL measurements were completed. Measurements were taken from the same location for each site.

An aliquot of 0.08-0.1 mL was dispensed to finger cot and then directly applied to the test area. The two materials are applied to the same test area, the first test material (LP Product A, 0.08 mL) was applied to skin first and the second test material (LP Product B, 0.1 mL) was dispensed with a new finger cot and applied onto the same area treated with the first test material by gliding motion to coat the treated area but not by rubbing in to minimize the mixing of the two test materials.

Application of Vaseline:

To the test site, 0.05 cc of test material using a graduated 1.0 cc syringe was delivered and then a finger cot was used to gently spread an even film of the product over the test area.

Panelists were required to wear non-occlusive, non-contact protective arm guards to minimize product transfer and site contact with foreign material following application of the test products and until their 4-hour measurements were completed. The panelists were sequestered at the facility until their 4-hour measurements were completed.

c. Test Product Removal

Removal after 4 hours:

All the test area will be cleansed with 88-116 removal tonic. The removal tonic was shaken well to be homogeneous prior to use. The removal tonic (1.5 mL) was poured onto a cotton round pad and then the wet pad was placed on the test area. After 30 seconds of the incubation, the testing product(s) was removed by gently wiping against the boundary of the treatment and rolling the product off the treated area. Severe rubbing or adding additional pressure was avoided. Upon removal, the area was cleaned with Kimwipes wetted with water and patted dry with dry Kimwipes. All three test area including Vaseline and untreated control was removed and cleansed as above E. Statistical Analysis The sorted data was tabulated and arranged in order of panelist number for every point of evaluation. Due to the small sample size, a full statistical analysis was not warranted. For all analysis, a two-tailed $p<0.05$ will be taken as the level of significance.

6. Results

1. IBS Skicon-200 Conductance Measurements

The film treatment sites demonstrated a two-fold increase in the skin conductance when compared with petrolatum after removal of each substance (p<0.05). (FIG. 1). The greatest increase was associated with LP A+B treated sites while untreated sites demonstrated the least increase in hydration.

2. cyberDERM RG1 Water Loss Measurements

Evaporative water loss measurements show that both LP A+B and vaseline were relatively occlusive 4 hours post application. Specifically, TEWL values were significantly lower for petrolatum and LP A+B as compared to the blank control site prior to removal (p<0.05). Differences were not detected between LP A+B and petrolatum. Upon removal of the films water loss values are found to return toward Baseline levels. Little or no change was associated with the no treatment controls.

Example 3

DermaLab Suction Cup Measurements (Skin Elasticity)

Similar to the protocol described above in Example 2, an additional study was conducted to evaluate the skin elasticity of the LP A+B film, Vaseline and untreated blank control. Six voluntary participants were selected for the study as described in the protocol above in Example 2. A baseline measurement was determined by DermaLab Suction Cup on the volar arm test area. Next, the test areas were treated with LP A+B as described above in Example 2. The skin retraction times were determined by DermaLab Suction Cup at 4 hour post treatment and also immediately after removal. The results are summarized below:

Results

| | Retraction (mS) | | |
|---|---|---|---|
| | Baseline | 4 hr post Treatment | After Removal |
| Average | 493.00 | 355.03 | 473.06 |
| Std. dev | 95.89 | 60.11 | 102.22 |
| | Baseline vs. post Treatment | Post Treatment vs. After Removal | Baseline vs. After Removal |
| T test | P < 0.05 | P < 0.05 | Not Significant |

Conclusion:

Skin retraction times were significantly reduced by 30% when LP A+B was applied (P<0.05) as compared to baseline, hence, providing greatly improved skin recoil properties.

The results described above in Examples 2 and 3 highlight the utility and benefit of the LP A+B film as compared to petrolatum treatment for skin with compromised barrier function. The superior hydration benefits, coupled with the ease of application, film durability and cosmetic aesthetics, makes this polymer emulsion system a compelling alternative for management of skin in dermatological disorders such as lichen simplex chronicus, cutaneous lupus, psoriasis, eczema, chronic dry skin, xeroderma, rosacea, ichthyosis, or an ulcer, or any combination thereof.

Example 4

Evaluation of Clinical Efficiency for Management of Specific Skin Conditions

Background

Emollient based moisturizers are often considered an adjuvant therapy and an essential part of the management of many dry skin conditions such as dermatitis and psoriasis to increase hydration of the keratin of stratum corneum (SC).

Topical use of moisturizers often requires multiple applications per day to be effective and to prevent it from wearing off by contact, sweat and other normal activities. Emollient base moisturizers can also cause a few side effects, such as irritant dermatitis, allergic contact dermatitis, allergy to formula constituents, stinging, cosmetic acne, and other undesired effects.

In comparison with other emollient based moisturizers in terms of occlusion and efficiency of skin hydration, formulations of described herein are unobtrusive to the normal activity of the wearers having potential for the convenient (single application per day), localized, prolonged moisturization effect to the skin.

Evaluation of the use of the formulation described herein are described below.

Atopic Dermatitis (AD)

Experimental Design:

Subjects 24 to 48 patients with AD based upon the criteria proposed by Haffin and Rajka (1980)[1] including male and female with no age restrictions. Patients will be interviewed about the disease duration of AD, other atopic disorders including asthma or allergic rhinitis, and other seasonal difference in AD severity and their treatment history such as steroids, moisturizer or oral anti-histamines. Patient questionnaires are also given to patients for self evaluations on severity of conditions and life quality such as sleep pattern.

Inclusion Criteria:

1. Male and female at any age
2. Agrees to refrain from exercising and/or drinking hot or caffeinated beverages during the 2 hours prior to their appointment on the day of testing (this affects the measurements)
3. Willing and able to follow all study requirements and restrictions
4. Is able to read, understand, and sign the consent form.

Exclusion Criteria:

a. Is pregnant, nursing or planning a pregnancy as determined by interview.
b. Is currently going through menopause (i.e., experiencing hot flashes).
c. Is a smoker.
d. Any other condition or factor the Investigator or his duly assigned representative believes may affect the skin response or the interpretation of the test results.

Each patient is NOT instructed to stop the use of all moisturizing products (soaps, lotions, sunscreens, insect repellent, etc.) during a 3 day pre-conditioning period prior to testing which is usually instructed to follow for regular hydration studies. However, patients is instructed not to exercise or drink hot or caffeinated beverages within 2 hours prior to their day of testing visit as this will affect the measurements.

Treatments and Procedures

Anyone with marks, scars, scratches or any skin condition and dry skin are NOT excluded at this time. Two or six 5 cm by 5 cm test sites are outlined on the subject's skin on disease affected skin (skin lesion) and normal looking skin using a standard template.

Test Products:

The test products are labeled as follows:

| Test Article | Description |
|---|---|
| AN109 - Product 1 PDMS complex | Skin care primer cream (Step1) |
| AN 109 - Product 2 Activator | Skin care serum (Step 2) |

Test Product Application:

Products will be applied in two to six lesions identified as disease affected skin and in two to three normal looking skin area.

2-Step Test Product (AN109—Product 1 and 2):

The AN109-1 and 2 are applied once a day throughout 2 weeks daily. An aliquot of 0.08-0.1 mL is dispensed to finger and then directly applied to the test area. The two materials are applied to the same test area, the first test material (AN109-H1, 0.08 mL per 5 $cm^2$ area) is applied to skin first and the second test material (LPS 021, 0.1 mL per 5 $cm^2$) is dispensed with a new finger cot and applied onto the same area treated with the first test material by gliding motion to coat the treated area but not by rubbing in to minimize the mixing of the two test materials.

Removal Before Clinical Measurements:

All the test area is cleansed with AN109-Remover. The remover is shaken well to be homogeneous prior to use. The removal tonic (1.5 mL per 5 $cm^2$) is be poured onto a cotton round pad and then the wet pad is placed on the test area.

Clinical Measurements

I. Disease severity: SCORAD (severity scoring of AD, score range of 0-103; European Task Force on Atopic Dermatitis, 1993) utilizes the rule of nines with six clinical features of AD disease intensity (eythema/darkening, edema/population, oozing/crust, excoriations, lichenification/prurigo, and dryness).

II. Children's Dermatology Life Quality Index (CDLQI) or DLQI: DLQI[2] for adults and CDLQI[3] for children were evaluated by the questionnaire to measure how much a patient's disease had affected their lives over the last weeks. The response to each questionnaire was defined as 0-3 (0=not at all affected; 3=very much affected). DLQI was summarized under six subscales: "Symptoms and feelings;" "Leisure;" "Personal relationships;" "Treatment;" "Work and school;" and "Daily activities." The CDLQI was summarized under six subscales: "Symptoms and feelings;" "Leisure;" "Personal relationships;" "Treatment;" "School or holidays;" and "Sleep." Total QOL score was calculated by summing the score of each question. Total QOL score and the six subscales were expressed as a percentage of the respective maximum scores. The reliability and validity of DLQI were assured in the review[4].

III. TEWL and Conductance: Protocol is as described above in Example 2

IV. Tape Stripping: Quantification of the number of sequential D-squame tape strippings required to increase TEWL by 20 g/$m^2$ per hour V. Stratum Corneum (SC) Thickness: SC thickness is calculated from low-frequency susceptance and high-frequency admittance by the corneometer as (square root of low-frequency susceptance)/(high-frequency $admittance^2$). SC thickness is also visualized by conventional immunohistostaining.

VI. Immunohistochemical staining: Immunoperoxidase staining of paraffin-embedded sections is performed using the ChemMate Peroxidase/DAB system (Dako Cytomation, Hamburg, Germany) to visualize the Sc and epidermal structure, epidermal thickness and extracellular lamellar membranes.

VII. Laboratory tests: Peripheral blood EOS count (number 100 per ml; normal 40-440), serum LDH (IU $l^{-1}$; normal 119-229), total serum IgE (IU $ml^{-1}$; normal 0.0-400.0), and allergen-specific IgE (SRL Inc., Tokyo, Japan) are measured. Allergen-specific IgE were estimated by fluoroenzyme immunoassays for house dust, mite allergen, grass pollen (Tancy), cedar pollen, fungal allergen (Candida), animal dander, and foods. Concerning to the sensitivity for detection of specific IgE, 100 lumicount and values greater than or equal to 100 lumicount are considered positive (+).

VIII. Statistical analysis: Simple regression analyses are also used to identify significant associations of SC hydration, thickness, or TEWL to OSCORAD. Data with P-values less than 0.05 are evaluated as significant. We interpret P-values less than 0.005 as highly significant. Wilcoxon rank sum test and simple regression analyses are performed to assess the association or correlation between different biological markers including IgE, LDH, EOS, and the OSCORAD.

Expected Results

Improved SCORAD and DLQI and decreased TEWL over both disease affected and unaffected normal looking skin are expected. The decrease in TEWL is in parallel with SCORAD score. Both SC integrity measure by epidermal thickness and hydration are improved slowly but significantly during 2 week treatment period. The ultrastructure of the SC treated with AN109-Product1 and 2 shows improved SC integrity and barrier function and subsequently reduces inflammation by "barrier repair" achieved with application of AN109-1 and 2.

References

[1] Hannifin J M, Rajka G (1980) Diagnostic features of atopic dermatitis. Acta Derm Venereol 92:44-7. European Task Force on Atopic Dermatitis (1993) Severity scoring of atopic dermatitis: the SCORAD index. Dermatology 186: 23-31

[2] Yamamotto Y (1994) Measurement and analysis of skin electrical impedance. Acta Derm Venereol 185: 34-8

[3] Finlay A Y, Khan G K. (1994) Dermatology Life Quality Index (DLQI)—a simple practical measure for routine clinical use. Clin Exp Dermatol 19: 210-216.

[4] Lewis-Jones M S, Finlay A Y. The Children's Dermatology Life Quality Index (CDLQI): initial validation and practical use. Br J Dermatol 1995; 132: 942-949.

[5] Basra M K, Fenech R, Gatt R M, et al. The Dermatology Life Quality Index 1994-2007: a comprehensive review of validation data and clinical results. Br J Dermatol 2008; 159: 997-1035.

II. Psoriasis

Background

Psoriasis affects 2-3% of the world's population and has one of the biggest impacts on quality of life of any dermatological disorder. Treatment is extremely costly and prevention of disease progression in severity and extent is crucial. Emollients and moisturizers are essential in the topical treatment of psoriasis. They are adjuvants for classic treatments and help to reduce the scale load of individual patients. Skin hydration has been shown to significantly improve skin conditions and quality of life for psoriasis patients. They are a valuable first-line treatment, as dry skin is common and adds to the irritability of the diseased skin. Skin hydration provides transient relief from irritation. Subsequently, an improved barrier function and stratum corneum hydration makes the epidermis more resistant to external stressors and reduces the induction of Koebner phenomena (excoriation, maceration and infectious foci (Streptococcus pyogenes)).

Experimental Design:

Subjects 48 to 64 patients suffering from moderate to severe psoriasis *vulgaris* participate in this study. The age range is 18±70 years and the population includes men and women. They are evaluated for the severity of their disease on the morning following their arrival at the test site by a dermatologist and are followed up by the same dermatologist during their 2 week test period. The patients are instructed not to apply ointment or oil prior to the examination.

Clinical Measurements

I. Psoriasis Area and Severity Index (PASI) Score: This index is based on the quantitative assessment of three typical signs of psoriatic lesions: erythema (redness), infiltration (thickness), and desquamation (scaling), on a scale of 0±4, combined with the skin surface area involved. The basis for the PASI score is the evaluation of four separate body areas: head, trunk, and upper and lower extremities. Scoring them separately for erythema, infiltration, and desquamation, after establishing the extent of skin surface involved, is time-consuming, and may take 10±15 min even for experienced personnel. The PASI score is calculated as follows:

$PASI=0.1(Eh+Ih+Dh)Ah+0.3(Et+It+Dt)At+0.2(Eu+Iu+Du)Au+0.4(El+Il+Dl)Al$ where E=erythema; I=infiltration; D=desquamation;
A=area; h=head; t=trunk; u=upper extremities; and l=lower extremities An Example form is provided below:

PSORIASIS AREA AND SEVERITY INDEX (PASI)
Patient's Name: _____ File #: _____

| Upon Arrival | ERYTHEMA (0-4) | DESQUAMATION (0-4) | INFILTRATION (0-4) | INVOLVEMENT* (in %) |
|---|---|---|---|---|
| Head | | | | |
| Trunk | | | | |
| Upper Limbs | | | | |
| Lower Limbs | | | | |

| Before Departure | ERYTHEMA (0-4) | DESQUAMATION (0-4) | INFILTRATION (0-4) | INVOLVEMENT* (in %) |
|---|---|---|---|---|
| Head | | | | |
| Trunk | | | | |
| Upper Limbs | | | | |
| Lower Limbs | | | | |

| ERYTHEMA | DESQUAMATION | INFILTRATION |
|---|---|---|
| 0—No | 0—No | 0—No |
| 1—Slight | 1—Small and Few | 1—Slight |
| 2—Moderate | 2—Small | 2—Moderate |
| 3—Severe | 3—Many | 3—Deep |
| 4—Very Severe | 4—Big and Many | 4—Very Deep |

*For each part of the body, in percentace of this part.

J. TEWL and Conductance: Protocol is as described in Example 2.

K. Cutaneous Resonance Running Time (CRTT) on psoriatic lesions by Revicometer RVM 600: A Courage—Khazaka Reviscometer RVM600 (CKelectronic GmbH, Koin, Germany) is used to measure the CRRTs in psoriatic lesions on the extensor of forearm and the contralateral uninvolved sites served as control. The measurement area with this probe is 8 mm. And the acoustical shockwave running distance is 2 mm with energy of 1.77 1J. Measurements are begun in the 12 o'clock position, which is determined with the right forearms laid on the table as described previously$_{2,3}$. Measurements are then taken clockwise at every 1 h interval or at every 30° C. These measurements provide the CRRTs in the directions of 0-6 o'clock, 1-7, 2-8, and so on. Readings in 1-7, 2-8, 3-9, 4-10, and 5-11 o'clock direction on the left forearm are compared with those in 5-11, 4-10, 3-9, 2-8, 1-7 o'clock direction, respectively, on the right forearm. All subjects rested at 20-24° C., at a relative humidity of 50-55% for 30 min before measurements are taken.

L. Stratum Corneum (SC) Thickness: Protocol is as described above for AD.

M. Immunohistochemical staining: Protocol is as described above for AD.

N. Statistical analysis: Simple regression analyses are also used to identify significant associations of SC hydration, thickness, or TEWL to PASI. Data with P-values less than 0.05 are evaluated as significant. We interpret P-values less than 0.005 as highly significant. Wilcoxon rank sum test and simple regression analyses are performed to assess the association or correlation between different biological markers including IgE, LDH, EOS, and the PASI.

Expected Results

Improved SCORAD and DLQI and decreased TEWL over both disease affected and unaffected normal looking skin are expected. The decrease in TEWL is in parallel with SCORAD score. Both SC integrity measure by epidermal thickness and hydration are improved slowly but significantly during 2 week treatment period. The ultrastructure of the SC treated with AN109-Product1 and 2 shows improved SC integrity and barrier function and subsequently reduces inflammation by "barrier repair" achieved with application of AN109-1 and 2.

References

[1] Fredriksson T, Pettersson U. Severe psoriasis—oral therapy with a new retinoid. Dermatologica (1978) 157: 238-241.

[2] Song S P, Lv C Z, Zhang X J, Shi Y J, Elias P M, Feingoid K R, Man M Q. (2009) Decreased cutaneous resonance running time in cured leprosy subjects, Skin Pharmacol Physiol 22: 218-224.

[3] Xin S, Man W, Fluhr J W, Song S, Elias P M, Man M Q. (2010) Cutaneous resonance running time varies with age, body site and gender in a normal Chinese population. Skin Res Technol 1.6: 413-421.

III. Eczema

Background

Eczema is a chronic inflammatory skin disease associated with cutaneous hyperreactivity to environmental stimuli that are otherwise tolerant among normal subjects.[1]

Experimental Design:

Subject 48 to 64 patients with eczema participate in this study. The age range is 6±70 years and the population includes men and women. Patients with eczema diagnosed according to widely accepted criteria[2] are recruited from our dermatology clinic. Eczema severity is assessed by SCORAD. Patients are classified into mild, moderate and severe eczema.

Clinical Measurements

SCORAD: Protocol is as described above for AD.

Hand Eczema Severity Index (HECSI): Product tolerability is assessed using the Hand Eczema Severity Index (HECSI)₃, which is a clinical grading system of dermatitis of the hands assessing erythema, induration/papulation, vesicles and fissuring and the subject's perception of stinging/burning and itching.

Nottingham Eczema Severity Score (NESS): The clinical severity is also assessed using the Nottingham Eczema Severity Score (NESS).[4,5]

TEWL and Skin Conductance or Capacitance: Protocol is as described above for AD.

Tape Stripping: Protocol is as described above for AD.

Stratum Corneum (SC) Thickness: Protocol is as described above for AD.

Immunohistochemical staining: Protocol is as described above for AD.

Laboratory tests: Refer AD

In addition, serum LL-37 concentration is measured using enzyme immunoassay (Bachem, San Carlos, Calif., USA). Samples are diluted 90-fold prior to measurement. The sensitivity of this assay was 1 ng/mL[6].

Expected Results

Improved SCORAD and DLQI and decreased TEWL over both disease affected and unaffected normal looking skin are expected. The decrease in TEWL is in parallel with SCORAD score. Both SC integrity measure by epidermal thickness and hydration are improved slowly but significantly during 2 week treatment period. The ultrastructure of the SC treated with AN109-Product1 and 2 shows improved SC integrity and barrier function and subsequently reduces inflammation by "barrier repair" achieved with application of AN109-1 and 2.

Reference

[1] Leung D Y, Bieber T. (2003) Atopic dermatitis. Lancet 361: 151-160.

[2] Hanifin J M, Rajka G. (1980) Diagnostic features of atopic dermatitis. Acta Derm (Stockh) 92: 44-47.

[3] Held E, Skoet R, Johansen J D, Agner T. (2005) The Hand Eczema Severity Index (HECSI): a scoring system for clinical assessment of hand eczema. A study of inter- and intra-observer reliability. Contact Dermatitis 152:302-7.

[4] Emerson R M, Charman C R, Williams H C (2000) The Nottingham Eczema Severity Score: preliminary refinement of the Rajka and Langeland grading. Br J Dermatol 142: 288-97.

[5] Hon K L, Ma K C, Wong E et al. (2003) Validation of a self-administered questionnaire in Chinese in the assessment of eczema severity. Pediatr Dermatol 20: 465-9.

6 Leung T, Ching K, Kong A, Wong G, Chan, Hon K. (2011) Circulating LL-37 is a biomarker for eczema severy in children. J Eur Acd Dermatol Venereol April 22 [Epub ahead of print]

IV. Ichthyosis *Vulgaris*

Background

The most common monogenic disorder of keratinisation, ichthyosis *Vulgaris*, is associated with AD and related atopic manifestations in up to 50%[1]. X-linked ichthyosis (XLI) is a relatively common, recessive condition caused by mutations in the steroid sulfatase (STS) gene. Common loss-of-function mutations in the filaggrin gene (FLG) cause ichthyosis *vulgaris* and predispose individuals to atopic eczema or atopic dermatitis.

Experimental Design:

Subjects 48 to 64 patients with Ichthyosis *Vulgaris* participate in this study. The age range is 6±70 years and the population includes men and women. Patients with Ichthyosis *Vulgaris* diagnosed according to widely accepted criteria[1] are recruited from our dermatology clinic. Ichthyosis *Vulgaris* severity is assessed by SCORAD. Patients are classified into mild, moderate and severe Ichthyosis *Vulgaris*.

Clinical Measurements

Clinical Severity: Visual analogue scale (VAS), the Investigator's Global Assessment (IGA) and the Ichthyosis *Vulgaris* Area and Severity Index (EASI), Skin Dryness (Pruritus Severity Index Score)[3]

TEWL and Skin Conductance or Capacitance: Protocol is as described above for AD.

Tape Stripping: Protocol is as described above for AD.

Stratum Corneum (SC) Thickness: Protocol is as described above for AD.

Immunohistochemical staining: Protocol is as described above for AD.

Expected Results

Improved SCORAD and DLQI and decreased TEWL over both disease affected and unaffected normal looking skin are expected. The decrease in TEWL is in parallel with SCORAD score. Both SC integrity measure by epidermal thickness and hydration are improved slowly but significantly during 2 week treatment period. The ultrastructure of the SC treated with AN109-Product1 and 2 shows improved SC integrity and barrier function and subsequently reduces inflammation by "barrier repair" achieved with application of AN109-1 and 2.

References

[1] Williams H C, Burney P G, Pembroke A C, Hay R J (1994) The U.K. Working Party's Diagnostic Criteria for Atopic Dermatitis. III. Independent hospital validation. Br J Dermatol 131(3): 406-16.

[2] Sandilands A, Terron-Kwiatkowski A, Hull P R, O'Regan G M, Clayton T H, et al. (2007) Comprehensive analysis of the gene encoding filaggrin uncovers prevalent and rare mutations in ichthyosis *vulgaris* and atopic eczema. Nat Genet 39(5): 650-654

[3] Lee K C, Keyes A, Hensley J R, Gordon J R, Kwasny M J, West D P, Lio P A. (2011) Effectiveness of acupressure on pruritus and lichenification associated with atopic dermatitis: a pilot trial. *Acupunct Med*. December 28. [Epub ahead of print]

Summary of Clinical Endpoints and Biomarkers

| Dermatosis Type | Clinical Endpoint | Biomarker |
|---|---|---|
| Atopic Dermatitis | 1. Cutaneous Barrier Function and Homeostasis SCORAD or OSCORAD (Objective Severity Scoring of Atopic Dermatitis) 6 intensity items: Erythema, Edema/Papulation, Oozing/Crust, | I. Cutaneous Barrier Function and Homeostasis (Skin Biopsy) Epidermis Cell Proliferation and Hyperplasia Immunohistochemical (IHC) staining of PCNA, Ki67, Ki-S3, |

-continued

| Dermatosis Type | Clinical Endpoint | Biomarker |
|---|---|---|
| | Excoriatio, Lichenfication, Dryness, Pruitus<br>Sleep loss<br>Children's Dermatology Life Quality Index (CDLQI)<br>TEWL (Transepidermal Water Loss)<br>    Stratum Corneum (SC) water holding capacity<br>    Conductance or Capacitance<br>    SC water accumulation | or other proliferation markers<br>Lamellar bodies quantity in SC and Stratum Granulosum (SG)<br>Epidermal Differentiation<br>    IHC staining of Involucrin, Keratins CK 5, 6, 17, 1, 5, 10, 14 or other differntiation markers<br>Epidermal Thickness<br>    Light microscopy or Corneometer<br>Cellular Structure<br>    Confocal Tandem Scannign Microscope (TSM): In depth (200 uM) measurement of the thickness of the different layers<br>    Optical coherence tomography (OCT)- Arrangement of the collagen fibres<br>SC and epidermal lipid<br>    Lipid content<br>    Ceramide quantity<br>    mRNA levels of the epidermal glucosylceramide transport protein (ATP-binding cassette A12)<br>SC and epidermal protein<br>    Filaggrin (FLG)<br>    Aquaporin (AQP3)<br>    Protease activated receptor-2 (PAR-2)<br>    Caveolin-1 (cav-1)<br>Skin Surface pH |
| | 2. SC Integrity and Cohesion<br>    Tape Stripping<br>        Qunatification of the number of sequential D-squame tape strippings required to increase TEWL by 20 g/m2 per hour | II. SC Integrity and Cohesion (Skin Biopsy)<br>    1. Serine proteases (in situ zymography)<br>    2. Desmoglein (Western Blot)<br>    3. Corneodesmosome (Western Blot)<br>    4. B-glucocerebroside activity (WB)<br>    5. Lipid processing (SEM) |
| | 3. Inflammation<br>    SCORAD<br>        Erythema, Edema/Papulation, Oozing/Crust, Excoriatio, Lichenfication | III. Inflammation (Blood samples)<br>    Immunoglobulin E (IgE)<br>    Mast cell hyperactivity<br>    Dendritic cell signaling |
| Psoriasis | TEWL<br>Conductance or Capacitance<br>Clinical Scores on Eythema, | The same biomarkers in AD but do NOT include:<br>SC and epidermal protein |

-continued

| Dermatosis Type | Clinical Endpoint | Biomarker |
|---|---|---|
| | Desquamation (flaking-corneocyte counting of D-Squame), Lichenification, Skin Dryness (Pruritus Severity Index Score)-Psoriasis Area and Severity Index (PASI) Score Self-reported Questionnaires Cutaneous Resonance Running Time (CRTT) on psoriatic lesions by Revicometer RVM 600 SC Integrity and Cohesion Tape Stripping Qunatification of the number of sequential D-squame tape strippings required to increase TEWL by 20 g/m2 per hour | Filaggrin (FLG) Aquaporin (AQP3) Protease activated receptor-2 (PAR-2) Caveolin-1 (cav-1) |
| Eczema Contact eczema Allergic contact eczema Seborrheic eczema Nummular eczema Neurodermatitis Stasis dermatitis; Retinoid-induced irritant dermatitis | SCORAD TEWL Conductance or Capacitance Hand Eczema Severity Index (HECSI) Nottingham Eczema Severity Score (NESS) | The same biomarkers in AD and also include: icidin Expression of antimicrobial peptides 1. Circulating LL-37 corresponding to amino acids 134-170 of human cathelicidin |
| Ichthyosis Vulgaris | TEWL Conductance or Capacitance Skin Dryness (Pruritus Severity Index Score) Tape Stripping Qunatification of the number of sequential D-squame tape strippings required to increase TEWL by 20 g/m2 per hour | Biomarkers for Cutaneous Barrier Function and Homeostasis SC Integrity and Cohesion (Skin Biopsy) but do NOT include: SC and epidermal protein Filaggrin (FLG) Aquaporin (AQP3) Protease activated receptor-2 (PAR-2) Caveolin-1 (cav-1) |
| Xeroderma (Abnormally Dry Skin) | TEWL Conductance or Capacitance Skin Dryness (Pruritus Severity Index Score) Tape Stripping Qunatification of the number of sequential D-squame tape strippings required to increase TEWL by 20 g/m2 per hour | Biomarkers for I. Cutaneous Barrier Function and Homeostasis I. SC Integrity and Cohesion (Skin Biopsy) but do NOT include: SC and epidermal protein Filaggrin (FLG) Aquaporin (AQP3) Protease activated receptor-2 (PAR-2) Caveolin-1 (cav-1) |

-continued

| Dermatosis Type | Clinical Endpoint | Biomarker |
|---|---|---|
| Others Rosacea- Disease driven secondary skin issues (i.e. Vascular ulcers, diabetic foot ulcers) | | |

Example 5

Viscosity Measurements

The viscosity of a fluid can be measured by many methods known to one of skill in the art. Specifically, "The rheology handbook: for users of rotational and oscillatory rheometers By Thomas G. Mezger" or ASTM standards such as ASTM D3835-08, ASTM D2857-95, ASTM D2196-10, and ASTM D2983-09 instruct one of skill in the art on how to measure the viscosity of a fluid. Illustrative methods also include the following methods:

Method A

5 Overview

This protocol determines the viscosity (cP) on a Brookfield Viscometer. This protocol can be performed on a wide variety of formulations including but not limited to immediate effects treatment, and perfector.

6 Background

The viscosity of formulation is critical to its performance and its aesthetics. Furthermore a change in viscosity with time or exposure to a stress condition is an important indicator of formulation instability. As such, it is important to be able to reproducibly and accurately evaluate formulation viscosity. The following protocol can be used to determine the viscosity at single shear rate of a formulation whose viscosity is between 50 and 300 Pas.

7 Materials

1. A full 2 oz to 8 oz jar containing formulation of interest
2. Brookfield DV-II+ Pro EXTRA Viscometer and RV-6 spindle.
3. Test requires ~5 minutes per sample 8 Analytical Precautions Clean the viscometer geometry prior to use Insert the geometry to the appropriate depth in the center of the sample container Insure the container is stationary during the test 9 Protocol 7. 5.1 Preparing Equipment:
  I. Turn on the Brookfield DV-II+Pro EXTRA Viscometer by pressing a switch in the back of the instrument. Select "External Mode" by pressing the up arrow on the instrument control panel.
  II. Start the Rheocalc software, a shortcut to which can be found on the desktop
  III. Zero the viscometer by clicking the lightning symbol on the dashboard tab (Instrument geometry should NOT be installed)
  IV. Find RV-6 test geometry and clean with 50%/50% IPA/Mineral Spirits mixture, then wipe dry
  V. Insert RV-6 geometry by pulling the instrument geometry holder sleeve up.
  VI. Pick the test method by clicking Test tab, and opening Hold0.5-RV6-081511.RCP method.
8. 5.2 Preparing Sample:
9. 3 No special sample preparation is required other than doing a visual inspection to ensure the sample appears uniform.

Perform Viscosity Measurement:

Insert the geometry into the 2 to 8 oz of sample under.

Insure that the geometry is inserted to the correct measuring height as indicated by thin section in the rod of the geometry Insure that the geometry is centered in the jar Adjust the stand so as to keep the sample and the geometry in the appropriate relative position.

Click the small play button in the test tab to start the test

Name the data file appropriately and save the file to the appropriate location

Allow the test to run to completion, then save your data for later analysis

To test another sample:

Slide the sample stand out and remove the sample from the instrument

Remove the geometry from the instrument and gently wipe down all surfaces with 50% IPA, 50% Mineral Spirit mixture. Dry with a lint free wipe.

Replace the geometry, return to test tab and start next test

VII. After finishing with the last test sample, clean geometry with 50% IPA, 50%

Mineral Spirit mixture, then wipe dry and place back in geometry box.

10 Data Analysis

Open datafile (*.DB) and click the export button to obtain an excel file containing the data.

Locate the ViscometerPerfectorTemplate_JL-081511-v1-beta1.xlsx Excel template for data analysis Paste the data into the first sheet Record the average viscosity and the standard deviation Save the template as an electronic record with a new name that references the analyzed sample.

1. Repeat analysis for each data set.

Method B

Overview

This protocol determines the viscosity (Pas) at 0.5 1/s, Shear Thinning factor (Pa*s^2), and the strain rate of instability. This protocol can be performed on a wide variety of formulations including but not limited to immediate effects treatment, and perfector, along with any other "cream" or "lotion"

Background

The viscosity of formulas and its change has been correlated to stability of formulations. As such, it is important to be able to reproducibly and accurately evaluate their viscosity properties to be used as a predictive tool for stability of Immediate Effects active prototypes. The following protocol can be used to determine the viscosity, shear thinning factor, and strain rate of instability.

Materials

4. >1 g Formulation of Interest

5. Bohlin CVO100 Rheometer mounted with 20 mm Parallel plate geometry

6. Test requires ~12 minutes per sample

Analytical Precautions

Clean sides of the geometry are critical for accurate test results

Any deviations must be noted

Protocol 9. 5.1 Preparing Equipment:

VIII. Set up the Bohlin Rheometer a. Turn on the instrument b. Turn on the temperature controller c. Start the Bohlin software d. Load the viscosity stability test template e. Make sure both the geometry and plate are clean IX. Install the geometry a. Zero the instrument and you are now ready to being testing.

X. For testing of multiple samples simply raise and clean the geometry first with a dry wipe, then with a 50%/50% IPA/Mineral Spirits mixture, then again with a dry wipe.

10. 5.2 Preparing Sample:

10.3 No special sample preparation is required other than doing a visual inspection to ensure the sample appears uniform.

Perform the Viscosity Test

Place ~1 g of mixed material onto the bottom plate in a mound centered below the geometry Lower the geometry to the correct gap (250 um)

Clean the excess material from the sides of the geometry using the flat end of a spatula Allow the test to run to completion, then save your data for later analysis To continue onto the next test, raise the geometry and remove the sample from the instrument. Gently wipe down all surfaces with 50% ipa/50% mineral spirits mixture. Dry with a lint free wipe.

You are now ready to commence the next cure test

11.

12. VII. Data Analysis:

2. Locate the following Excel Template for the data analysis ViscosityStabilityTemplate061411-v2

3. Paste the raw instrument data from the appropriate Bohlin Viscometry Data File file into A:2 of sheet 1 (near the left corner) of the excel document 4. Paste the sample name into A:1 of sheet 1 of the excel document 5. Record the calculated "Viscosity (Pas) at 0.5 l/s" as viscosity 6. Record the calculated "Shear Thinning factor (Pa*s^2)" as the shear thinning factor 7. Record the calculated "Strain Rate of instability" as the Strain Stability (Scale is out of 100)

8. Save the completed template as an electronic record with an appropriate file name 9. Repeat steps 2 to 7 for remaining raw data

Example 6

Toxicity Studies

To date, the formulation, compositions, films and method of the invention have been administered to approximately 200 subjects and no irritancy, allergy, or other usage problems have been identified.

Example 7

Figure 3A:
FIGS. 3a-3e are a series of photographs demonstrating the effect of the formulation on post-laser treated skin.
Figure 3B:
Figure 3C:
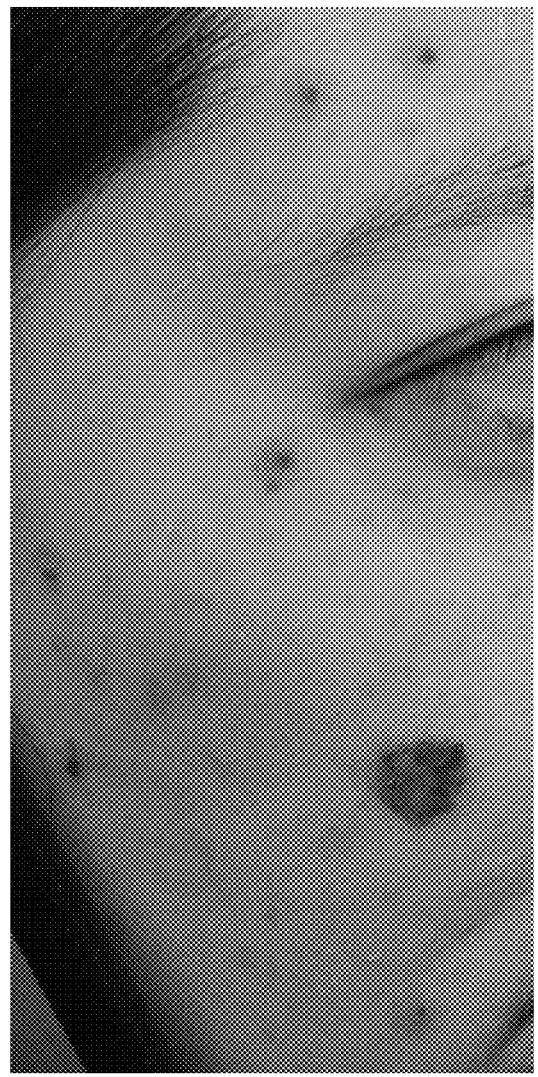
Figure 3D:
Figure 3E:
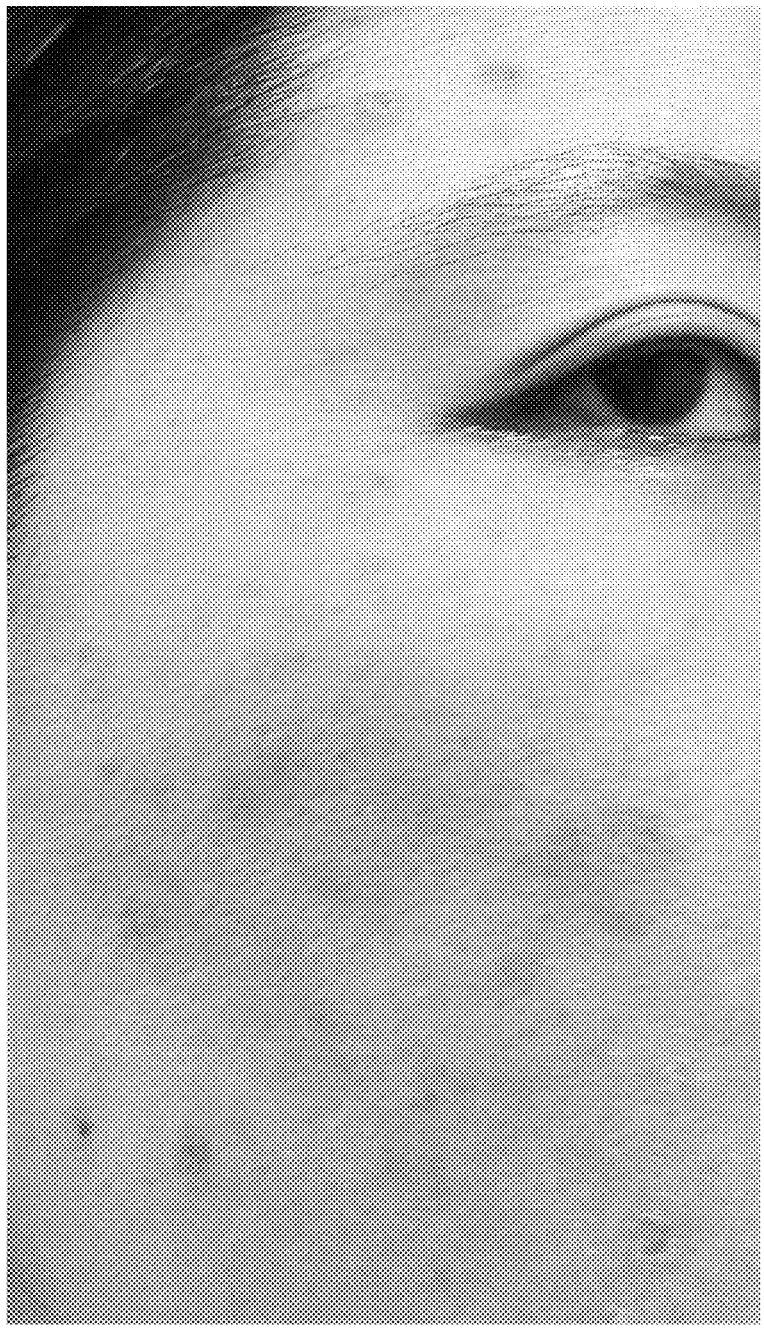

Evaluation of Clinical Efficiency for Post-Laser Treatment Recovery Management: Post Treatment Management of Pigmented Lesion Removal Following the laser application to a pigmented lesion [Q-switched 694 nm Ruby laser, 6.5 mm spot treated, 4.0-4.5 J/cm$^2$], the reactive reinforcing component was applied to the treatment site followed by the crosslinking component, to form the film, as described above in Example 2. The film was worn for 24 hours, removed and a new film was applied on the subsequent day. This procedure was repeated for 3 consecutive days. The pigmented scab sloughed off with the film on the fourth day, leaving a repaired, unpigmented skin site. FIGS. 1a-1e are photographs of the post-laser treated area post treatment (FIG. 3a); 24 hours post-treatment (FIG. 3b); 24 hours post treatment and with application of the formulation to form film (FIG. 3c); 72 hours post treatment, 48 hours after application of the formulation to form film (FIG. 3d); and 80 hours after application of the formulation to form film the film is removed and the pigmented lesion sloughs off with the film (FIG. 3e).

Example 8

Evaluation of Clinical Efficiency for Management of Eczema

Objective: Use of Formulation on Subjects with Eczema

Study Protocol:

Panel: 3 women above the age of 40, self-reporting a diagnosis of eczema by dermatologist.

In addition, each panelist must have one or more visible lesions of eczema to participate in study.

Test Materials: Formulations of Step 1 (Treatment)+Step 2 (Perfector)

Step 1: LPS033

| Component No. | Component | Percent of Formulation (%) |
|---|---|---|
| 1 | Andsil VS10,000 | 14.13 |
| 2 | Andsil VS165,000 | 3.30 |
| 3 | Andsil XL-11 | 6.92 |
| 4 | Aerosil R8200 | 8.98 |
| 5 | PMX-1184 | 13.33 |
| 6 | RM 2051 | 5.00 |
| 7 | Water | 48.01 |
| 8 | Jeecide CAP-5 | 0.33 |

Step 2: LPS034:

| Component No. | Component | INCI | Percent of Formulation (%) |
|---|---|---|---|
| 1 | water | Water | 28.50% |
| 2 | Jeecide CAP-5 | Phenoxyethanol (and) Caprylyl Glycol (and) Potassium Sorbate (and) Hexylene Glycol | 0.50% |
| 3 | Sodium Chloride | Sodium Chloride | 1.00% |
| 4 | Plantacare 818 UP | Coco-glucoside | 0.50% |
| 5 | Propylene Glycol | Propylene Glycol | 20.00% |
| 6 | Glycerin | Glycerin | 4.00% |

-continued

| Component No. | Component | INCI | Percent of Formulation (%) |
|---|---|---|---|
| 7 | 1,3-Butylene Glycol | 1,3-Butylene Glycol | 10.00% |
| 8 | Dow 9011 Elastomer Blend | Cyclopentasiloxane (and) PEG-12 Dimethicone Crosspolymer | 10.00% |
| 9 | Dow 9045 Elastomer Blend | Cyclopentasiloxane and Dimethicone Crosspolymer | 10.00% |
| 10 | KF-995 | Cyclopentasiloxane | 10.00% |
| 11 | Nylon 10-I2 | Nylon-12 and Isopropyl Titanium Triisostearate | 4.50% |
| 12 | Karstedt Catalyst | Platinum | 1.00% |

Study Endpoints:

Live and Photo evaluation of treatment site

Patient feedback

Pre-Study Visit: Screening, 20 minute visit:

Each panelist was asked to fill out a questionnaire required them to provide personal information. The personal questions addressed medical history, and current medications (topical or oral) for treating the specific skin condition. The panelists were instructed to use the product on the designated areas continuously for two or three weeks and make two additional 30 minute visits to the test site. Prior to leaving the Pre-Study visit, the designated skin sites were photographed.

Study Protocol—14 days, 2-30 minute visits:

The skin lesions were determined at the Pre-study visit and each of these designated skin lesion sites were treated with the formulations (Step 1 and Step 2). Two of the three panelists were instructed to apply the formulation daily, minimally once a day, and repeating the application if the film was removed for the entire two week study period. The third panelist was asked to continuously wear the formulation for the first week of the study, but then not use the formulation for the second week and then to resume treatment for the third week. Each panelist documented the progression of their skin condition via daily photos to track the progression and changes of their skin appearance.

At the 1 week and 2 week time points, the skin condition of each panelist was evaluated by the study coordinator. Each panelist reported any irritation or changes in skin appearance as a result of the use of the formulation to the study coordinator. At each of these visits, photographs were taken of the designated test skin sites.

TABLE 1

Procedures for each day during the study period

| Task: | Visit 1 Pre-Study Visit | Day 2-6 | Visit 2 Day 7 | Day 8-13 | Visit 3 Day 14 |
|---|---|---|---|---|---|
| Determine type of skin diseases | x | | | | |
| Determine Patient Qualification | x | | | | |
| Determine Compliance | x | | | | |
| Recruitment Decision | x | | | | |
| Sign Consent/Rate Form | x | | | | |
| Take Picture During Visit | x | | x | | x |
| Take Picture and Email to Study Coordinator | | x | | x | |
| Training of application of Step 1 and Step 2 formulations | x | | | | |
| Kit Distribution | x | | | | |
| Treatment Site Determination | x | | | | |
| Documentation of irritation and other observations | | | x | | x |
| Kit Collection | | | | | x |
| Payment | x | | | | x |

Study Results:

At baseline, the panelists each had moderate eczema skin with dry, red patches, peeling skin, and moderate itchy and burning sensation. The individualized results are described below.

| Panelist | Skin lesion/Treatment Site |
|---|---|
| #1 | lower right palm of the left hand between the $3^{rd}$ and $4^{th}$, and $4^{th}$ and $5^{th}$ finger on the right hand |
| #2 | Area above the left eye $2^{nd}$ finger of the right hand |
| #3 | Entire palm of the right hand |

Panelist 1:

Baseline: Skin was raw, red, dry and itchy with patches of flaky and peeling skin. $1^{st}$ week: use of formulation: The skin is looking visibly better within 24 hours. Specifically, the skin looked less dry and was not red. The itching went away completely. The formulation worked faster than expected; as it usually takes the hydrocortisone creams a few days to take effect. For the palm area, panelist 1 applied the product 1-2 times per day. When panelist 1 returned for the evaluation by the study coordinator, she had the product on, and the skin was healed with no signs of redness, dryness, or peeling skin.

$2^{nd}$ Week: withdrawal (no usage) of the formulation: The skin condition deteriorated: the dryness and the itching returned. The skin appeared red and had started to peel again.

$3^{4d}$ Week: use of formulation: Panelist self-reported that the skin condition is improving again and the skin looks to be healing. The dryness was gone and only one small spot of redness remained. The panelist reported that the skin was no longer itchy either.

Panelist 2:

Baseline: Skin was red, dry and itchy. Treatment sites: around eyes and finger.

1st Week: The panelist returned with ashy and dry skin, and her skin condition looked similar to baseline. However, the panelist reported that she did not wear the product continuously and applied it only once per day. Instead, if the film was removed, the formulation was not reapplied immediately, thus resulting in large gaps between treatment.

$2^{nd}$ Week: The panelist returned wearing the film formed from the formulation. The panelist's skin looked visibly better and was of a smooth texture and without redness. The panelist reported when the formulation was used her skin was neither itchy nor irritated. The panelist was instructed to continue treatment for another week with minimal time lapse between treatment.

Panelist 3:

Baseline: Skin was red, raw looking, had dry white patches, and was itchy, with visible patches of peeling skin.

$1^{st}$ Week: The panelist returned with formulation applied to her skin. The film was peeling when she arrived for the appointment, but when the film residues were brushed off, the study coordinator confirmed that her skin was no longer peeling. She had applied the product 2-3 times/day depending on her activities. Although she did not note any visible difference with the product usage, she reported that the itching has been reduced. Her skin looked less dry but still slightly red. There were no signs of irritation from formulation use, but the difference between one week of treatment and baseline was not significant.

$2^{nd}$ Week: The panelist returned with formulation applied to her skin. She had applied the product 2-3 times/day depending on her activities. Her skin looked better with the redness gone and most of the dry, peeling patches of skin healed. Again, the panelist reported no itching.

CONCLUSION

The formulation reduced or resolved the symptoms of the eczema patients involved in the study. Some of the benefits demonstrated by this study include a quicker healing time as compared to the panelists' current treatment regime, a better skin aesthetic appearance, and reduced irritation. In conclusion, an occlusive film resulting from the application of the 2-step formulations provided the protective barrier to the diseased skin with the compromised barrier function, such as the skin of eczema patients.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

We claim:

1. A method for treating eczema in a subject in need thereof, comprising:
    applying to the skin of the subject a composition comprising
    a) a reactive reinforcing component and
    b) a cross-linking component;
    wherein the reactive reinforcing component comprises a reactive constituent and a reinforcing constituent;
    wherein the reactive constituent comprises at least one organopolysiloxane ingredient of formula II and at least one hydride functionalized polysiloxane ingredient of formula III;

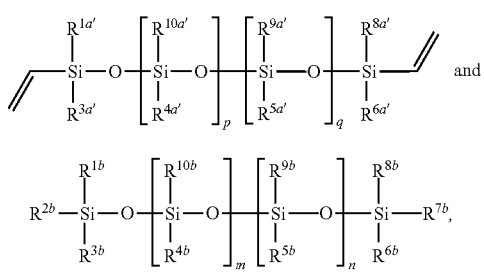

wherein
$R^{1a'}$, $R^{3a'}$, $R^{4a'}$, $R^{5a'}$, $R^{6a'}$, $R^{8a'}$, $R^{9a'}$ and $R^{10a'}$ are in each occurrence independently $C_{1-20}$ alkyl, $C_{2-20}$ alkenyl, $C_{5-10}$ aryl, hydroxyl or $C_{1-20}$ alkoxyl;
p and q are each independently an integer from between 10 and 6000;
$R^{1b}$, $R^{2b}$, $R^{3b}$, $R^{6b}$, $R^{7b}$ and $R^{8b}$ are $C_{1-20}$ alkyl;
$R^{4b}$, $R^{5b}$, $R^{9b}$ and $R^{10b}$ are in each independently selected from hydrogen, $C_{1-20}$ alkyl, $C_{2-20}$ alkenyl, $C_{5-10}$ aryl, hydroxyl or $C_{1-20}$ alkoxyl, wherein at least two of $R^{4b}$, $R^{5b}$, $R^{9b}$ and $R^{10b}$ are hydrogen; and
m and n are each independently an integer from between 10 and 6000;
wherein the organopolysiloxane ingredient comprises at least one high viscosity organopolysiloxane and at least one low viscosity organopolysiloxane,
wherein said high viscosity organopolysiloxane has a viscosity of about 100,000 to about 500,000 cSt or cP at 25° C. and the low viscosity organopolysiloxane has a viscosity of about 100 to about 50,000 cSt or cP at 25° C.;
wherein the high viscosity organopolysiloxane is vinyl terminated;
wherein the low viscosity organopolysiloxane is vinyl terminated; and
wherein said cross-linking component facilitates in situ cross-linking of the reactive reinforcing component, such that a film is formed on skin, thereby treating eczema in the subject.

2. The method of claim 1, wherein the film is used in combination with one or more additional therapeutic agents.

3. The method of claim 1, wherein the reactive reinforcing component has a viscosity of about 50,000 to about 700,000 cSt or cP at 25° C.

4. The method of claim 1, wherein the reactive reinforcing component has a vinyl to functional hydride ratio of about 1:10 to about 1:100.

5. The method of claim 1, wherein said high viscosity organopolvsiloxane has a viscosity of about 100,000 to about 175,000 cSt or cP at 25° C.

6. The method of claim 1, wherein said low viscosity organopolvsiloxane has a viscosity of about 3,500 to about 20,000 cSt or cP at 25° C.

7. The method of claim 1, wherein the crosslinking component comprises a metal catalyst.

8. The method of claim 1, wherein the film is on the skin for at least 1 hour.

9. The method of claim 1, wherein the film is on the skin for at least 4 hours.

10. The method of claim 1, wherein the film is on the skin for at least 10 hours.

11. The method of claim 1, wherein the film is on the skin for at least 16 hours.

12. The method of claim 1, wherein the film is on the skin for at least 24 hours.

13. The method of claim 1, wherein the ratio of the viscosity of the high viscosity organopolysiloxane to the viscosity of the low viscosity organopolysiloxane is between 100 and 1.

14. The method of claim 1, wherein the fractional weight of the high viscosity organopolysiloxane to the viscosity of the low viscosity organopolysiloxane is between 0.1 and 0.5.

15. A method for treating eczema in a subject in need thereof, comprising:
    applying to the skin of the subject a composition comprising
    a) a reactive reinforcing component
    wherein the reactive reinforcing component comprises a reactive constituent and a reinforcing constituent;

wherein the reactive constituent comprises at least one organopolysiloxane ingredient of formula II and at least one hydride functionalized polysiloxane ingredient of formula III;

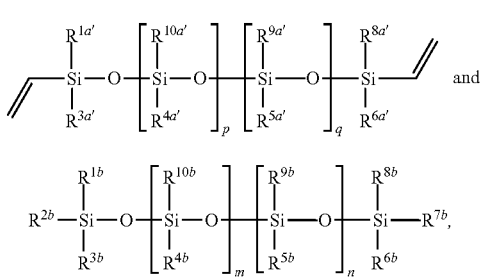

wherein $R^{1a'}$, $R^{3a'}$, $R^{4a'}$, $R^{5a'}$, $R^{6a'}$, $R^{8a'}$, $R^{9a'}$ and $R^{10a'}$ are in each occurrence independently $C_{1-20}$ alkyl, $C_{2-20}$ alkenyl, $C_{5-10}$ aryl, hydroxyl or $C_{1-20}$ alkoxyl;

p and q are each independently an integer from between 10 and 6000;

$R^{1b}$, $R^{2b}$, $R^{3b}$, $R^{6b}$, $R^{7b}$ and $R^{8b}$ are $C_{1-20}$ alkyl;

$R^{4b}$, $R^{5b}$, $R^{9b}$ and $R^{10b}$ are in each independently selected from hydrogen, $C_{1-20}$alkyl, $C_{2-20}$ alkenyl, $C_{5-10}$ aryl, hydroxyl or $C_{1-20}$alkoxyl, wherein at least two of $R^{4b}$, $R^{5b}$, $R^{9b}$ and $R^{10b}$ are hydrogen; and m and n are each independently an integer from between 10 and 6000;

wherein the organopolysiloxane ingredient comprises at least one high viscosity organopolysiloxane and at least one low viscosity organopolysiloxane;

wherein said high viscosity organopolysiloxane has a viscosity of about 100,000 to about 175,000 cSt or cP at 25° C. and the low viscosity organopolysiloxane has a viscosity of about 3,500 to about 20,000 cSt or cP at 25° C.;

wherein the high viscosity organopolysiloxane is vinyl terminated;

wherein the low viscosity organopolysiloxane is vinyl terminated; and wherein said reactive reinforcing component has a viscosity of about 50,000 to about 700,000 cSt or cP at 25° C.; and b) a cross-linking component;

wherein said cross-linking component facilitates in situ cross-linking of the reactive reinforcing component, such that a film is formed on skin, thereby treating eczema in the subject.

16. The method of claim 15, wherein said high viscosity organopolysiloxane comprises vinyl terminated polydimethylsiloxane and the low viscosity organopolysiloxane comprises vinyl terminated polydimethylsiloxane.

17. The method of claim 15, wherein the high viscosity organopolysiloxane has a weight percent of vinyl of about 0.01 to about 0.1 or a vinyl equivalent per kilogram of about 0.01 to about 0.02 or a combination of both and the low viscosity organopolysiloxane has a weight percent of vinyl of about 0.01 to about 0.3 or a vinyl equivalent per kilogram of about 0.01 to about 0.1 or a combination of both.

18. The method of claim 15, wherein said hydride functionalized polysiloxane has a viscosity of about 5 to about 11,000 cSt or cP at 25° C.

19. The method of claim 15, wherein said hydride functionalized polysiloxane has a percent SiH content of about 3 to about 45% or a SiH content of about 0.5 to about 10 mmol/g or a combination of both.

20. The method of claim 15, wherein said hydride functionalized polysiloxane is alkyl terminated.

21. The method of claim 15, wherein said hydride functionalized polysiloxane comprises trimethylsiloxy terminated methylhydrosiloxane-dimethylsiloxane copolymers.

22. The method of claim 15, wherein said reactive reinforcing component has a vinyl organopolysiloxane to functional hydride molar ratio of about 1:10 to about 1:100.

23. The method of claim 15, wherein said reinforcing constituent is selected from the group consisting of optionally surface treated mica, zinc oxide, titanium dioxide, aluminum oxide, clay or silica.

24. The method of claim 15, wherein the crosslinking component further comprises a catalyst that comprises about 0.005 to about 0.04% of the crosslinking component.

25. A method for treating eczema in a subject in need thereof, comprising:
applying to the skin of the subject a composition comprising
about 3,500 to about 20,000 cSt or cP at 25° C. vinyl-terminated dimethylpolysiloxane;
about 100,000 to about 175,000 cSt or cP at 25° C. vinyl-terminated dimethylpolysiloxane;
Alkyl-terminated silicon-hydride polysiloxane; and
Platinum-divinyltetramethyldisiloxane complex.

26. A method for treating eczema in a subject in need thereof, comprising:
applying to the skin of the subject a composition comprising:
about 10,000 cSt or cP at 25° C. vinyl-terminated dimethylpolysiloxane;
about 165,000 cSt or cP at 25° C. vinyl-terminated dimethylpolysiloxane;
Alkyl-terminated silicon-hydride polysiloxane; and
Platinum-divinyltetramethyldisiloxane complex,
thereby treating eczema in the subject.

* * * * *